US012790407B2

(12) United States Patent
Chambers et al.

(10) Patent No.: US 12,790,407 B2
(45) Date of Patent: Nov. 10, 2026

(54) CLAUDIN 18.2 ANTIBODIES, METHODS OF MAKING THE SAME, AND USES THEREOF

(71) Applicant: Integral Molecular, Inc., Philadelphia, PA (US)

(72) Inventors: Ross Stewart Chambers, Hockessin, DE (US); Joseph Benjamin Rucker, Philadelphia, PA (US); Brad Alan Screnci, Haddon Township, NJ (US); Trevor Andrew Barnes, Philadelphia, PA (US); Timothy Robin Phillips, Philadelphia, PA (US); Benjamin J. Doranz, Drexel Hill, PA (US)

(73) Assignee: Integral Molecular, Inc., Philadelphia, PA (US)

( * ) Notice: Subject to any disclaimer, the term of this patent is extended or adjusted under 35 U.S.C. 154(b) by 743 days.

(21) Appl. No.: 18/327,402

(22) Filed: Jun. 1, 2023

(65) Prior Publication Data

US 2023/0391885 A1 Dec. 7, 2023

Related U.S. Application Data

(60) Provisional application No. 63/347,647, filed on Jun. 1, 2022.

(51) Int. Cl.

| | |
|---|---|
| ***C07K 16/30*** | (2006.01) |
| ***A61P 35/00*** | (2006.01) |
| ***C12N 15/63*** | (2006.01) |

(52) U.S. Cl.

CPC .......... *C07K 16/3076* (2013.01); *A61P 35/00* (2018.01); *C12N 15/63* (2013.01); *C07K 2317/565* (2013.01)

(58) Field of Classification Search

CPC ...... C07K 16/3076; A61P 35/00; C12N 15/63
See application file for complete search history.

(56) References Cited

U.S. PATENT DOCUMENTS

| | | | | |
|---|---|---|---|---|
| 2016/0333109 | A1 | 11/2016 | Sahin et al. | |
| 2016/0339101 | A1* | 11/2016 | Sahin | A61K 33/243 |
| 2019/0309067 | A1* | 10/2019 | Sahin | C07K 16/2809 |
| 2020/0385463 | A1 | 12/2020 | Li | |

FOREIGN PATENT DOCUMENTS

| | | | |
|---|---|---|---|
| WO | WO-2013174510 | A1 | 11/2013 |
| WO | WO-2016166124 | A1 | 10/2016 |
| WO | WO-2020082209 | A1 | 4/2020 |
| WO | WO-2020168059 | A1 | 8/2020 |

OTHER PUBLICATIONS

Murphy et al. "Janeway's Immunobiology" 10th edition, 2022, Chapter 4 (Antigen Recognition by B-Cell and T-cell Receptors) (Year: 2022).*

Murphy et al. "Janeway's Immunobiology" 10th edition, 2022, Chapter 8, (The Development of B and T Lymphocytes) (Year: 2022).*

Guo, Dongjun, et al. "ImmunoMatch learns and predicts cognate pairing of heavy and light immunoglobulin chains." Nature Methods (2025): 1-12. (Year: 2025).*

Rudikoff, Stuart, et al. "Single amino acid substitution altering antigen-binding specificity." Proceedings of the National Academy of Sciences 79.6 (1982): 1979-1983. (Year: 1982).*

Rabia et al (2018) "Understanding and overcoming trade-offs between antibody affinity, specificity, stability, and solubility" Biochem Eng. J. 15(137); 365-374 (Year: 2018).*

Lees et al. "Investigating substitutions in antibody-antigen complexes using molecular dynamics: a case study with broad-spectrum, influenza A antibodies." Frontiers in Immunology 8 (2017): 143 (Year: 2017).*

Kyuno et al. "Claudin-18.2 as a therapeutic target in cancers: cumulative findings from basic research and clinical trials." Tissue barriers 10.1 (2022): 1967080 (Year: 2022).*

Hummer et al (2022) "Advances in computational structure-based antibody design" Current Opinion in Structural Biology 74(102379); 1-7 (Year: 2022).*

Davidson E, et al., A High Throughput Shotgun Mutagenesis Approach to Mapping B-cell Antibody Epitopes, Immunology, 143(1):13-20 (2014).

Finlay WJ, et al., Phage Display: A Powerful Technology for the Generation of High-Specificity Affinity Reagents from Alternative Immune Sources, Methods Mol Biol., 1485:85-99 (2017).

Finlay, W.J., et al., Optimized Generation of High-Affinity, High-Specificity Single-Chain Fv Antibodies from Multi-Antigen Immunized Chickens, Methods in Molecular Biology, Springer New York, pp. 319-338 (2016).

PCT/US2023/067768 International Search Report and Written Opinion mailed Nov. 14, 2023.

Sahin, U., et al., Claudin-18 splice variant 2 is a pan-cancer target suitable for therapeutic antibody development, Clin Cancer Res, 14(23): 7624-7634 (2008).

Screnci, B., et al., Abstract 317: Isolation of highly selective antibodies against claudin 18.2 for the treatment of solid tumors, Cancer Res, 82(12_Supplement): 317 (2022).

* cited by examiner

*Primary Examiner* — Joanne Hama
(74) *Attorney, Agent, or Firm* — Morgan, Lewis & Bockius LLP

(57) ABSTRACT

Antibodies and compositions against Claudin 18.2 and uses thereof are provided herein.

20 Claims, 16 Drawing Sheets

Specification includes a Sequence Listing.

MAb1 (IM-44-09B03-1HB)

MAb2 (IM-44-01E10-1HA)

CLAUDIN 18.2 ANTIBODIES, METHODS OF MAKING THE SAME, AND USES THEREOF

CROSS REFERENCE TO RELATED APPLICATIONS

This application claims priority to and benefit of U.S. Provisional Patent Application Ser. No. 63/347,647, titled "CLAUDIN 18.2 ANTIBODIES, METHODS OF MAKING THE SAME, AND USES THEREOF" and filed one Jun. 1, 2022, which is hereby incorporated by reference herein in its entirety.

CROSS REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Jun. 1, 2023, is named "ITL-020US sequence listing.XML" and is 32,768 bytes in size.

BACKGROUND

Gastric tumors are frequently diagnosed and treated in advanced tumor stages with poor prognosis. Recent studies have identified isoform 2 of the tight junction protein claudin-18 ("Claudin 18.2") as a promising target in therapies for gastric tumors. Claudin 18.2 is expressed in gastric tumors but is not expressed in normal adult tissues, with the exception of the gastric mucosa. Thus, the relatively specific expression of Claudin 18.2 to gastric tumors makes Claudin 18.2 an attractive target. Specifically targeting Claudin 18.2 is difficult because of its high similarity to Claudin 18.1. Additionally, it is a structurally complex antigen, making it difficult to raise antibodies against the target. Therefore, there is a need in the art for antibodies against Claudin 18.2 that can be used in different therapeutic modalities. The embodiments provided herein satisfy these needs as well as others.

SUMMARY

In some embodiments, a recombinant antibody, or antigen binding fragment thereof, that binds to a Claudin 18.2 protein, is provided. In some embodiments, the recombinant antibody, or antigen binding fragment thereof, binds to a Claudin 18.2 protein in its native conformation. In some embodiments, the antibody, or antigen binding fragment thereof, specifically binds to Claudin 18.2. In some embodiments, the antibody, or antigen binding fragment thereof, does not specifically bind to Claudin 18.1.

In some embodiments, the antibody, or antigen binding fragment thereof, binds to a human Claudin 18.2 protein. In some embodiments, the antibody, or antigen binding fragment thereof, that binds to a Claudin 18.2 protein, is a humanized antibody. In some embodiments, the antibody, or antigen binding fragment thereof, that binds to a Claudin 18.2 protein, is a chicken antibody. In some embodiments, the antibody, or antigen fragment thereof, is generated by inducing an immune response against Claudin 18.2 in a chicken.

In some embodiments, the antibody, or antigen binding fragment thereof, that binds to a Claudin 18.2 protein, is a monoclonal antibody. In some embodiments, the antibody, or antigen binding fragment thereof, that binds to a Claudin 18.2 protein, is an scFv antibody.

In some embodiments, the antibody or antigen binding fragment comprises: a light chain variable ($V_L$) region comprising a light chain CDR1 (LCDR1), a light chain CDR2 (LCDR2), and a light chain CDR3 (LCDR3), wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 has an amino acid sequence of SEQ ID NO: 19. In some embodiments, the antibody, or antigen binding fragment thereof, comprises a $V_L$ region comprising a LCDR1, a LCDR2, and a LCDR3, wherein the LCDR1 has an amino acid sequence SEQ ID NO: 17; the LCDR2 has an amino acid sequence of SEQ ID NO: 18; and the LCDR3 has an amino acid sequence of SEQ ID NO: 19. In some embodiments, the antibody, or antigen binding fragment thereof, comprises a $V_L$ region comprising a LCDR1, a LCDR2, and a LCDR3, wherein the antibody, or antigen binding fragment thereof, wherein the LCDR1 having an amino acid sequence SEQ ID NO: 23; the LCDR2 has an amino acid sequence of SEQ ID NO: 24; and the LCDR3 has an amino acid sequence of SEQ ID NO: 19.

In some embodiments, the antibody, or antigen binding fragment thereof, that binds to a Claudin 18.2 protein, comprises a light chain variable ($V_L$) region having an amino acid sequence that has at least 85% homology to that of SEQ ID NO: 5, SEQ ID NO: 7, SEQ ID NO: 9, SEQ ID NO: 11, or SEQ ID NO: 13. In some embodiments, the antibody, or antigen binding fragment thereof, that binds to a Claudin 18.2 protein, comprises a $V_L$ region having an amino acid sequence that has at least 90%, 91%, 92%, 93%, $_{94}$%, 95%, 96%, 97%, 98%, or 99% homology to that of SEQ ID NO: 5, SEQ ID NO: 7, SEQ ID NO: 9, SEQ ID NO: 11, or SEQ ID NO: 13. In some embodiments, the antibody, or antigen binding fragment thereof, that binds to a Claudin 18.2 protein, comprises a $V_L$ region having an amino acid sequence that has at least 90%, 91%, 92%, 93%, 94%, 95%, 96%, 97%, 98%, or 99% identity to that of SEQ ID NO: 5, SEQ ID NO: 7, SEQ ID NO: 9, SEQ ID NO: 11, or SEQ ID NO: 13. In some embodiments, the antibody, or antigen binding fragment thereof, that binds to a Claudin 18.2 protein, comprises a $V_L$ region having an amino acid sequence of SEQ ID NO: 5, SEQ ID NO: 7, SEQ ID NO: 9, SEQ ID NO: 11, or SEQ ID NO: 13, or any variant thereof having 1-10 substitutions, deletions, or insertions. In some embodiments, the antibody, or antigen binding fragment thereof, that binds to a Claudin 18.2 protein, comprises a $V_L$ region having an amino acid sequence of SEQ ID NO: 5, SEQ ID NO: 7, SEQ ID NO: 9, SEQ ID NO: 11, or SEQ ID NO: 13, or any variant thereof having 1-10 conservative substitutions. In some embodiments, the antibody, or antigen binding fragment thereof, that binds to a Claudin 18.2 protein, comprises a $V_L$ region having an amino acid sequence of SEQ ID NO: 5, SEQ ID NO: 7, SEQ ID NO: 9, SEQ ID NO: 11, or SEQ ID NO: 13.

In some embodiments, the antibody or antigen binding fragment comprises: a heavy chain variable ($V_H$) region comprising a heavy chain CDR1 (HCDR1), a heavy chain CDR2 (HCDR2), and a heavy chain CDR3 (HCDR3), wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 has an amino acid sequence of SEQ ID NO: 22, SEQ ID NO: 27, SEQ ID NO: 30, or SEQ ID NO: 33. In some embodiments, the antibody, or antigen binding fragment thereof, comprises a $V_H$ region comprising a HCDR1, a HCDR2, and a HCDR3, wherein the HCDR1 has an amino acid sequence of SEQ ID NO: 20; the HCDR2 has an amino acid sequence of SEQ ID NO: 21; and the HCDR3 has an amino acid sequence of SEQ ID NO: 22. In some embodiments, the antibody, or antigen binding fragment thereof, comprises a $V_H$ region comprising a HCDR1, a HCDR2, and a HCDR3, wherein the HCDR1 has an amino acid sequence of SEQ ID NO: 25; the HCDR2 has an amino acid sequence of SEQ ID NO: 26; and the HCDR3 has an amino acid sequence of SEQ ID NO: 27. In some embodiments, the antibody, or antigen binding fragment thereof, comprises a $V_H$ region comprising a HCDR1, a HCDR2, and a HCDR3, wherein the HCDR1 has an amino acid sequence of SEQ ID NO: 28; the HCDR2 has an amino acid sequence of SEQ ID NO: 29; and the HCDR3 has an amino acid sequence of SEQ ID NO: 30. In some embodiments, the antibody, or antigen binding fragment thereof, comprises a $V_H$ region comprising a HCDR1, a HCDR2, and a HCDR3, wherein the HCDR1 has an amino acid sequence of SEQ ID NO: 31; the HCDR2 has an amino acid sequence of SEQ ID NO: 32; and the HCDR3 has an amino acid sequence of SEQ ID NO: 33.

In some embodiments, the antibody, or antigen binding fragment thereof, that binds to a Claudin 18.2 protein, comprises a heavy chain variable ($V_H$) region having an amino acid sequence that has at least 85% homology to that of SEQ ID NO: 4, SEQ ID NO: 6, SEQ ID NO: 8, SEQ ID NO: 10, or SEQ ID NO: 12. In some embodiments, the antibody, or antigen binding fragment thereof, that binds to a Claudin 18.2 protein, comprises a $V_H$ region having an amino acid sequence that has at least 90%, 91%, 92%, 93%, 94%, 95%, 96%, 97%, 98%, or 99% homology to that of SEQ ID NO: 4, SEQ ID NO: 6, SEQ ID NO: 8, SEQ ID NO: 10, or SEQ ID NO: 12. In some embodiments, the antibody, or antigen binding fragment thereof, that binds to a Claudin 18.2 protein, comprises a $V_H$ region having an amino acid sequence that has at least 90%, 91%, 92%, 93%, 94%, 95%, 96%, 97%, 98%, or 99% identity to that of SEQ ID NO: 4, SEQ ID NO: 6, SEQ ID NO: 8, SEQ ID NO: 10, or SEQ ID NO: 12. In some embodiments, the antibody, or antigen binding fragment thereof, that binds to a Claudin 18.2 protein, comprises a $V_H$ region having an amino acid sequence of SEQ ID NO: 4, SEQ ID NO: 6, SEQ ID NO: 8, SEQ ID NO: 10, or SEQ ID NO: 12, or any variant thereof having 1-10 substitutions, deletions, or insertions. In some embodiments, the antibody, or antigen binding fragment thereof, that binds to a Claudin 18.2 protein, comprises a $V_H$ region having an amino acid sequence of SEQ ID NO: 4, SEQ ID NO: 6, SEQ ID NO: 8, SEQ ID NO: 10, or SEQ ID NO: 12, or any variant thereof having 1-10 conservative substitutions. In some embodiments, the antibody, or antigen binding fragment thereof, that binds to a Claudin 18.2 protein, comprises a $V_H$ region having an amino acid sequence of SEQ ID NO: 4, SEQ ID NO: 6, SEQ ID NO: 8, SEQ ID NO: 10, or SEQ ID NO: 12.

In some embodiments, the antibody or antigen binding fragment comprises: (i) a $V_L$ region comprising a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence of SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 has an amino acid sequence of SEQ ID NO: 22, SEQ ID NO: 27, SEQ ID NO: 30, or SEQ ID NO: 33.

In some embodiments, the antibody or antigen binding fragment comprises: (i) a $V_L$ region comprising a LCDR1, a LCDR2, and a LCDR3, wherein the LCDR1 has an amino acid sequence SEQ ID NO: 17; the LCDR2 has an amino acid sequence of SEQ ID NO: 18; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 20; the HCDR2 has an amino acid sequence of SEQ ID NO: 21; and the HCDR3 has an amino acid sequence of SEQ ID NO: 22.

In some embodiments, the antibody or antigen binding fragment comprises: (i) a $V_L$ region comprising a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 25; the HCDR2 has an amino acid sequence of SEQ ID NO: 26; and the HCDR3 has an amino acid sequence of SEQ ID NO: 27.

In some embodiments, the antibody or antigen binding fragment comprises: (i) a $V_L$ region comprising a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 28; the HCDR2 has an amino acid sequence of SEQ ID NO: 29; and the HCDR3 has an amino acid sequence of SEQ ID NO: 30.

In some embodiments, the antibody or antigen binding fragment comprises: (i) a $V_L$ region comprising a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 31; the HCDR2 has an amino acid sequence of SEQ ID NO: 32; and the HCDR3 has an amino acid sequence of SEQ ID NO: 33.

In some embodiments, the antibody or antigen binding fragment comprises: (i) a $V_L$ region having an amino acid sequence of SEQ ID NO: 5, or a variant thereof, and (ii) a $V_H$ region having an amino acid sequence of SEQ ID NO: 4, or a variant thereof. In some embodiments, the antibody or antigen binding fragment comprises: (i) a $V_L$ region having an amino acid sequence of SEQ ID NO: 7, or a variant thereof, and (ii) a $V_H$ region having an amino acid sequence of SEQ ID NO: 6, or a variant thereof. In some embodiments, the antibody or antigen binding fragment comprises: (i) a $V_L$ region having an amino acid sequence of SEQ ID NO: 9, or a variant thereof, and (ii) a $V_H$ region having an amino acid sequence of SEQ ID NO: 8, or a variant thereof. In some embodiments, the antibody or antigen binding fragment comprises: (i) a $V_L$ region having an amino acid sequence of SEQ ID NO: 11, or a variant thereof, and (ii) a $V_H$ region having an amino acid sequence of SEQ ID NO: 10, or a variant thereof. In some embodiments, the antibody or antigen binding fragment comprises: (i) a $V_L$ region having an amino acid sequence of SEQ ID NO: 13, or a variant thereof; and (ii) a $V_H$ region having an amino acid sequence of SEQ ID NO: 12, or a variant thereof.

In some embodiments, the antibody, or antigen binding fragment thereof, that binds to a Claudin 18.2 protein, comprises a $V_L$ region and a $V_H$ region that are not linked by a linker. In some embodiments, the antibody, or antigen binding fragment thereof, that binds to a Claudin 18.2 protein, comprises a $V_L$ region and a $V_H$ region that are linked with a peptide linker. In some embodiments, the antibody, or antigen binding fragment thereof, that binds to a Claudin 18.2 protein, comprises a peptide linker comprising a sequence of GQSSRSSGGGGSSGGGGS (SEQ ID NO: 14); $(GGGGS)_n$ (SEQ ID NO: 15) $(GGGGA)_n$ (SEQ ID NO: 16), or any combination thereof, wherein each n is independently 1-5. In some embodiments, the antibody, or antigen binding fragment thereof, that binds to a Claudin 18.2 protein, comprises a peptide linker that does not comprise a sequence of GQSSRSSGGGGSSGGGGS (SEQ ID NO: 14).

In some embodiments, the antibody, or antigen binding fragment thereof, that binds to a Claudin 18.2 protein, additionally comprises at least one additional peptide that binds to a different target protein. In some embodiments, the antibody, or antigen binding fragment thereof, that binds to a Claudin 18.2 protein, additionally comprises at least one additional peptide that binds to a different target protein, wherein the different target protein is CD3 or CD28. In some embodiments, the antibody, or antigen binding fragment thereof, that binds to a Claudin 18.2 protein, additionally comprises at least one additional peptide that binds to a different target protein, wherein the at least one additional peptide is an antibody, or antigen binding fragment thereof.

In some embodiments, the antibody, or antigen binding fragment thereof, binds to residues E56, N153, Y155, M158, and G159 of the Claudin 18.2 protein. In some embodiments, the antibody, or antigen binding fragment thereof, binds to residues V40, E56, N153, Y155, M158, G159, and G160 of the Claudin 18.2 protein.

In some embodiments, a nucleic acid molecule encoding an antibody, or antigen binding fragment thereof, that binds to a Claudin 18.2 protein, as described herein, is provided.

In some embodiments, a vector comprising a nucleic acid molecule encoding an antibody, or antigen binding fragment thereof, that binds to a Claudin 18.2 protein, as described herein, is provided.

In some embodiments, a cell comprising a nucleic acid molecules encoding an antibody, or antigen binding fragment thereof, that binds to a Claudin 18.2 protein, as described herein, is provided. In some embodiments, a cell comprising a vector comprising a nucleic acid molecules encoding an antibody, or antigen binding fragment thereof, that binds to a Claudin 18.2 protein, as described herein, is provided.

In some embodiments, a pharmaceutical composition comprising an antibody, or antigen binding fragment thereof, that binds to a Claudin 18.2 protein, as described herein, is provided.

In some embodiments, a pharmaceutical composition comprising a nucleic acid molecule encoding an antibody, or antigen binding fragment thereof, that binds to a Claudin 18.2 protein, as described herein, is provided. In some embodiments, a pharmaceutical composition comprising a vector comprising a nucleic acid molecule encoding an antibody, or antigen binding fragment thereof, that binds to a Claudin 18.2 protein, as described herein, is provided.

In some embodiments, the pharmaceutical composition is an injectable pharmaceutical composition. In some embodiments, the pharmaceutical composition is sterile or pyrogen free. In some embodiments, the pharmaceutical composition is free of antibodies, or antigen binding fragments thereof, that do not bind to Claudin 18.2.

In some embodiments, a method of treating a subject with a tumor or gastric tumor is provided, the method comprising administering to a subject a therapeutically effective amount of a Claudin 18.2 antibody, or antigen binding fragment thereof, as described herein. In some embodiments, a method of treating a subject with a tumor or gastric tumor is provided, the method comprising administering to a subject a therapeutically effective amount of a pharmaceutical composition comprising a Claudin 18.2 antibody, or antigen binding fragment thereof, as described herein. In some embodiments, the tumor or gastric tumor is gastric adenocarcinoma, gastroesophageal junction adenocarcinoma, pancreatic adenocarcinoma, or non-small cell lung cancer. In some embodiments, the subject is a human, a mouse, a sheep, a rat, a rabbit, a shark, a llama, or a chicken.

In some embodiments, a method of detecting the presence or absence of Claudin 18.2 in a sample is provided, the method comprising contacting the sample with an antibody, or antigen binding fragment thereof, that binds to Claudin 18.2, as described herein, and detecting the binding to a Claudin 18.2 antigen by the antibody, or antigen binding fragment thereof, wherein the detection of the binding indicates the presence Claudin 18.2; or the absence of the detection of the binding to the Claudin 18.2 indicates the absence of the Claudin 18.2.

In some embodiments, a method of inducing an immune response against a Claudin 18.2 protein in a subject is provided, the method comprising administering a virus-like particle comprising a Claudin 18.2 protein to the subject under conditions sufficient to induce an immune response. In some embodiments, the subject is a human, a mouse, a sheep, a rat, a rabbit, a shark, a llama, or a chicken.

In some embodiments, a method of generating an antibody, or antigen binding fragment thereof, that binds to a Claudin 18.2 protein, is provided. In some embodiments, the method of generating an antibody, or antigen binding fragment thereof, that binds to a Claudin 18.2 protein, comprises administering a virus-like particle comprising the Claudin 18.2 protein on its surface to a subject under conditions to induce an immune response against the Claudin 18.2 protein. In some embodiments, the subject is a human, a mouse, a sheep, a rat, a rabbit, a shark, a llama, or a chicken.

In some embodiments, the method of generating an antibody, or antigen binding fragment thereof, that binds to a Claudin 18.2 protein, further comprises isolating the antibody that binds to the Claudin 18.2 protein. In some embodiments, the antibody, or antigen binding fragment thereof, that is generated binds to an extracellular domain of the Claudin 18.2 protein. In some embodiments, the method of generating an antibody, or antigen binding fragment thereof, that binds to a Claudin 18.2 protein, further comprises generating a virus-like particle comprising the Claudin 18.2 protein. In some embodiments, the method of generating an antibody, or antigen binding fragment thereof, that binds to a Claudin 18.2 protein, further comprises transfecting or transducing a cell with a Claudin 18.2 protein and a retroviral gag protein under conditions sufficient to produce a virus-like particle comprising the Claudin 18.2 protein. In some embodiments, the cell is a HEK-293T cell. In some embodiments, the gag protein is a MLV gag protein. In some embodiments, the retroviral gag protein is Murine Leukemia Virus (MLV), gag, HIV gag, or RSV gag protein.

In some embodiments, a method of modulating Claudin 18.2 activity is provided. In some embodiments, the method of modulating Claudin 18.2 activity comprises contacting a cell expressing Claudin 18.2 with a Claudin 18.2 antibody, or antigen binding fragment thereof, that binds to Claudin 18.2 on the cell surface. In some embodiments, the method of modulating Claudin 18.2 activity comprises contacting a cell expressing Claudin 18.2 with a pharmaceutical composition comprising a Claudin 18.2 antibody, or antigen binding fragment thereof, that binds to Claudin 18.2 on the cell surface. In some embodiments, the method of modulating Claudin 18.2 activity comprises administering to a subject an antibody, or antigen binding fragment thereof, that binds to Claudin 18.2 protein, as provided for herein. In some embodiments, the method of modulating Claudin 18.2 activity comprises administering to a subject a pharmaceutical composition comprising an antibody, or antigen binding fragment thereof, that binds to Claudin 18.2 protein, as provided for herein.

In some embodiments, a chimeric antigen receptor is provided, wherein the chimeric antigen receptor comprises an extracellular portion comprising an antibody or, antigen binding fragment thereof, that binds to Claudin 18.2, as provided herein. In some embodiments, chimeric antigen receptor comprises an extracellular portion comprising an antibody or, antigen binding fragment thereof, that binds to Claudin 18.2, as provided herein, wherein the antibody or, antigen binding fragment thereof, comprises a binding domain, and wherein the binding domain is a scFv fragment.

In some embodiments, a multi-specific molecule is provided, wherein the multi-specific molecule comprises a first portion or domain that binds to a Claudin 18.2 protein, and a second portion or domain that binds to a second molecule. In some embodiments, the multi-specific molecule has a therapeutic effect on cells that express Claudin 18.2. In some embodiments, the first portion or domain that binds to Claudin 18.2 is an antibody or binding fragment thereof, as provided for herein. In some embodiments, the first portion or domain that binds to Claudin 18.2 is an antibody or binding fragment thereof, as provided for herein, comprising a binding domain, wherein the binding domain is an scFv fragment.

BRIEF DESCRIPTION OF THE DRAWINGS

FIG. 1 also illustrates a positive control, which is labeled as "Clinical Benchmark."

DETAILED DESCRIPTION

Figure 1:
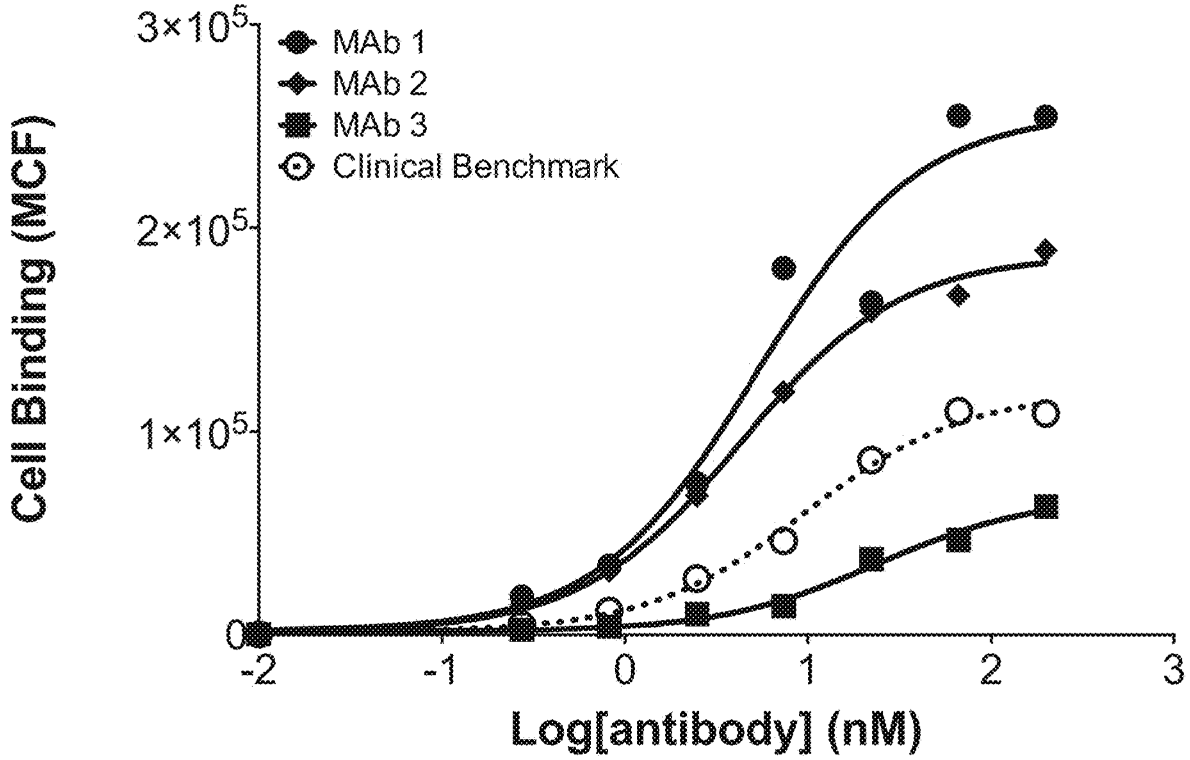
FIG. 1 illustrates the binding of three humanized antibodies MAb1 (IM-44-09B03-1H1B), MAb2 (IM-44-01E10-1HA), and MAb3 (IM-44-05H06-1HD) against Claudin 18.2 to cells expressing Claudin 18.2.

Provided herein are antibodies, or antigen binding fragments thereof, that bind to a Claudin 18.2 protein. In some embodiments, the antibodies, or antigen binding fragments thereof, that bind to Claudin 18.2, are isolated. In some embodiments, the antibodies, or antigen binding fragments thereof, that bind to Claudin 18.2, are recombinant. In some embodiments, the antibodies, or antigen binding fragments thereof, are conformational MAbs (monoclonal antibodies) that recognize Claudin 18.2 in its native environment or native structure. Without being bound to any particular theory, a Claudin 18.2 protein in its native environment or native structure, refers to a Claudin 18.2 protein that is in a plasma membrane (cell membrane) or in a bi-layer structure. The native structure of a Claudin 18.2 protein in its native environment can be folded such that the Claudin 18.2 protein spans the plasma membrane or lipid bilayer more than once. Accordingly, an antibody, or antigen binding fragment thereof, that binds to a Claudin 18.2 protein in its native environment or native structure refers to an antibody, or antigen binding fragment thereof, that binds to a Claudin 18.2 protein that is in a plasma membrane (cell membrane) or in a bi-layer structure. In some embodiments, the antibodies, or antigen binding fragments thereof, that bind to Claudin 18.2, are specific for Claudin 18.2 and do not cross react with Claudin 18.1 or significantly cross react with Claudin 18.1. Accordingly, the present disclosure provides surprising and unexpected results, which are, in part, antibodies that can bind to Claudin 18.2 in its native structure and/or its native environment without cross-reacting with Claudin 18.1. In some embodiments, the antibodies, or antigen binding fragments thereof, that bind to Claudin 18.2, inhibit the activity of Claudin 18.2. In some embodiments, the antibodies, or antigen binding fragments thereof, that bind to Claudin 18.2, recognize conformational epitopes on native Claudin 18.2 present in intact human cells. In some embodiments, the antibodies, or antigen binding fragments thereof, that bind to a Claudin 18.2 protein, demonstrate remarkable specificity within the Claudin family, reacting with a mouse ortholog but not most other members of the human membrane proteome. In some embodiments, the antibodies, or antigen binding fragments thereof, that bind to a Claudin 18.2 protein, are the MAbs MAb1 (IM-44-09B03-11HB), MAb2 (IM-44-01E10-1HA), or MAb3 (IM-44-05H06-1HD).

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody. In some embodiments, the antibody, or antigen binding fragment thereof, that binds to a Claudin 18.2 protein, is a monoclonal antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', $F(ab')_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')2 molecule.

A "F(ab')2 fragment" contains two light chains and two heavy chains containing a portion of the constant region between the $C_H1$ and $C_H2$ domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) The Pharmacology of Monoclonal Antibodies, vol. 113, Rosenburg and Moore eds. Springer-Verlag, New York, pp. 269-315. See also, International Patent Application Publication No. WO 88/01649 and U.S. Pat. Nos. 4,946,778 and 5,260,203. In some embodiments, the antibody, or antigen binding fragment thereof, that binds to a Claudin 18.2 protein, is an scFv antibody.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies as described herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present disclosure provides single domain antibodies comprising two $V_H$ domains with modifications such that single domain antibodies are formed.

As used herein, the term "diabodies" refers to small antibody fragments with two antigen binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

Typically, a variant antibody, or antigen binding fragment of the antibody, as provided herein, retains at least 10% of its Claudin 18.2 binding activity (when compared to a parental antibody that is modified) when that activity is expressed on a molar basis. In some embodiments, a variant antibody (or antigen fragment thereof), or antigen binding fragment of an antibody provided herein, retains at least 20%, 50%, 70%, 80%, 90%, 95% or 100% or more of the Claudin 18.2 binding affinity as the parental antibody. As described herein. It is also intended that an antibody, or antigen binding fragment thereof, of the present disclosure can include conservative or non-conservative amino acid substitutions, which can also be referred to as "conservative variants" or "function conserved variants" of the antibody, which do not substantially alter its biologic activity.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) *Proc. Natl. Acad. Sci. USA* 81: 6851-6855). Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc). In some embodiments, the antibody, or antigen binding fragment thereof, that binds to a Claudin 18.2 protein, is a humanized antibody.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only. In some embodiments, the antibody, or antigen binding fragment thereof, binds to a human Claudin 18.2 protein. In some embodiments, the antibody, or antigen binding fragment thereof, that binds to a Claudin 18.2 protein, is a chicken antibody. In some embodiments, the antibody, or antigen fragment thereof, is generated by inducing an immune response against Claudin 18.2 in a chicken.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition.

The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody, or antigen binding fragment thereof, that are responsible for antigen binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) J. Mol. Biol. 196: 901-917). As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

The term "chicken antibody" refers to an antibody that was raised in a chicken. For example, a protein of interest can be introduced into a chicken, such as in a VLP as provided for herein, to stimulate an immune response against the protein of interest to produce antibodies in the chicken. The antibody can then be humanized or otherwise modified as desired.

Additionally, in some embodiments, the antibodies, or antigen binding fragments thereof, can take the form of a full length antibody, single-domain antibody, a recombinant heavy-chain-only antibody (VHC), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a F(ab')2, a peptide mimetic molecule, or a synthetic molecule, as described in U.S. Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of each of which are hereby incorporated by reference in their entireties. See also, Storz MAbs. 2011 May-June; 3(3): 310-317, which is hereby incorporated by reference.

The term "antigen" as used herein means any molecule that has the ability to generate antibodies either directly or indirectly. Included within the definition of "antigen" is a protein-encoding nucleic acid. An "antigen" can also refer to the binding partner of an antibody. In some embodiments, the antigen is the Claudin 18.2 protein expressed on the surface of a cell or particle, such a virus-like particle. In some embodiments, the cell is an intact cell. An intact cell is a cell that has not been lysed or broken open with the use of detergents or other reagents. A cell that has been treated with detergents or other reagents that breaks up the cellular membrane or punches holes in a cellular membrane is not an intact cell. By expressing the receptor on the surface of the cell or particle, e.g. lipoparticle, the receptor can present conformational epitopes that may otherwise not be present if purified protein is used. An example is provided herein. In some embodiments, an adjuvant is not used, but an adjuvant can be used. In some embodiments, the particles are injected into a bird (e.g. chicken) to stimulate an immune response and generate antibodies against the protein present on the surface of the particle. Particles suitable for the generation of antibodies, and methods of making the same, are described, for example, in U.S. Pat. Nos. 8,377,691, 7,763, 258, 8,158,130 and U.S. Patent Application Publication Nos. 20050123563 and 20120195882, each of which is hereby incorporated by reference. These publications and patents describe the generation of various particles, including lipoparticles, that can be used to express membrane spanning proteins (e.g. multiple-membrane spanning proteins, ion channels, and the like). Claudin 18.2 can, in some embodiments, be incorporated, into the lipoparticles according to these methods or as provided for herein.

For example, methods are provided herein for generating an antibody, or antigen binding fragment thereof, that binds to a Claudin 18.2 protein, the methods comprising administering a virus-like particle comprising the Claudin 18.2 protein on its surface to a subject under conditions to induce an immune response against the Claudin 18.2 protein to generate the antibody, or antigen binding fragment thereof, that binds to the Claudin 18.2 protein. In some embodiments, a nucleic acid molecule encoding the Claudin 18.2 protein is provided.

In some embodiments, the methods further comprise isolating the antibody, or antigen binding fragment thereof, that binds to the Claudin 18.2 protein. In some embodiments, the subject is a human, a mouse, sheep, a rat, a rabbit, a shark, a llama, or a chicken. In some embodiments, the antibody, or antigen binding fragment thereof, that is generated binds to an extracellular domain of the Claudin 18.2 protein. In some embodiments, the method comprises generating a virus-like particle comprising the Claudin 18.2 protein, the method comprising transfecting or transducing a cell with Claudin 18.2 protein and a gag protein under conditions sufficient to produce the virus-like particle comprising the Claudin 18.2 protein. The VLPs can be generated as described herein and in the references above. In some embodiments, the cell is a HEK-293T cell. In some embodiments, the gag protein is a retroviral gag protein. In some embodiments, the retroviral gag protein is Murine Leukemia Virus (MLV) gag protein. In some embodiments, the Gag is HIV. In some embodiments, the Gag is rous sarcoma virus Gag.

As used herein, "specific binding" or "immunospecific binding" or "binds immunospecifically" refer to an antibody, or an antibody fragment, binding to a predetermined antigen (e.g. Claudin 18.2) or epitope present on the antigen. In some embodiments, the antibody, or antigen binding fragment thereof, binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody recognizing Claudin 18.2" and "an antibody specific for Claudin 18.2" are used interchangeably herein with the term "an antibody which binds immunospecifically to Claudin 18.2." Reference in the present disclosure may be made to Claudin 18.2. In some embodiments, the antibody, or antigen binding fragment thereof, binds specifically to Claudin 18.2 over other proteins, such as, but not limited to Claudin 18.1. The degree of specificity necessary for an anti-Claudin 18.2 antibody, or antigen binding fragment thereof, may depend on the intended use of the antibody, and at any rate is defined by its suitability for use for an intended purpose. In some embodiments, the antibody, or binding compound derived from the antigen binding site of an antibody, of the contemplated method binds to its antigen (Claudin 18.2), with an affinity that is at least two fold greater, at least ten times greater, at least 20-times greater, or at least 100-times greater than the affinity with any other antigen.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The term "homolog" means protein sequences having between 40% and 100% sequence homology or identity to a reference sequence. Percent identity between two peptide chains can be determined by pair wise alignment using the default settings of the AlignX module of Vector NTI v.9.0.0 (Invitrogen Corp., Carslbad, Calif.). In some embodiments, the antibody, or antigenic binding fragment thereof has, at least 50, 60, 70, 80, 90, 91, 92, 93, 94, 95, 96, 97, 98, or 99% homology or identity to a sequence described herein. In some embodiments, the antibody, or antigen binding fragment thereof, has conservative substitutions as compared to a sequence described herein. Exemplary conservative substitutions are illustrated in Table 1 and are encompassed within the scope of the disclosed subject matter. The conservative substitution may reside in the framework regions, or in antigen binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE

Exemplary Conservative Substitutions:

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. As described herein, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

The term "in combination with" as used herein means that the described agents can be administered to an animal or subject together in a mixture, concurrently as single agents or sequentially as single agents in any order.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in human, a mouse, sheep, a rat, a rabbit, a shark, a llama, or a chicken. In some embodiments, the antibody, or antigen binding fragment thereof, is produced in a chicken. The antibodies can also be produced in or other small animals.

The term "epitope" is meant to refer to that portion of any molecule capable of being recognized by and bound by an antibody, or antigen binding fragment thereof, at one or more antigen binding regions. Epitopes usually consist of chemically active surface groupings of molecules such as amino acids or sugar side chains and have specific three dimensional structural characteristics as well as specific charge characteristics. Example of epitopes include, but are not limited to, the residues described herein that form Claudin 18.2 epitopes. In some embodiments, the epitope is only present in a non-denatured protein. In some embodiments, the epitope is only present in a denatured protein.

In some embodiments, the source for the DNA encoding a non-human antibody, or antigen binding fragment thereof, includes cell lines which produce antibodies, such as hybrid cell lines commonly known as hybridomas.

The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC CRL1581) and the myeloma P3X63Ag8 (ATCC TIB9), or its derivatives. See, e.g., Ausubel infra, Harlow infra, and Colligan infra, the contents of which references are incorporated entirely herein by reference.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Visquez M, Kumar S. (2004); and "Humanization of a chicken anti-IL-12 monoclonal antibody" Immunol Methods 295 (1-2): 9-19; Nishibori N, Horiuchi H, Furusawa S, Matsuda H. (2006) "Humanization of chicken monoclonal antibody using phage display system" Mol Immunol. 43 (6): 634-42, each of which is incorporated by reference in its entirety.

The antibody-producing cell contributing the nucleotide sequences encoding the antigen binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g., Ausubel infra, Harlow infra, and Colligan infra, the contents of which references are incorporated entirely herein by reference. The cell fusions are accomplished by standard procedures well known to those skilled in the field of immunology.

Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

In some embodiments, the antibody, or antigen binding fragment thereof, is a MAb which binds to Claudin 18.2. In some embodiments, the antibody, or antigen binding fragment thereof, binds to amino acids of an epitope of the Claudin 18.2.

In some embodiments, the antibody, or antigen binding fragment thereof, comprises a sequence as provided for herein.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind to Claudin 18.2. This can be in the form of an antibody drug conjugate ("ADC"), a multi-specific molecule, or a chimeric antigen receptor. The CDRs and antibody sequences provided herein also be humanized or made fully human according to known methods. The sequences can also be made into chimeric antibodies as described herein.

In some embodiments, the antibody, or antigen binding fragment thereof, comprises an amino acid sequence comprising a sequence provided for herein or a fragment thereof. In some embodiments, the antibody, or antigen binding fragment thereof, comprises one or more amino acid sequences as provided herein, an antigen binding fragments thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid encoding an antibody, or antigen binding fragment thereof, is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, "derivatives" of the antibodies, antibody fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The antibody fragments and derivatives can be produced in any manner.

The identification of these antigen binding region and/or epitopes recognized by Abs described herein provide the information necessary to generate additional monoclonal antibodies with similar binding characteristics and therapeutic or diagnostic utility that parallel the embodiments of this application.

The nucleic acid sequence encoding an antibody, or antigen binding fragment thereof, described herein can be genomic DNA or cDNA, or RNA (e.g. mRNA) which encodes at least one of the variable regions described herein. A convenient alternative to the use of chromosomal gene fragments as the source of DNA encoding the V region antigen binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen binding segment able to detect, bind, to or neutralize a Claudin 18.2 antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody or antibody fragment. Such "codon usage rules" are disclosed by Lathe, et al., J. Molec. Biol. 183:1 12 (1985). Using the "codon usage rules" of Lathe, a single oligonucleotide, or a set of oligonucleotides, which contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, antibody fragments, and regions can be derived from a human fetal liver library, by known methods. Human C regions genes can be derived from any human cell including those which express and produce human immunoglobulins. The human $C_H$ region can be derived from any of the known classes or isotypes of human H chains, including gamma, p, a, 6 or 8, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or μ (IgM). The human $C_L$ region can be derived from either human L chain isotype, kappa or lambda. In some embodiments, the antibody, or antigen binding fragment thereof, comprises a Fc domain. In some embodiments, the Fc domain comprises a mutation to extend the half-life of the antibody. In some embodiments, the Fc domain comprises a mutation such as those described in U.S. Pat. No. 7,670,600, which is hereby incorporated by reference in its entirety. In some embodiment, the constant region comprises a mutation at position at amino acid residue 428 relative to a wild-type human IgG constant domain, numbered according to the EU numbering index of Kabat. Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody, or antigen binding fragment thereof, further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

Genes encoding human immunoglobulin C regions can be obtained from human cells by standard cloning techniques (Sambrook, et al. (Molecular Cloning: A Laboratory Manual, 2$^{nd}$ Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as $F(ab')_2$ and Fab, can be prepared by designing a chimeric H chain gene which is appropriately truncated. For example, a chimeric gene encoding an H chain portion of an $F(ab')_2$ fragment would include DNA sequences encoding the $CH_1$ domain and hinge region of the H chain, followed by a translational stop codon to yield the truncated molecule.

In some embodiments, the antibodies, murine, human, humanized, or chimeric antibodies, antibody fragments, and regions of the antibodies described herein are produced by cloning DNA segments encoding the H and L chain antigen binding regions of a Claudin 18.2 antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen binding region of non-human origin, such as a functionally rearranged V region with joining (J) segment, linked to a second DNA segment encoding at least a part of a human C region.

Therefore, cDNA encoding the antibody V and C regions, the method of producing the antibody according to some of the embodiments described herein involve several steps, as exemplified below: 1. isolation of messenger RNA (mRNA) from the cell line producing an anti-Claudin 18.2 antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

As used herein and unless otherwise indicated, the term "about" is intended to mean±5% of the value it modifies. Thus, about 100 means 95 to 105.

In some embodiments, the antibodies, or antigen binding fragments thereof, described herein are used to detect the presence of the antigen. The present antibody, or antigen binding fragment thereof, can be used in any device or method to detect the presence of the antigen.

The term "purified" with referenced to an antibody, or antigen binding fragment thereof, refers to an antibody, or antigen binding fragment thereof, that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody, or antigen binding fragment thereof, is purified.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

The antibodies provided for herein may also be conjugated to a chemical moiety.

The chemical moiety may be, inter alia, a polymer, a radionuclide or a cytotoxic factor. In some embodiments, this can be referred to as a antibody drug conjugate. In some embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)). Examples of chemical moieties include, but are not limited to, anti-mitotics, such as calicheamicins (e.g. ozogamicin), monomethyl auristatin E, mertansine, and the like. Other examples include, but are not limited to, biologically active anti-microtubule agents, alkylating agents and DNA minor groove binding agents. Other examples of are provided herein and below. The chemical moiety can be linked to the antibody through a linking group (maleimide), a cleavable linker, such as a cathepsin cleavable linkers (valine-citrulline), and in some embodiments, one or more spacers (e.g. para-aminobenzylcarbamate). Without being bound to any particular theory, once the antibody conjugate binds Claudin 18.2 it can be internalized and the chemical moiety can kill the cell or otherwise inhibit its growth. In some embodiments, the cell is a gastric tumor cell.

The antibodies and antibody fragments of the present disclosure may also be conjugated with labels such as $^{99}$Tc, $^{90}$Y, $^{111}$In, $^{32}$P, $^{14}$C, $^{125}$I, $^{3}$H, $^{131}$L, $^{11}$C, $^{15}$O, $^{13}$N, $^{18}$F, $^{35}$, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{5}$Tr and $^{56}$Fe.

The antibodies and antibody fragments may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody or antibody fragment molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibody or antibody molecules of the present disclosure to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

The antibodies provided herein can also be incorporated into a chimeric antigen receptor ("CAR") that can be used, for example, in a CAR-T cell. In some embodiments, the extracellular domain of the CAR can be an antibody, or antigen binding fragment thereof, as provided for herein. In some embodiments, the antibody, or antigen binding fragment thereof, is in a scFv format. CAR-T cells are a type of treatment in which a patient's T cells are modified so they will attack cancer cells. T cells are taken from a patient's blood. Then the gene for a special receptor that binds to a certain protein on the patient's cancer cells is added in the laboratory. In some embodiments, the receptor binds to Claudin 18.2 using the binding regions of the antibodies provided for herein. The CAR-T cells comprising the Claudin 18.2 antibody, or antigen binding fragment thereof, can then be used to treat a tumor or gastric tumors, such as those described herein.

As used herein, the term "recombinant antibody" refers to an antibody that is not naturally occurring. In some embodiments, the term "recombinant antibody" refers to an antibody that is not isolated from a human subject.

In some embodiments, an antibody (e.g. an anti-Claudin 18.2 antibody), or antigen binding fragment thereof, is provided herein. In some embodiments, the antibody, or antigen binding fragment thereof, is a recombinant antibody that binds to a Claudin 18.2 protein. In some embodiments, the antibody, or antigen binding fragment thereof, that binds to a Claudin 18.2 protein, is a monoclonal antibody. In some embodiments, the antibody, or antigen binding fragment thereof, that binds to a Claudin 18.2 protein, is a humanized antibody. In some embodiments, the antibody, or antigen binding fragment thereof, that binds to a Claudin 18.2 protein, is a chicken antibody. In some embodiments, the antibody, or antigen fragment thereof, is generated by inducing an immune response against Claudin 18.2 in a chicken. In some embodiments, the antibody, or antigen binding fragment thereof, that binds to a Claudin 18.2 protein, is an scFv antibody.

In some embodiments, the antibody, or antigen binding fragment thereof, binds to a human Claudin 18.2 protein. In some embodiments, the antibody, or antigen binding fragment thereof, recognizes a Claudin 18.2 protein that in its native (non-denatured) conformation. In some embodiments, the antibody, or antigen binding fragment thereof, does not specifically binds to a denatured Claudin 18.2 protein. In some embodiments, antibody, or antigen binding fragment thereof, binds to a Claudin 18.2 protein comprising an amino acid sequence of SEQ ID NO: 1, SEQ ID NO: 2, or SEQ ID NO: 3.

| | |
|---|---|
| Claudin 18.2 (human); SEQ ID NO: 1 | MAVTACQGLGFVVSLIGIAGIIAATCMDQWSTQDLYNN PVTAVFNYQGLWRSCVRESSGFTECRGYFTLLGLPAML QAVRALMIVGIVLGAIGLLVSIFALKCIRIGSMEDSAK ANMTLTSGIMFIVSGLCAIAGVSVFANMLVTNFWMSTA NMYTGMGGMVQTVQTRYTFGAALFVGWVAGGLTLIGGV MMCIACRGLAPEETNYKAVSYHASGHSVAYKPGGFKAS TGFGSNTKNKKIYDGGARTEDEVQSYPSKHDYV |
| Claudin 18.2 (cyno-molgus); SEQ ID NO: 2 | MAVTACQGLGFVVSLIGIAGIIAATCMDQWSTQDLYNN PVTAVFNYQGLWRSCVRESSGFTECRGYFTLLGLPAML QAVRALMIVGIVLGAIGLLVSIFALKCIRIGSMEDSAK ANMTLTSGIMFIVSGLCAIAGVSVFANMLVTNFWMSTA NMYTGMGGMVQTVQTRYTFGAALFVGWVAGGLTLIGGV MMCIACRGLAPEETNYKAVSYHASGHSVAYKPGGFKAS TGFGSNTKNKKTYDGGAHTEDELQSYPSKHDYV |
| Claudin 18.2 (mouse); SEQ ID NO: 3 | MSVTACQGLGFVVSLIGFAGIIAATCMDQWSTQDLYNN PVTAVFNYQGLWRSCVRESSGFTECRGYFTLLGLPAML QAVRALMIVGIVLGVIGILVSIFALKCIRIGSMDDSAK AKMTLTSGILFIISGICAIIGVSVFANMLVTNFWMSTA NMYSGMGGMGGMVQTVQTRYTFGAALFVGWVAGGLTLI GGVMMCIACRGLTPDDSNFKAVSYHASGONVAYRPGGF KASTGFGSNTRNKKIYDGGARTEDDEQSHPTKYDYV |

In some embodiments, the antibody, or antigen binding fragment thereof, does not specifically bind to Claudin 18.1.

In some embodiments, the antibody, or antigen binding fragment thereof, comprises a peptide having an amino acid sequence of selected from the following table.

| Ab ID No | LCDR1 | LCDR2 | LCDR3 | HCDR1 | HCDR2 | HCDR3 |
|---|---|---|---|---|---|---|
| MAb1 | SGGYNGHYG (SEQ ID NO: 23) | SNNQRPS (SEQ ID NO: 24) | GGYDSSAGI (SEQ ID NO: 19) | SYGMG (SEQ ID NO: 28) | AITRDSSTNYGAAVKG (SEQ ID NO: 29) | DASNGYCWYTGRGSYSCGAHHIDA (SEQ ID NO: 30) |
| MAb2 | SGGSGSYGYYG (SEQ ID NO: 17) | GTNKRPS (SEQ ID NO: 18) | GGYDSSAGI (SEQ ID NO: 19) | SYGMS (SEQ ID NO: 20) | GIGSSGSDTWYADSVKG (SEQ ID NO: 21) | DATNGYCWYTGRGSYSCGAHHIDA (SEQ ID NO: 22) |

-continued

| Ab ID No | LCDR1 | LCDR2 | LCDR3 | HCDR1 | HCDR2 | HCDR3 |
|---|---|---|---|---|---|---|
| MAb3 | SGGYNGHYG (SEQ ID NO: 23) | SNNQRPS (SEQ ID NO: 24) | GGYDSSAGI (SEQ ID NO: 19) | SYAMM (SEQ ID NO: 25) | EISSTGGSTYYGSAVKG (SEQ ID NO: 26) | STYGATWKSADSIDA (SEQ ID NO: 27) |
| MAb4 | SGGYNGHYG (SEQ ID NO: 23) | SNNQRPS (SEQ ID NO: 24) | GGYDSSAGI (SEQ ID NO: 19) | SYAMM (SEQ ID NO: 25) | EISSTGGSTYYGSAVKG (SEQ ID NO: 26) | STYGATWKSADSIDA (SEQ ID NO: 27) |
| MAb5 | SGGYNGHYG (SEQ ID NO: 23) | SNNORPS (SEQ ID NO: 24) | GGYDSSAGI (SEQ ID NO: 19) | DYGMG (SEQ ID NO: 31) | AITIDGSTYYGTAVKG (SEQ ID NO: 32) | DANNGYCWYTGRGSYSCGAHNIDA (SEQ ID NO: 33) |

In some embodiments, the antibody or antigen binding fragment comprises a light chain comprising a light chain CDR1 (LCDR1), a light chain CDR2 (LCDR2), and a light chain CDR3 (LCDR3). In some embodiments, the antibody or antigen binding fragment comprises a light chain variable ($V_L$) region comprising a LCDR1, a LCDR2, and a LCDR3. In some embodiments, the antibody or antigen binding fragment comprises a light chain comprising a light chain variable ($V_L$) region comprising a LCDR1, a LCDR2, and a LCDR3.

In some embodiments, the antibody or antigen binding fragment comprises a heavy chain comprising a heavy chain CDR1 (HCDR1), a heavy chain CDR2 (HCDR2), and a heavy chain CDR3 (HCDR3). In some embodiments, the antibody or antigen binding fragment comprises a heavy chain variable ($V_H$) region comprising a HCDR1, a HCDR2, and a HCDR3.

In some embodiments, the antibody or antigen binding fragment comprises a heavy chain comprising a heavy chain variable ($V_H$) region comprising a HCDR1, a HCDR2, and a HCDR3.

In some embodiments, the antibody, or antigen binding fragment thereof, comprises a light chain CDR or a heavy chain CDR having an amino acid sequence of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33.

The different CDR motifs can be combined in any combination including those not depicted in the table above. For example, the following embodiments are provided as non-limiting examples of such combinations.

In some embodiments, the antibody, or antigen binding fragment thereof, comprises a light chain CDR having a sequence of SEQ ID NO: 17, SEQ ID NO: 18, SEQ ID NO: 19, SEQ ID NO: 23, or SEQ ID NO: 24. In some embodiments, the antibody or antigen binding fragment comprises: a light chain variable ($V_L$) region comprising a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, comprises a heavy chain CDR having a sequence of SEQ ID NO: 20, SEQ ID NO: 21, SEQ ID NO: 22, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33. In some embodiments, the antibody or antigen binding fragment comprises: a heavy chain variable ($V_H$) region comprising a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, comprises a light chain having a LCDR1, a LCDR2, and a LCDR3, wherein the LCDR1 has a sequence of SEQ ID NO: 17, the LCDR2 has a sequence of SEQ ID NO: 18, and the LCDR3 has a sequence of SEQ ID NO: 19.

In some embodiments, the antibody, or antigen binding fragment thereof, comprises a light chain having a LCDR1, a LCDR2, and a LCDR3, wherein the LCDR1 has a sequence of SEQ ID NO: 17, the LCDR2 has a sequence of SEQ ID NO: 24, and the LCDR3 has a sequence of SEQ ID NO: 19.

In some embodiments, the antibody, or antigen binding fragment thereof, comprises a light chain having a LCDR1, a LCDR2, and a LCDR3, wherein the LCDR1 has a sequence of SEQ ID NO: 23, the LCDR2 has a sequence of SEQ ID NO: 18, and the LCDR3 has a sequence of SEQ ID NO: 19.

In some embodiments, the antibody, or antigen binding fragment thereof, comprises a light chain having a LCDR1, a LCDR2, and a LCDR3, wherein the LCDR1 has a sequence of SEQ ID NO: 23, the LCDR2 has a sequence of SEQ ID NO: 24, and the LCDR3 has a sequence of SEQ ID NO: 19.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 21, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 21, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 21, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 21, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 26, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 26, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 26, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 26, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 29, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 29, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 29, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 29, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 32, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 32, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 32, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 20, the HCDR2 has a sequence of SEQ ID NO: 32, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 21, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 21, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 21, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 21, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 26, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 26, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 26, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 26, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 29, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 29, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 29, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 29, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 32, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 32, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 32, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 25, the HCDR2 has a sequence of SEQ ID NO: 32, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 21, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 21, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 21, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 21, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 26, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 26, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 26, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 26, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 29, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 29, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 29, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 29, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 32, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 32, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 32, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 28, the HCDR2 has a sequence of SEQ ID NO: 32, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 21, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 21, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 21, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 21, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 26, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 26, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 26, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 26, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 29, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 29, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 29, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 29, and the HCDR3 has a sequence of SEQ ID NO: 33.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 32, and the HCDR3 has a sequence of SEQ ID NO: 22.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 32, and the HCDR3 has a sequence of SEQ ID NO: 27.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 32, and the HCDR3 has a sequence of SEQ ID NO: 30.

In some embodiments, the antibody, or antigen binding fragment thereof, comprises a heavy chain having a HCDR1, a HCDR2, and a HCDR3, wherein the HCDR1 has a sequence of SEQ ID NO: 31, the HCDR2 has a sequence of SEQ ID NO: 32, and the HCDR3 has a sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 17; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 18; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 20; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 25; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 28; the HCDR2 has the amino acid sequence of SEQ ID NO: 32; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 21; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 26; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 29; and the HCDR3 has the amino acid sequence of SEQ ID NO: 33.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 22.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 27.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 30.

In some embodiments, the antibody, or antigen binding fragment thereof, comprises: (i) a light chain variable region comprising a LCDR1, a LCDR2, and a LCDR3, wherein the LCDR1 has the amino acid sequence of SEQ ID NO: 23; the LCDR2 has the amino acid sequence of SEQ ID NO: 24; and the LCDR3 has the amino acid sequence of SEQ ID NO: 19; and (ii) a heavy chain variable region comprising a HCDR1, a HCDR2, and a HCDR3, wherein the HCDR1 has the amino acid sequence of SEQ ID NO: 31; the HCDR2 has the amino acid sequence of SEQ ID NO: 32; and the HCDR3 has the amino acid sequence of SEQ ID NO: 33.

In some embodiments, the antibody, or antigen binding fragment thereof, comprises one or more peptides having the amino acid sequence of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13, or a variant thereof.

| SEQ ID NO: | AB ID NO. | Sequence |
|---|---|---|
| 11 | MAb1-VL | SYELTQPPSVSVSPGQTARITCSGGYNGHYGWYQQKPGQAPVTVIYSNNQRPSGIPERFSGSSSGTTVTLTISGVQAEDEADYYCGGYDSSAGIFGGGTKLTVL |
| 10 | MAb1-VH | EVQLLESGGGLVQPGGSLRLSCAASGFTFSSYGMGWVRQAPGKGLEWVAAITRDSSTNYGAAVKGRATISRDNSKNTLYLQMNSLRAEDTAVYYCAKDASNGYCWYTGRGSYSCGAHHIDAWGQGTLVTVSS |
| 5 | MAb2-VL | SYELTQPPSVSVSPGQTARITCSGGSGSYGYYGWYQQKPGQAPVTVIYGTNKRPSGIPERFSGSSSGTTVTLTISGVQAEDEADYYCGGYDSSAGIFGGGTKLTVL |
| 4 | MAb2-VH | EVQLLESGGGLVQPGGSLRLSCAASGFTFSSYGMSWVRQAPGKGLEWVAGIGSSGSDTWYADSVKGRFTISRDNSKNTLYLQMNSLRAEDTAVYYCAKDATNGYCWYTGRGSYSCGAHHIDAWGQGTLVTVSS |
| 7 | MAb3-VL | SYELTQPPSVSVSPGQTARITCSGGYNGHYGWYQQKPGQAPVLVIYSNNQRPSGIPERFSGSSSGTTVTLTISGVQAEDEADYYCGGYDSSAGIFGGGTKLTVL |
| 6 | MAb3-VH | EVQLLESGGGLVQPGGSLRLSCAASGFTFRSYAMMWVRQAPGKGLEWVGEISSTGGSTYYGSAVKGRATISRDNSKNTLYLQMNSLRAEDTAVYYCAKSTYGATWKSADSIDAWGQGTLVTVSS |
| 9 | MAb4-VL | SYELTQPPSVSVAPGKTARITCSGGYNGHYGWYQQKPGQAPVLVIYSNNQRPSGIPERFSGSNSGNTATLTISRVEAGDEADYYCGGYDSSAGIFGGGTKLTVL |
| 8 | MAb4-VH | EVQLLESGGGLVQPGGSLRLSCAASGFTFRSYAMMWVRQAPGKGLEWVGEISSTGGSTYYGSAVKGRATISRDNSKNTLYLQMNSLRAEDTAVYYCAKSTYGATWKSADSIDAWGQGTLVTVSS |
| 13 | MAb5-VL | SYELTQPPSVSVAPGKTARITCSGGYNGHYGWYQQKPGQAPVLVIYSNNQRPSGIPERFSGSNSGNTATLTISRVEAGDEADYYCGGYDSSAGIFGGGTKLTVL |
| 12 | MAb5-VH | EVQLLESGGGLVQPGGSLRLSCAASGFTFSDYGMGWVRQAPGKGLEWVAAITIDGSTYYGTAVKGRATISRDNSKNTLYLQMNSLRAEDTAVYYCAKDANNGYCWYTGRGSYSCGAHNIDAWGQGTLVTVSS |

In some embodiments, the antibody, or antigen binding fragment thereof, that binds to a Claudin 18.2 protein, comprises a light chain variable ($V_L$) region having an amino acid sequence that has at least 85% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence that has at least 90%, 91%, 92%, 93%, 94%, 95%, 96%, 97%, 98%, or 99% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence that has at least 90% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 91% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 92% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 93% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 94% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 95% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 96% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 97% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 98% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 99% homology to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence that has at least 90%, 91%, 92%, 93%, 94%, 95%, 96%, 97%, 98%, or 99% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence that has at least 90% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 91% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 92% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 93% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 94% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 95% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 96% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 97% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 98% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19. In some embodiments, the antibody, or antigen binding fragment thereof, that binds to a Claudin 18.2 protein, comprises a $V_L$ region having an amino acid sequence that has at least 99% identity to that of SEQ ID NO: 5, SEQ ID NO: 7, SEQ ID NO: 9, SEQ ID NO: 11, or SEQ ID NO: 13, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence of SEQ ID NO: 5, SEQ ID NO: 7, SEQ ID NO: 9, SEQ ID NO: 11, or SEQ ID NO: 13, or any variant thereof having 1-10 substitutions, deletions, or insertions, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence of SEQ ID NO: 5, SEQ ID NO: 7, SEQ ID NO: 9, SEQ ID NO: 11, or SEQ ID NO: 13, or any variant thereof having 1-10 conservative substitutions, provided that the $V_L$ region comprises a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence of SEQ ID NO: 5, SEQ ID NO: 7, SEQ ID NO: 9, SEQ ID NO: 11, or SEQ ID NO: 13.

In some embodiments, the antibody, or antigen binding fragment thereof, that binds to a Claudin 18.2 protein, comprises a $V_L$ region having an amino acid sequence of SEQ ID NO: 5, or a variant thereof, provided that the $V_L$ region comprises a LCDR1, a LCDR2, and a LCDR3, wherein the LCDR1 has an amino acid sequence SEQ ID NO: 17; the LCDR2 has an amino acid sequence of SEQ ID NO: 18; and the LCDR3 sequence has an amino acid sequence of SEQ ID NO: 19.

In some embodiments, the antibody, or antigen binding fragment thereof, that binds to a Claudin 18.2 protein, comprises a $V_L$ region having an amino acid sequence of SEQ ID NO: 7, SEQ ID NO: 9, SEQ ID NO: 11, or SEQ ID NO: 13, or variants thereof, provided that the $V_L$ region comprises a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 sequence has an amino acid sequence of SEQ ID NO: 19.

In some embodiments, the antibody, or antigen binding fragment thereof, that binds to a Claudin 18.2 protein, comprises a heavy chain variable ($V_H$) region having an amino acid sequence that has at least 85% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence that has at least 90%, 91%, 92%, 93%, 94%, 95%, 96%, 97%, 98%, or 99% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence that has at least 90% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 91% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 92% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 93% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 94% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 95% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 96% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 97% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 98% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 99% homology to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence that has at least 90%, 91%, 92%, 93%, 94%, 95%, 96%, 97%, 98%, or 99% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence that has at least 90% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 91% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 92% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 93% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 94% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 95% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 96% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 97% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 98% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33. In some embodiments, the antibody, or antigen binding fragment thereof, that binds to a Claudin 18.2 protein, comprises a $V_H$ region having an amino acid sequence that has at least 99% identity to that of SEQ ID NO: 4, SEQ ID NO: 6, SEQ ID NO: 8, SEQ ID NO: 10, or SEQ ID NO: 12, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence of SEQ ID NO: 4, SEQ ID NO: 6, SEQ ID NO: 8, SEQ ID NO: 10, or SEQ ID NO: 12, or any variant thereof having 1-10 substitutions, deletions, or insertions, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence of SEQ ID NO: 4, SEQ ID NO: 6, SEQ ID NO: 8, SEQ ID NO: 10, or SEQ ID NO: 12, or any variant thereof having 1-10 conservative substitutions, provided that the $V_H$ region comprises a HCDR1, a HCDR2, and a HCDR3, wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 sequence has an amino acid sequence of SEQ ID NO: 22, SEQ ID NO: 27, SEQ ID NO: 30, or SEQ ID NO: 33.

In some embodiments, the antibody, or antigen binding fragment thereof, that binds to a Claudin 18.2 protein, comprises a $V_H$ region having an amino acid sequence of SEQ ID NO: 4, SEQ ID NO: 6, SEQ ID NO: 8, SEQ ID NO: 10, or SEQ ID NO: 12.

In some embodiments, the antibody, or antigen binding fragment thereof, that binds to a Claudin 18.2 protein, comprises a $V_H$ region having an amino acid sequence of SEQ ID NO: 4, or a variant thereof, provided that the $V_H$ region comprises a HCDR1, a HCDR2, and a HCDR3, wherein the HCDR1 has an amino acid sequence SEQ ID NO: 20; the HCDR2 has an amino acid sequence of SEQ ID NO: 21; and the HCDR3 sequence has an amino acid sequence of SEQ ID NO: 22.

In some embodiments, the antibody, or antigen binding fragment thereof, that binds to a Claudin 18.2 protein, comprises a $V_H$ region having an amino acid sequence of SEQ ID NO: 6, or SEQ ID NO: 8, or variants thereof, provided that the $V_H$ region comprises a HCDR1, a HCDR2, and a HCDR3, wherein the HCDR1 has an amino acid sequence SEQ ID NO: 25; the HCDR2 has an amino acid sequence of SEQ ID NO: 26; and the HCDR3 sequence has an amino acid sequence of SEQ ID NO: 27.

In some embodiments, the antibody, or antigen binding fragment thereof, that binds to a Claudin 18.2 protein, comprises a $V_H$ region having an amino acid sequence of SEQ ID NO: 10, or a variant thereof, provided that the $V_H$ region comprises a HCDR1, a HCDR2, and a HCDR3, wherein the HCDR1 has an amino acid sequence SEQ ID NO: 28; the HCDR2 has an amino acid sequence of SEQ ID NO: 29; and the HCDR3 sequence has an amino acid sequence of SEQ ID NO: 30.

In some embodiments, the antibody, or antigen binding fragment thereof, that binds to a Claudin 18.2 protein, comprises a $V_H$ region having an amino acid sequence of SEQ ID NO: 12, or a variant thereof, provided that the $V_H$ region comprises a HCDR1, a HCDR2, and a HCDR3, wherein the HCDR1 has an amino acid sequence SEQ ID NO: 31; the HCDR2 has an amino acid sequence of SEQ ID NO: 32; and the HCDR3 sequence has an amino acid sequence of SEQ ID NO: 33.

In some embodiments, the antibody, or antigen binding fragment thereof, comprises SEQ ID NO: 4 and SEQ ID NO: 5, or the CDR regions thereof.

In some embodiments, the antibody, or antigen binding fragment thereof, comprises SEQ ID NO: 6 and SEQ ID NO: 7, or the CDR regions thereof.

In some embodiments, the antibody, or antigen binding fragment thereof, comprises SEQ ID NO: 8 and SEQ ID NO: 9, or the CDR regions thereof.

In some embodiments, the antibody, or antigen binding fragment thereof, comprises SEQ ID NO: 10 and SEQ ID NO: 11, or the CDR regions thereof.

In some embodiments, the antibody, or antigen binding fragment thereof, comprises SEQ ID NO: 12 and SEQ ID NO: 13, or the CDR regions thereof.

In some embodiments, the antibody or antigen binding fragment comprises: (i) a $V_L$ region comprising a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence of SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 has an amino acid sequence of SEQ ID NO: 22, SEQ ID NO: 27, SEQ ID NO: 30, or SEQ ID NO: 33.

In some embodiments, the antibody or antigen binding fragment comprises: (i) a $V_L$ region having an amino acid sequence of SEQ ID NO: 5, or a variant thereof, provided that the $V_L$ region comprises a LCDR1, a LCDR2, and a LCDR3, wherein the LCDR1 has an amino acid sequence SEQ ID NO: 17; the LCDR2 has an amino acid sequence of SEQ ID NO: 18; and the LCDR3 sequence has an amino acid sequence of SEQ ID NO: 19; and (ii) a $V_H$ region having an amino acid sequence of SEQ ID NO: 4, or a variant thereof, provided that the $V_H$ region comprises a HCDR1, a HCDR2, and a HCDR3, wherein the HCDR1 has an amino acid sequence SEQ ID NO: 20; the HCDR2 has an amino acid sequence of SEQ ID NO: 21; and the HCDR3 sequence has an amino acid sequence of SEQ ID NO: 22.

In some embodiments, the antibody or antigen binding fragment comprises: (i) a $V_L$ region having an amino acid sequence of SEQ ID NO: 7, or a variant thereof, provided that the $V_L$ region comprises a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 sequence has an amino acid sequence of SEQ ID NO: 19; and (ii) a $V_H$ region having an amino acid sequence of SEQ ID NO: 6, or a variant thereof, provided that the $V_H$ region comprises a HCDR1, a HCDR2, and a HCDR3, wherein the HCDR1 has an amino acid sequence SEQ ID NO: 25; the HCDR2 has an amino acid sequence of SEQ ID NO: 26; and the HCDR3 sequence has an amino acid sequence of SEQ ID NO: 27.

In some embodiments, the antibody or antigen binding fragment comprises: (i) a $V_L$ region having an amino acid sequence of SEQ ID NO: 9, or a variant thereof, provided that the $V_L$ region comprises a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 sequence has an amino acid sequence of SEQ ID NO: 19; and (ii) a $V_H$ region having an amino acid sequence of SEQ ID NO: 8, or a variant thereof, provided that the $V_H$ region comprises a HCDR1, a HCDR2, and a HCDR3, wherein the HCDR1 has an amino acid sequence SEQ ID NO: 25; the HCDR2 has an amino acid sequence of SEQ ID NO: 26; and the HCDR3 sequence has an amino acid sequence of SEQ ID NO: 27.

In some embodiments, the antibody or antigen binding fragment comprises: (i) a $V_L$ region having an amino acid sequence of SEQ ID NO: 11, or a variant thereof, provided that the $V_L$ region comprises a LCDR1, a LCDR2, and a LCDR3, wherein the LCDR1 has an amino acid sequence of SEQ ID NO: 23; the LCDR2 has an amino acid sequence of SEQ ID NO: 24; and the LCDR3 sequence has an amino acid sequence of SEQ ID NO: 19; and (ii) a $V_H$ region having an amino acid sequence of SEQ ID NO: 10, or a variant thereof, provided that the $V_H$ region comprises a HCDR1, a HCDR2, and a HCDR3, wherein the HCDR1 has an amino acid sequence SEQ ID NO: 28; the HCDR2 has an amino acid sequence of SEQ ID NO: 29; and the HCDR3 sequence has an amino acid sequence of SEQ ID NO: 30.

In some embodiments, the antibody or antigen binding fragment comprises: (i) a $V_L$ region having an amino acid sequence of SEQ ID NO: 13, or a variant thereof, provided that the $V_L$ region comprises a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 sequence has an amino acid sequence of SEQ ID NO: 19; and (ii) a $V_H$ region having an amino acid sequence of SEQ ID NO: 12, or a variant thereof, provided that the $V_H$ region comprises a HCDR1, a HCDR2, and a HCDR3, wherein the HCDR1 has an amino acid sequence SEQ ID NO: 31; the HCDR2 has an amino acid sequence of SEQ ID NO: 32; and the HCDR3 sequence has an amino acid sequence of SEQ ID NO: 33.

In some embodiments, the LCDR1 is replaced with any of the other LCDR1 sequences. In some embodiments, the LCDR2 is replaced with any of the other LCDR2 sequences. In some embodiments, the LCDR3 is replaced with any of the other LCDR3 sequences. In some embodiments, the HCDR1 is replaced with any of the other LCDR1 sequences.

In some embodiments, the HCDR2 is replaced with any of the other LCDR2 sequences. In some embodiments, the HCDR3 is replaced with any of the other LCDR3 sequences.

In some embodiments, the antibody, or antigen binding fragment thereof, comprises a $V_H$ region and a $V_L$ region, wherein the $V_H$ region comprises a sequence of SEQ ID NO: 4 and the $V_L$ region comprises a sequence of SEQ ID NO: 5.

In some embodiments, the antibody, or antigen binding fragment thereof, comprises a $V_H$ region and a $V_L$ region, wherein the $V_H$ region comprises a sequence of SEQ ID NO: 4 and the $V_L$ region comprises a sequence of SEQ ID NO: 7.

In some embodiments, the antibody, or antigen binding fragment thereof, comprises a $V_H$ region and a $V_L$ region, wherein the $V_H$ region comprises a sequence of SEQ ID NO: 4 and the $V_L$ region comprises a sequence of SEQ ID NO: 9.

In some embodiments, the antibody, or antigen binding fragment thereof, comprises a $V_H$ region and a $V_L$ region, wherein the $V_H$ region comprises a sequence of SEQ ID NO: 4 and the $V_L$ region comprises a sequence of SEQ ID NO: 11.

In some embodiments, the antibody, or antigen binding fragment thereof, comprises a $V_H$ region and a $V_L$ region, wherein the $V_H$ region comprises a sequence of SEQ ID NO: 4 and the $V_L$ region comprises a sequence of SEQ ID NO: 13.

In some embodiments, the antibody, or antigen binding fragment thereof, comprises a $V_H$ region and a $V_L$ region, wherein the $V_H$ region comprises a sequence of SEQ ID NO: 6 and the $V_L$ region comprises a sequence of SEQ ID NO: 5.

In some embodiments, the antibody, or antigen binding fragment thereof, comprises a $V_H$ region and a $V_L$ region, wherein the $V_H$ region comprises a sequence of SEQ ID NO: 6 and the $V_L$ region comprises a sequence of SEQ ID NO: 7.

In some embodiments, the antibody, or antigen binding fragment thereof, comprises a $V_H$ region and a $V_L$ region, wherein the $V_H$ region comprises a sequence of SEQ ID NO: 6 and the $V_L$ region comprises a sequence of SEQ ID NO: 9.

In some embodiments, the antibody, or antigen binding fragment thereof, comprises a $V_H$ region and a $V_L$ region, wherein the $V_H$ region comprises a sequence of SEQ ID NO: 6 and the $V_L$ region comprises a sequence of SEQ ID NO: 11.

In some embodiments, the antibody, or antigen binding fragment thereof, comprises a $V_H$ region and a $V_L$ region, wherein the $V_H$ region comprises a sequence of SEQ ID NO: 6 and the $V_L$ region comprises a sequence of SEQ ID NO: 13.

In some embodiments, the antibody, or antigen binding fragment thereof, comprises a $V_H$ region and a $V_L$ region, wherein the $V_H$ region comprises a sequence of SEQ ID NO: 8 and the $V_L$ region comprises a sequence of SEQ ID NO: 5.

In some embodiments, the antibody, or antigen binding fragment thereof, comprises a $V_H$ region and a $V_L$ region, wherein the $V_H$ region comprises a sequence of SEQ ID NO: 8 and the $V_L$ region comprises a sequence of SEQ ID NO: 7.

In some embodiments, the antibody, or antigen binding fragment thereof, comprises a $V_H$ region and a $V_L$ region, wherein the $V_H$ region comprises a sequence of SEQ ID NO: 8 and the $V_L$ region comprises a sequence of SEQ ID NO: 9.

In some embodiments, the antibody, or antigen binding fragment thereof, comprises a $V_H$ region and a $V_L$ region, wherein the $V_H$ region comprises a sequence of SEQ ID NO: 8 and the $V_L$ region comprises a sequence of SEQ ID NO: 11.

In some embodiments, the antibody, or antigen binding fragment thereof, comprises a $V_H$ region and a $V_L$ region, wherein the $V_H$ region comprises a sequence of SEQ ID NO: 8 and the $V_L$ region comprises a sequence of SEQ ID NO: 13.

In some embodiments, the antibody, or antigen binding fragment thereof, comprises a $V_H$ region and a $V_L$ region, wherein the $V_H$ region comprises a sequence of SEQ ID NO: 10 and the $V_L$ region comprises a sequence of SEQ ID NO: 5.

In some embodiments, the antibody, or antigen binding fragment thereof, comprises a $V_H$ region and a $V_L$ region, wherein the $V_H$ region comprises a sequence of SEQ ID NO: 10 and the $V_L$ region comprises a sequence of SEQ ID NO: 7.

In some embodiments, the antibody, or antigen binding fragment thereof, comprises a $V_H$ region and a $V_L$ region, wherein the $V_H$ region comprises a sequence of SEQ ID NO: 10 and the $V_L$ region comprises a sequence of SEQ ID NO: 9.

In some embodiments, the antibody, or antigen binding fragment thereof, comprises a $V_H$ region and a $V_L$ region, wherein the $V_H$ region comprises a sequence of SEQ ID NO: 10 and the $V_L$ region comprises a sequence of SEQ ID NO: 11.

In some embodiments, the antibody, or antigen binding fragment thereof, comprises a $V_H$ region and a $V_L$ region, wherein the $V_H$ region comprises a sequence of SEQ ID NO: 10 and the $V_L$ region comprises a sequence of SEQ ID NO: 13.

In some embodiments, the antibody, or antigen binding fragment thereof, comprises a $V_H$ region and a $V_L$ region, wherein the $V_H$ region comprises a sequence of SEQ ID NO: 12 and the $V_L$ region comprises a sequence of SEQ ID NO: 5.

In some embodiments, the antibody, or antigen binding fragment thereof, comprises a $V_H$ region and a $V_L$ region, wherein the $V_H$ region comprises a sequence of SEQ ID NO: 12 and the $V_L$ region comprises a sequence of SEQ ID NO: 7.

In some embodiments, the antibody, or antigen binding fragment thereof, comprises a $V_H$ region and a $V_L$ region, wherein the $V_H$ region comprises a sequence of SEQ ID NO: 12 and the $V_L$ region comprises a sequence of SEQ ID NO: 9.

In some embodiments, the antibody, or antigen binding fragment thereof, comprises a $V_H$ region and a $V_L$ region, wherein the $V_H$ region comprises a sequence of SEQ ID NO: 12 and the $V_L$ region comprises a sequence of SEQ ID NO: 11.

In some embodiments, the antibody, or antigen binding fragment thereof, comprises a $V_H$ region and a $V_L$ region, wherein the $V_H$ region comprises a sequence of SEQ ID NO: 12 and the $V_L$ region comprises a sequence of SEQ ID NO: 13.

In addition to these specific combinations any of the $V_H$ regions and the $V_L$ regions can be combined with one another.

In some embodiments, the antibody, or antigen binding fragment thereof, comprises a peptide having an amino acid sequence as set forth in any of SEQ ID NOs: 4-13 and SEQ ID NOs: 17-33.

In some embodiments, the antibody, or antigen binding fragment thereof, comprises a sequence of, or a variant of any of the foregoing.

In some embodiments, the antibodies, or antigen binding fragments thereof, comprise variants of the amino acid sequences of SEQ ID NOs: 4, 5, 6, 7, 8, 9, 10, 11, 12, or 13.

The $V_L$ and the $V_H$ sequences can be in any format, including, but not limited to a scFv format where the $V_L$ and $V_H$ regions are linked with a peptide linker. As provided for herein, the different variable regions ($V_H$ or $V_L$) described herein can be linked with a peptide linker or not linked with a peptide linker and instead for a contiguous sequence. Examples of peptide linkers that can be used to link various peptides provided for herein include, but are not limited to: GQSSRSSGGGGSSGGGGS (SEQ ID NO: 14); $(GGGGS)_n$ (SEQ ID NO: 15); $(GGGGA)_n$ (SEQ ID NO: 16), or any combination thereof, wherein each n is independently 1-5.

In some embodiments, the variable regions are linked with a peptide linker. In some embodiments, the peptide linker comprises a sequence of GQSSRSSGGGGSSGGGGS (SEQ ID NO: 14); $(GGGGS)_n$ (SEQ ID NO: 15); $(GGGGA)_n$ (SEQ ID NO: 16), or any combination thereof, wherein each n is independently 1-5. The linked peptide format can be represented by a formula of $V_H$-Z-$V_L$ or $V_L$-Z-$V_H$, wherein Z is the peptide linker. In some embodiments, Z is GQSSRSSGGGGSSGGGGS (SEQ ID NO: 14); $(GGGGS)_n$ (SEQ ID NO: 15); $(GGGGA)_n$ (SEQ ID NO: 16), or any combination thereof, wherein each n is independently 1-5. In some embodiments, the antibody, or antigen binding fragment thereof, that binds to a Claudin 18.2 protein, comprises a peptide linker that does not comprise a sequence of GQSSRSSGGGGSSGGGGS (SEQ ID NO: 14). In some embodiments, the antibody, or antigen binding fragment thereof, that binds to a Claudin 18.2 protein, comprises a peptide linker that does not comprise a sequence of$(GGGGS)_n$ (SEQ ID NO: 15); $(GGGGA)_n$ (SEQ ID NO: 16), or any combination thereof, wherein each n is independently 1-5. In some embodiments, the variable regions are not linked with a peptide linker.

In some embodiments, the antibodies, or antigen binding fragments thereof, comprise variants of the amino acid sequences of SEQ ID NO: 14, 15, or 16.

Additionally, as provided for herein, the antibodies can be multi-specific antibodies, in that the antibodies can have multiple binding regions that target different proteins or the same protein at different epitopes. In some embodiments, the antibody, or antigen binding fragment thereof, is a bi-specific anti-CD3 x anti-CLDN 18.2 antibody or a tri-specific anti-CD3 x anti-CD28 x anti-CLDN 18.2 antibody.

In some embodiments, the antibody, or antigen binding fragment thereof, binds to residues E56, N153, Y155, M158, and G159 of the Claudin 18.2 protein. In some embodiments, the antibody, or antigen binding fragment thereof, binds to residues V40, E56, N153, Y155, M158, G159, and G160 of the Claudin 18.2 protein.

In some embodiments, a nucleic acid molecule encoding an antibody, or antigen binding fragment thereof, that binds to a Claudin 18.2 protein, as described herein, is provided.

In some embodiments, a vector comprising a nucleic acid molecule encoding an antibody, or antigen binding fragment thereof, that binds to a Claudin 18.2 protein, as described herein, is provided.

In some embodiments, a cell comprising a nucleic acid molecules encoding an antibody, or antigen binding fragment thereof, that binds to a Claudin 18.2 protein, as described herein, is provided. In some embodiments, a cell comprising a vector comprising a nucleic acid molecules encoding an antibody, or antigen binding fragment thereof, that binds to a Claudin 18.2 protein, as described herein, is provided.

Pharmaceutical Compositions

In some embodiments, a pharmaceutical composition comprising an antibody, or antigen binding fragment thereof, that binds to a Claudin 18.2 protein, as described herein, is provided.

In some embodiments, a pharmaceutical composition comprising a nucleic acid molecule encoding an antibody, or antigen binding fragment thereof, that binds to a Claudin 18.2 protein, as described herein, is provided.

In some embodiments, a pharmaceutical composition comprising a vector comprising a nucleic acid molecule encoding an antibody, or antigen binding fragment thereof, that binds to a Claudin 18.2 protein, as described herein, is provided.

In some embodiments, to prepare pharmaceutical compositions or sterile pharmaceutical compositions of the anti-Claudin 18.2 antibodies or other proteins provided herein, the antibody, or antigen binding fragment thereof, or other proteins provided herein are admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY). In some embodiments embodiment, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the pharmaceutical compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In some embodiments, a pharmaceutical composition of the present disclosure is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In some embodiments, the antibody, or antigen binding fragment thereof, or pharmaceutical composition thereof, can be administered by an invasive route such as by injection. In some embodiments, the antibody, or antigen binding fragment thereof, or pharmaceutical composition thereof, is administered intravenously, subcutaneously, intramuscularly, intraarterially, intraarticularly (e.g. in arthritis joints), intratumorally, or by inhalation, aerosol delivery. Administration by non-invasive routes (e.g., orally; for example, in a pill, capsule or tablet) is also within the scope of the present embodiments.

In some embodiments, the anti-Claudin 18.2 antibody, or antigen binding fragment thereof, or pharmaceutical composition thereof, is administered in combination with at least one additional therapeutic agent, such as, but not limited to any therapeutic used to treat a tumor gastric tumor, such as a DNA damaging agent. For example, in some embodiments, the anti-Claudin 18.2 antibody, or antigen binding fragment thereof, or pharmaceutical composition thereof, is administered in combination with at least one additional therapeutic agent, such as, but not limited to a therapeutic used to treat cancer or a condition related to cancer. Examples of such treatments and therapeutics include, but are not limited to, Abemaciclib, Abiraterone Acetate, ABRAXANE® (Paclitaxel Albumin-stabilized Nanoparticle Formulation), ABVD, ABVE, ABVE-PC, AC, Acalabrutinib, AC-T, ACTEMRA® (Tocilizumab), ADCETRIS® (Brentuximab Vedotin), ADE, Ado-Trastuzumab Emtansine, ADRIAMYCIN® (Doxorubicin Hydrochloride), Afatinib Dimaleate, AFINITOR (Everolimus), AKYNZEO® (Netupitant and Palonosetron Hydrochloride), ALDARA® (Imiquimod), Aldesleukin, ALECENSA® (Alectinib), Alectinib, Alemtuzumab, ALIMTA® (Pemetrexed Disodium), ALIQOPA® (Copanlisib Hydrochloride), ALKERAN® for Injection (Melphalan Hydrochloride), ALKERAN® Tablets (Melphalan), ALOXI® (Palonosetron Hydrochloride), ALUNBRIG® (Brigatinib), AMELUZ® (Aminolevulinic Acid Hydrochloride), Amifostine, Aminolevulinic Acid Hydrochloride, Anastrozole, Apalutamide, Aprepitant, ARANESP® (Darbepoetin Alfa), AREDIA® (Pamidronate Disodium), ARIMIDEX® (Anastrozole), AROMASIN® (Exemestane), ARRANON (Nelarabine), Arsenic Trioxide, ARZERRA® (Ofatumumab), Asparaginase *Erwinia chrysanthemi*, ASPARLAS® (Calaspargase Pegol-mknl), Atezolizumab, AVASTIN® (Bevacizumab), Avelumab, Axicabtagene Ciloleucel, Axitinib, Azacitidine, AZEDRA® (Iobenguane I 131), BAVENCIO® (Avelumab), BEACOPP, BELEODAQ® (Belinostat), Belinostat, Bendamustine Hydrochloride, BENDEKA® (Bendamustine Hydrochloride), BEP, BESPONSA® (Inotuzumab Ozogamicin), Bevacizumab, Bexarotene, Bicalutamide, BICNU® (Carmustine), Binimetinib, Bleomycin Sulfate, Blinatumomab, BLINCYTO® (Blinatumomab), Bortezomib, BOSULIF® (Bosutinib), Bosutinib, BRAFTOVI® (Encorafenib), Brentuximab Vedotin, Brigatinib, BuMel, Busulfan, BUSULFEX® (Busulfan), Cabazitaxel, CABLIVI® (Caplacizumab-yhdp), CABOMETYX® (Cabozantinib-S-Malate), Cabozantinib-S-Malate, CAF, Calaspargase Pegol-mknl, CALQUENCE® (Acalabrutinib), CAMPATH® (Alemtuzumab), CAMPTOSAR® (Irinotecan Hydrochloride), Capecitabine, Caplacizumab-yhdp, CAPOX, CARAC® (Fluorouracil-Topical), Carboplatin, CARBOPLATIN-TAXOL, Carfilzomib, Carmustine, Carmustine Implant, CASODEX® (Bicalutamide), CEM, Cemiplimab-rwlc, Ceritinib, CERUBIDINE® (Daunorubicin Hydrochloride), CERVARIX® (Recombinant HPV Bivalent Vaccine), Cetuximab, CEV, Chlorambucil, CHLORAMBUCIL-PREDNISONE, CHOP, Cisplatin, Cladribine, Clofarabine, CLOLAR® (Clofarabine), CMF, Cobimetinib, COMETRIQ® (Cabozantinib-S-Malate), Copanlisib Hydrochloride, COPDAC, COPIKTRA® (Duvelisib), COPP, COPP-ABV, COSMEGEN® (Dactinomycin), COTELLIC® (Cobimetinib), Crizotinib, CVP, Cyclophosphamide, CYRAMZA® (Ramucirumab), Cytarabine, Cytarabine Liposome, CYTOSAR-U® (Cytarabine), Dabrafenib, Dacarbazine, DACOGEN® (Decitabine), Dacomitinib, Dactinomycin, Daratumumab, Darbepoetin Alfa, DARZALEX® (Daratumumab), Dasatinib, Daunorubicin Hydrochloride, Daunorubicin Hydrochloride and Cytarabine Liposome, DAURISMO™ (Glasdegib Maleate), Decitabine, Defibrotide Sodium, DEFITELIO® (Defibrotide Sodium), Degarelix, Denileukin Diftitox, Denosumab, DEPOCYT® (Cytarabine Liposome), Dexamethasone, Dexrazoxane Hydrochloride, Dinutuximab, Docetaxel, DOXIL® (Doxorubicin Hydrochloride Liposome), Doxorubicin Hydrochloride, Doxorubicin Hydrochloride Liposome, Durvalumab, Duvelisib, EFUDEX® (Fluorouracil-Topical), ELIGARD® (Leuprolide Acetate), ELITEK® (Rasburicase), ELLENCE® (Epirubicin Hydrochloride), Elotuzumab, ELOXATIN® (Oxaliplatin), Eltrombopag Olamine, ELZONRIS® (Tagraxofusp-erzs), Emapalumab-lxsg, EMEND® (Aprepitant), EMPLICITI® (Elotuzumab), Enasidenib Mesylate, Encorafenib, Enzalutamide, Epirubicin Hydrochloride, EPOCH, Epoetin Alfa, EPOGEN® (Epoetin Alfa), ERBITUX® (Cetuximab), Eribulin Mesylate, ERIVEDGE® (Vismodegib), ERLEADA® (Apalutamide), Erlotinib Hydrochloride, ERWINAZE® (Asparaginase *Erwinia chrysanthemi*), ETHYOL® (Amifostine), ETOPOPHOS® (Etoposide Phosphate), Etoposide, Etoposide Phosphate, EVACET" (Doxorubicin Hydrochloride Liposome), Everolimus, EVISTA®)(Raloxifene Hydrochloride), EVOMELA® (Melphalan Hydrochloride), Exemestane, 5-FU (Fluorouracil Injection), 5-FU (Fluorouracil-Topical), FARESTON® (Toremifene), FARYDAK® (Panobinostat), FASLODEX® (Fulvestrant), FEC, FEMARA® (Letrozole), Filgrastim, FIRMAGON® (Degarelix), Fludarabine Phosphate, FLUOROPLEX® (Fluorouracil-Topical), Fluorouracil Injection, Fluorouracil-Topical, Flutamide, FOLFIRI, FOLFIRI-BEVACIZUMAB, FOLFIRI-CETUXIMAB, FOLFIRINOX, FOLFOX, FOLOTYN® (Pralatrexate), Fostamatinib Disodium, FU-LV, Fulvestrant, FUSILEV® (Leucovorin Calcium), GAMIFANT® (Emapalumab-lzsg), GARDASIL® (Recombinant HPV Quadrivalent Vaccine), GARDASIL® 9 (Recombinant HPV Nonavalent Vaccine), GAZYVA® (Obinutuzumab), Gefitinib, Gemcitabine Hydrochloride, GEMCITABINE-CISPLATIN, GEMCITABINE-OXALIPLATIN, Gemtuzumab Ozogamicin, GEMZAR® (Gemcitabine Hydrochloride), GILOTRIF® (Afatinib Dimaleate), Gilteritinib Fumarate, Glasdegib Maleate, GLEEVEC® (Imatinib Mesylate), GLIADEL® Wafer (Carmustine Implant), Glucarpidase, Goserelin Acetate, Granisetron, Granisetron Hydrochloride, GRANIX® (Filgrastim), HALAVEN®

(Eribulin Mesylate), HEMANGEOL® (Propranolol Hydrochloride), HYLECTA™ (Trastuzumab), (Trastuzumab and Hyaluronidase-oysk), HERCEPTIN® (Trastuzumab), HPV Bivalent Vaccine, Recombinant, HPV Nonavalent Vaccine, Recombinant, HPV Quadrivalent Vaccine, Recombinant, HYCAMTIN® (Topotecan Hydrochloride), HYDREA® (Hydroxyurea), Hydroxyurea, Hyper-CVAD, IBRANCE® (Palbociclib), Ibritumomab Tiuxetan, Ibrutinib, ICE, ICLUSIG® (Ponatinib Hydrochloride), Idarubicin Hydrochloride, Idelalisib, IDHIFA® (Enasidenib Mesylate), IFEX® (Ifosfamide), Ifosfamide, IL-2 (Aldesleukin), Imatinib Mesylate, IMBRUVICA® (Ibrutinib), IMFINZI® (Durvalumab), Imiquimod, IMLYGIC® (Talimogene Laherparepvec), INLYTA® (Axitinib), Inotuzumab Ozogamicin, Interferon Alfa-2b, Recombinant, Interleukin-2 (Aldesleukin), INTRON A® (Recombinant Interferon Alfa-2b), Iobenguane I 131, Ipilimumab, IRESSA® (Gefitinib), Irinotecan Hydrochloride, Irinotecan Hydrochloride Liposome, ISTODAX® (Romidepsin), Ivosidenib, Ixabepilone, Ixazomib Citrate, IXEMPRA® (Ixabepilone), JAKAFI® (Ruxolitinib Phosphate), JEB, JEVTANA® (Cabazitaxel), KADCYLA® (Ado-Trastuzumab Emtansine), KEPIVANCE® (Palifermin), KEYTRUDA® (Pembrolizumab), KISQALI® (Ribociclib), KYMRIAH® (Tisagenlecleucel), KYPROLIS® (Carfilzomib), Lanreotide Acetate, Lapatinib Ditosylate, Larotrectinib Sulfate, LARTRUVO™ (Olaratumab), Lenalidomide, Lenvatinib Mesylate, LENVIMA® (Lenvatinib Mesylate), Letrozole, Leucovorin Calcium, LEUKERAN® (Chlorambucil), Leuprolide Acetate, LEVULAN® KERASTICK™ (Aminolevulinic Acid Hydrochloride), LIBTAYO® (Cemiplimab-rwlc), LIPODOX® (Doxorubicin Hydrochloride Liposome), Lomustine, LONSURF® (Trifluridine and Tipiracil Hydrochloride), LORBRENA® (Lorlatinib), Lorlatinib, LUMOXITI® (Moxetumomab Pasudotox-tdfk), LUPRON® (Leuprolide Acetate), LUPRON DEPOT® (Leuprolide Acetate), LUTATHERA® (Lutetium Lu 177-Dotatate), Lutetium (Lu 177-Dotatate), LYNPARZA® (Olaparib), MARQIBO® (Vincristine Sulfate Liposome), MATULANE® (Procarbazine Hydrochloride), Mechlorethamine Hydrochloride, Megestrol Acetate, MEKINIST® (Trametinib), MEKTOVI® (Binimetinib), Melphalan, Melphalan Hydrochloride, Mercaptopurine, Mesna, MESNEX® (Mesna), Methotrexate, Methylnaltrexone Bromide, Midostaurin, Mitomycin C, Mitoxantrone Hydrochloride, Mogamulizumab-kpkc, Moxetumomab Pasudotox-tdfk, MOZOBIL® (Plerixafor), MUSTARGEN® (Mechlorethamine Hydrochloride), MVAC, MYLERAN® (Busulfan), MYLOTARG™ (Gemtuzumab Ozogamicin), Nanoparticle Paclitaxel (Paclitaxel Albumin-stabilized Nanoparticle Formulation), NAVELBINE® (Vinorelbine Tartrate), Necitumumab, Nelarabine, Neratinib Maleate, NERLYNX® (Neratinib Maleate), Netupitant and Palonosetron Hydrochloride, NEULASTA® (Pegfilgrastim), NEUPOGEN® (Filgrastim), NEXAVAR® (Sorafenib Tosylate), NILANDRON® (Nilutamide), Nilotinib, Nilutamide, NINLARO® (Ixazomib Citrate), Niraparib Tosylate Monohydrate, Nivolumab, NPLATE® (Romiplostim), Obinutuzumab, ODOMZO® (Sonidegib), OEPA, Ofatumumab, OFF, Olaparib, Olaratumab, Omacetaxine Mepesuccinate, ONCASPAR® (Pegaspargase), Ondansetron Hydrochloride, ONIVYDE® (Irinotecan Hydrochloride Liposome), ONTAK® (Denileukin Diftitox), OPDIVO® (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Pazopanib Hydrochloride, PCV, PEB, Pegaspargase, Pegfilgrastim, Peginterferon Alfa-2b, PEG-INTRON® (Peginterferon Alfa-2b), Pembrolizumab, Pemetrexed Disodium, PERJETA® (Pertuzumab), Pertuzumab, Plerixafor, Pomalidomide, POMALYST® (Pomalidomide), Ponatinib Hydrochloride, PORTRAZZA™ (Necitumumab), POTELIGEO® (Mogamulizumab-kpkc), Pralatrexate, Prednisone, Procarbazine Hydrochloride, PROCRIT® (Epoetin Alfa), PROLEUKIN® (Aldesleukin), PROLIA® (Denosumab), PROMACTA® (Eltrombopag Olamine), Propranolol Hydrochloride, PROVENGE® (Sipuleucel-T), PURINETHOL® (Mercaptopurine), PURIXAN® (Mercaptopurine), Radium 223 Dichloride, Raloxifene Hydrochloride, Ramucirumab, Rasburicase, Ravulizumab-cwvz, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, RELISTOR® (Methylnaltrexone Bromide), R-EPOCH, RETACRIT® (Epoetin Alfa), REVLIMID® (Lenalidomide), RHEUMATREX® (Methotrexate), Ribociclib, R-ICE, RITUXAN® (Rituximab), RITUXAN HYCELA® (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), RUBRACA® (Rucaparib Camsylate), Rucaparib Camsylate, Ruxolitinib Phosphate, RYDAPT® (Midostaurin), SANCUSO® (Granisetron), SCLEROSOL® Intrapleural Aerosol (Talc), Siltuximab, Sipuleucel-T, SOMATULINE® Depot (Lanreotide Acetate), Sonidegib, Sorafenib Tosylate, SPRYCEL® (Dasatinib), STANFORD V, Sterile Talc Powder (Talc), STERITALC® (Talc), STIVARGA® (Regorafenib), Sunitinib Malate, SUSTOL® (Granisetron), SUTENT® (Sunitinib Malate), SYLATRON" (Peginterferon Alfa-2b), SYLVAN™ (Siltuximab), SYNRIBO® (Omacetaxine Mepesuccinate), TABLOID® (Thioguanine), TAC, TAFINLAR® (Dabrafenib), Tagraxofusp-erzs, TAGRISSO® (Osimertinib), Talazoparib Tosylate, Talc, Talimogene Laherparepvec, TALZENNA® (Talazoparib Tosylate), Tamoxifen Citrate, TARABINE PFS® (Cytarabine), TARCEVA® (Erlotinib Hydrochloride), TARGRETIN® (Bexarotene), TASIGNA® (Nilotinib), TAVALISSE® (Fostamatinib Disodium), TAXOL® (Paclitaxel), TAXOTERE® (Docetaxel), TECENTRIQ® (Atezolizumab), TEMODAR® (Temozolomide), Temozolomide, Temsirolimus, Thalidomide, THALOMID® (Thalidomide), Thioguanine, Thiotepa, TIBSOVO® (Ivosidenib), Tisagenlecleucel, Tocilizumab, TOLAK® (Fluorouracil-Topical), Topotecan Hydrochloride, Toremifene, TORISEL® (Temsirolimus), TOTECT® (Dexrazoxane Hydrochloride), TPF, Trabectedin, Trametinib, Trastuzumab, Trastuzumab and Hyaluronidase-oysk, TREANDA® (Bendamustine Hydrochloride), TREXALL® (Methotrexate), Trifluridine and Tipiracil Hydrochloride, TRISENOX® (Arsenic Trioxide), TYKERB® (Lapatinib Ditosylate), ULTOMIRIS® (Ravulizumab-cwvz), UNITUXIN® (Dinutuximab), Uridine Triacetate, VAC, Valrubicin, VALSTAR® (Valrubicin), Vandetanib, VAMP, VARUBI® (Rolapitant Hydrochloride), VECTIBIX® (Panitumumab), VeIP, VELCADE® (Bortezomib), Vemurafenib, VENCLEXTA® (Venetoclax), Venetoclax, VERZENIO® (Abemaciclib), VIDAZA® (Azacitidine), Vinblastine Sulfate, Vincristine Sulfate, Vincristine Sulfate Liposome, Vinorelbine Tartrate, VIP, Vismodegib, VISTOGARD® (Uridine Triacetate), VITRAKVI® (Larotrectinib Sulfate), VIZIMPRO® (Dacomitinib), VORAXAZE® (Glucarpidase), Vorinostat, VOTRI- ENT® (Pazopanib Hydrochloride), VYXEOS® (Daunorubicin Hydrochloride and Cytarabine Liposome), XALKORI® (Crizotinib), XELODA® (Capecitabine), XELIRI, XELOX, XGEVA® (Denosumab), XOFIGO (Radium 223 Dichloride), XOSPATA® (Gilteritinib Fumarate), XTANDI® (Enzalutamide), YERVOY® (Ipilimumab), YESCARTA® (Axicabtagene Ciloleucel), YONDELIS® (Trabectedin), ZALTRAP® (Ziv-Aflibercept), ZARXIO® (Filgrastim), ZEJULA™ (Niraparib Tosylate Monohydrate), ZELBORAF® (Vemurafenib), ZEVALIN® (Ibritumomab Tiuxetan), ZINECARD® (Dexrazoxane Hydrochloride), Ziv-Aflibercept, ZOFRAN® (Ondansetron Hydrochloride), ZOLADEX® (Goserelin Acetate), Zoledronic Acid, ZOLINZA® (Vorinostat), ZOMETA® (Zoledronic Acid), ZYDELIG® (Idelalisib), ZYKADIA® (Ceritinib), ZYTIGA® (Abiraterone Acetate), or any combination thereof.

Pharmaceutical compositions can be administered with medical devices known in the art. For example, a pharmaceutical composition of the present disclosure can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art. Alternately, one may administer the antibody, or antigen binding fragment thereof, or pharmaceutical composition thereof, in a local rather than systemic manner, for example, via injection directly into an arthritic joint or pathogen-induced lesion characterized by immunopathology, often in a depot or sustained release formulation. Furthermore, one may administer the antibody, or antigen binding fragment thereof, or pharmaceutical composition thereof, in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue. The administration regimen depends on several factors, including the serum or tissue turnover rate of the therapeutic antibody, or antigen binding fragment thereof, the level of symptoms, the immunogenicity of the therapeutic antibody, or antigen binding fragment thereof, and the accessibility of the target cells in the biological matrix. Preferably, the administration regimen delivers sufficient therapeutic antibody, or antigen binding fragment thereof, to effect improvement in the target disease state, while simultaneously minimizing undesired side effects. Accordingly, the amount of biologic delivered depends in part on the particular therapeutic antibody, or antigen binding fragment thereof, and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348: 24-32; Lipsky et al. (2000) *New Engl. J. Med.* 343:1594-1602). Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable. Antibodies, or antigen binding fragments thereof, can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 μg/kg body weight, more generally at least 0.2 μg/kg, 0.5 μg/kg, 1 μg/kg, g/kg, 100 μg/kg, 0.25 mg/kg, 1.0 mg/kg, 2.0 mg/kg, 5.0 mg/mL, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of the antibody, or antigen binding fragment thereof, in the subject's serum, such as 0.1, 0.3, 1, 3, 10, 30, 100, 300 μg/mL or more. In other embodiments, a fully human antibody, or antigen binding fragment thereof, is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat or ameliorate tumors or gastric tumors. The term "subject" as used throughout includes any organism, such as an animal, including a mammal (e.g., rat, mouse, dog, cat, rabbit) and, for example, a human. A subject can be also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

Whereas, an isolated antibody, or antigen binding fragment thereof, binds an epitope on a Claudin 18.2 protein, or other protein described herein, and displays in vitro and/or in vivo Claudin 18.2 inhibiting or therapeutic activities, the antibodies, or antigen binding fragments thereof, capable of inhibiting Claudin 18.2 function, are suitable both as therapeutic agents for treating Claudin 18.2-associated conditions in humans and animals. These conditions include gastric tumors. According, methods of treating such conditions are also provided, wherein the method comprises administering an antibody, or antigen binding fragment thereof, to the subject with such a condition.

In some embodiments, the methods of treating a condition in a subject comprise administering a therapeutically or prophylactically effective amount of one or more monoclonal antibodies or antigen binding fragments of the antibodies described herein to a susceptible subject or to one exhibiting a condition in which Claudin 18.2 is known to have caused the pathology observed. Any active form of the antibody, or antigen fragment thereof, can be administered, including, but not limited to Fab and F(ab')2 fragments and other forms of antibodies provided for herein.

As used herein, a Claudin 18.2 associated pathology refers to conditions that are caused by the function or aberrant expression of Claudin 18.2. These conditions include, but are not limited to, tumors, lung tumors, pancreatic tumors, gastric tumors, and the like.

In some embodiments, the antibodies, or antigen binding fragments thereof, used are compatible with the recipient species such that the immune response to the MAbs does not result in an unacceptably short circulating half-life or induce an immune response to the MAbs in the subject. In some embodiments, the MAbs administered exhibit some secondary functions such as binding to Fc receptors of the subject and activation of antibody dependent cell mediated cytotoxicity (ADCC) mechanisms.

Treatment of individuals may comprise the administration of a therapeutically effective amount of the antibodies described herein. The antibodies can be provided in a kit, such as those provided herein. The antibodies can be used or administered alone or in admixture with another therapeutic, analgesic, or diagnostic agent, such as provided for herein. In providing a patient with an antibody, or antigen binding fragment thereof, capable of binding to Claudin 18.2, or an antibody, or antigen binding fragment thereof, capable of protecting against Claudin 18.2, pathology in a recipient patient, the dosage of administered agent will vary depending upon such factors as the patient's age, weight, height, sex, general medical condition, previous medical history, etc.

An antibody, or antigen binding fragment thereof, capable treating a condition associated with Claudin 18.2 activity or use to treat a Claudin 18.2 related pathology, is intended to be provided to subjects in an amount sufficient to affect a reduction, resolution, or amelioration in the Claudin 18.2 related symptom or pathology. Such a pathology includes, but is not limited to, lung tumors, pancreatic tumors, or gastric tumors.

Accordingly, in some embodiments, methods of treating a subject with a Claudin 18.2 mediated disorder are provided. In some embodiments, the method comprises administering a pharmaceutical composition comprising an antibody, or antigen binding fragment thereof, as provided herein. In some embodiments, the disorder is cancer, such as lung tumors, pancreatic tumors, or gastric tumors. In some embodiments, the tumor or gastric tumor is gastric adenocarcinoma, gastroesophageal junction adenocarcinoma, pancreatic adenocarcinoma, or non-small cell lung cancer. As provided for herein, the antibodies, or antigen binding fragments thereof, can be administered with other therapeutics. These can be administered simultaneously or sequentially.

In some embodiments, the antibodies, or antigen binding fragments thereof, may be used to treat cancer, such as lung tumors, pancreatic tumors, or gastric tumors.

Kits are also provided which are useful for carrying out embodiments described herein. The present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

Yet another aspect provided for herein is a kit for detecting Claudin 18.2 protein in a biological sample. The kit includes a container holding one or more antibody, or antigen binding fragment thereof, which binds an epitope of Claudin 18.2 protein and instructions for using the antibody, or antigen binding fragment thereof, for the purpose of binding to Claudin 18.2 protein to form an immunological complex and detecting the formation of the immunological complex such that the presence or absence of the immunological complex correlates with presence or absence of Claudin 18.2 protein in the sample. Examples of containers include multiwell plates which allow simultaneous detection of Claudin 18.2 protein in multiple samples.

In some embodiments, antibodies, or antigen binding fragments thereof, that bind to a Claudin 18.2 protein are provided. In some embodiments, the antibody, or antigen binding fragment thereof, is isolated. In some embodiments, the antibody, or antigen binding fragment thereof, binds specifically. In some embodiments, the antibody, or antigen binding fragment thereof, binds to a Claudin 18.2 protein that is properly folded. In some embodiments, the antibody, or antigen binding fragment thereof, is specific for a specific Claudin 18.2 conformational state (open or closed). In some embodiments, the antibody, or antigen binding fragment thereof, binds to a Claudin 18.2 protein in a cell membrane. In some embodiments, the antibody, or antigen binding fragment thereof, binds to a Claudin 18.2 protein that is in a cell membrane in an intact cell. In some embodiments, the antibody, or antigen binding fragment thereof, inhibits or neutralizes the function of a Claudin 18.2 protein. As used herein, the term "neutralize" means that the activity or function of the protein is inhibited. The inhibition can be complete or partial. In some embodiments, the activity or function of the protein is inhibited at least 10%, 20%, 30%, 40%, 50%, 60%, 70%, 80%, 90%, 95%, or 99%. The percent inhibition can be based upon the function or activity of the protein in the absence of the antibody, or antigen binding fragment thereof. In some embodiments, the antibody, or antigen binding fragment thereof, inhibits the glucose transport facilitated by Claudin 18.2. In some embodiments, the antibody, or antigen binding fragment thereof, inhibits the internalization of the Claudin 18.2 protein.

In some embodiments, the antibody, or antigen binding fragment thereof, comprises a sequence as provided for herein, or a fragment thereof. In some embodiments, the antibody, or antigen binding fragment thereof, comprises a HCDR. The heavy chain may be one or more of the heavy chains described herein. In some embodiments, the antibody, or antigen binding fragment thereof, comprises a light chain, or an antigen binding fragment thereof as described herein In some embodiments, methods of treating, inhibiting or ameliorating a Claudin 18.2, associated pathology are provided. In some embodiments, the methods comprise administering an antibody, or antigen binding fragment thereof, described herein or a pharmaceutical composition described herein to a subject to treat, inhibit or ameliorate a Claudin 18.2 associated pathology. In some embodiments, the pathology is cancer, such as a lung tumors, pancreatic tumors, or gastric tumors.

In some embodiments, methods of detecting the presence or absence of a Claudin 18.2 in a sample are provided, the method comprising contacting a sample with one or more antibodies described herein detecting the binding to a Claudin 18.2 antigen by the antibody, or antigen binding fragment thereof. In some embodiments, the detection of the binding indicates the presence Claudin 18.2 antigen; or the absence of the detection of the binding to the Claudin 18.2 antigen indicates the absence of the Claudin 18.2 antigen. The detecting can be done with any known method, such as using a biosensor, ELISA, sandwich assay, and the like. However, in some embodiments, the method comprises detecting the presence of the protein in non-denaturing conditions. The non-denaturing conditions can be used so that the protein of interest is detected in its native, or properly folded form.

In some embodiments, methods of identifying a test antibody, or antigen binding fragment thereof, that binds to an epitope on Claudin 18.2 protein, are provided, the method comprising contacting a test antibody, or antigen binding fragment thereof, with the epitope on Claudin 18.2 protein and determining whether the test antibody, or antigen binding fragment thereof, binds to the epitope. In some embodiments, the determining comprises determining whether the test antibody, or antigen binding fragment thereof, binds to the protein and is competitively inhibited by an antibody, or antigen binding fragment thereof, comprising a sequence as provided herein. In some embodiments, the determining comprises mutating one or more residues of epitope or protein and determining binding of the test antibody, or antigen binding fragment thereof, to the mutated epitope, wherein if the mutation reduces binding of the test antibody, or antigen binding fragment thereof, as compared to the non-mutated epitope, the test antibody, or antigen binding fragment thereof, is deemed to bind to that epitope.

In some embodiments, methods of monitoring internalization of Claudin 18.2 from the surface of a cell are provided. In some embodiments, the method comprising contacting the cell with an anti-Claudin 18.2 antibody, or antigen binding fragment thereof, as provided herein and detecting the presence of Claudin 18.2 in the cell or on the surface of the cell. The differences in cell surface expression can be measured and the internalization can be monitored and measured. This can be used, for example, to measure the effect of another molecule, such as a test agent, to modulate internalization of Claudin 18.2 protein. Thus, the antibodies provided for herein can be used to identify test agents that modulate (increase or decrease) the internalization of Claudin 18.2 protein. Test molecules that increase the internalization, which would be measured as a decrease in binding of an anti-Claudin 18.2 antibody, or antigen binding fragment thereof, to Claudin 18.2 protein on the cell surface, can be identified according to the methods provided herein. Test molecules that decrease the internalization, which would be measured as an increase in binding of an anti-Claudin 18.2 antibody, or antigen binding fragment thereof, to Claudin 18.2 protein on the cell surface, can be identified according to the methods provided herein. The surface expression can be measured by fluorescence, which can be done through a secondary antibody, or antigen binding fragment thereof, that recognized the Claudin 18.2 antibodies or by labelling the anti-Claudin 18.2 antibodies provided for herein.

In some embodiments, methods of inducing an immune response against a Claudin 18.2 antigen are provided, the methods comprising administering a Claudin 18.2 antigen to a subject under conditions sufficient to induce an immune response. In some embodiments, the Claudin 18.2 antigen is delivered as a nucleic acid molecule encoding the Claudin 18.2 antigen. As discussed herein, in some embodiments, the methods comprise administering a virus-like particle, such as a lipoparticle, comprising a Claudin 18.2 antigen to the subject to induce the immune response. In some embodiments, antibodies produced by the immune response are isolated. The antibodies can then be cloned, isolated and/or otherwise modified as described herein.

In some embodiments, antibodies, or antigen binding fragments thereof, are further identified using a display library. In some embodiments, the antibodies, or antigen binding fragments thereof, that are generated through the use of VLPs that express Claudin 18.2 protein are isolated and put into a library to further identify antibodies, or antigen binding fragments thereof. The libraries can be phage library or a yeast expression library. In some embodiments, the library is made from the immunized animal that generates antibodies against the Claudin 18.2 VLPs. Thus, the antibodies, or antigen binding fragments thereof, can be identified by detecting the binding of a Claudin 18.2 VLP with one of the protein members of the library.

In some embodiments, the library is a naïve library that is generated from a subject's antibodies. The library can also be a synthetic library that utilizes combinatorial biology to produce synthetic antibodies, or antigen binding fragments thereof, to produce antibodies, or antigen binding fragments thereof, that bind to Claudin 18.2 protein. The binding partners can be identified by screening, for example, the members of the library against VLPs that express Claudin 18.2 protein. Any method can be used to detect the binding of the antibody, or antigen binding fragment thereof, with the VLP that expresses or contains Claudin 18.2 on its surface.

In some embodiments, the subject is a chicken.

In some embodiments, a method of generating an antibody, or antigen binding fragment thereof, that binds to a Claudin 18.2 protein, is provided. In some embodiments, the method of generating an antibody, or antigen binding fragment thereof, that binds to a Claudin 18.2 protein, comprises administering a virus-like particle comprising the Claudin 18.2 protein on its surface to a subject under conditions to induce an immune response against the Claudin 18.2 protein. In some embodiments, the subject is a human, a mouse, a sheep, a rat, a rabbit, a shark, a llama, or a chicken. In some embodiments, the method of generating an antibody, or antigen binding fragment thereof, that binds to a Claudin 18.2 protein, further comprises isolating the antibody that binds to the Claudin 18.2 protein. In some embodiments, the antibody, or antigen binding fragment thereof, that is generated binds to an extracellular domain of the Claudin 18.2 protein. In some embodiments, the method of generating an antibody, or antigen binding fragment thereof, that binds to a Claudin 18.2 protein, further comprises generating a virus-like particle comprising the Claudin 18.2 protein. In some embodiments, the method of generating an antibody, or antigen binding fragment thereof, that binds to a Claudin 18.2 protein, further comprises transfecting or transducing a cell with a Claudin 18.2 protein and a retroviral gag protein under conditions sufficient to produce a virus-like particle comprising the Claudin 18.2 protein. In some embodiments, the cell is a HEK-293T cell. In some embodiments, the gag protein is a MLV gag protein. In some embodiments, the retroviral gag protein is Murine Leukemia Virus (MLV), gag, HIV gag, or RSV gag protein.

In some embodiments, a method of modulating Claudin 18.2 activity is provided. In some embodiments, the method of modulating Claudin 18.2 activity comprises contacting a cell expressing Claudin 18.2 with a Claudin 18.2 antibody, or antigen binding fragment thereof, that binds to Claudin 18.2 on the cell surface. In some embodiments, the method of modulating Claudin 18.2 activity comprises contacting a cell expressing Claudin 18.2 with a pharmaceutical composition comprising a Claudin 18.2 antibody, or antigen binding fragment thereof, that binds to Claudin 18.2 on the cell surface. In some embodiments, the method of modulating Claudin 18.2 activity comprises administering to a subject an antibody, or antigen binding fragment thereof, that binds to Claudin 18.2 protein, as provided for herein. In some embodiments, the method of modulating Claudin 18.2 activity comprises administering to a subject a pharmaceutical composition comprising an antibody, or antigen binding fragment thereof, that binds to Claudin 18.2 protein, as provided for herein.

In some embodiments, a chimeric antigen receptor is provided, wherein the chimeric antigen receptor comprises an extracellular portion comprising an antibody or, antigen binding fragment thereof, that binds to Claudin 18.2, as provided herein. In some embodiments, chimeric antigen receptor comprises an extracellular portion comprising an antibody or, antigen binding fragment thereof, that binds to Claudin 18.2, as provided herein, wherein the antibody or, antigen binding fragment thereof, comprises a binding domain, and wherein the binding domain is a scFv fragment.

In some embodiments, a multi-specific molecule is provided, wherein the multi-specific molecule comprises a first portion or domain that binds to a Claudin 18.2 protein, and a second portion or domain that binds to a second molecule. In some embodiments, the multi-specific molecule has a therapeutic effect on cells that express Claudin 18.2. In some embodiments, the first portion or domain that binds to Claudin 18.2 is an antibody or binding fragment thereof, as provided for herein. In some embodiments, the first portion or domain that binds to Claudin 18.2 is an antibody or binding fragment thereof, as provided for herein, comprising a binding domain, wherein the binding domain is an scFv fragment.

Enumerated Embodiments

1. A recombinant antibody, or antigen binding fragment thereof, that binds to a Claudin 18.2 protein, wherein the Claudin 18.2 protein is in its native conformation.

2. The antibody, or antigen binding fragment thereof, of embodiment 1, wherein the Claudin 18.2 protein is human Claudin 18.2 protein.

3. The antibody, or antigen binding fragment thereof, of embodiment 1, wherein the antibody, or antigen binding fragment thereof, is a humanized antibody.

4. The antibody, or antigen binding fragment thereof, of embodiment 1, wherein the antibody, or antigen binding fragment thereof, is a chicken antibody.

5. The antibody, or antigen binding fragment thereof, of any one of embodiments 1-4, wherein the antibody, or antigen binding fragment thereof, is a monoclonal antibody.

6. The antibody, or antigen binding fragment thereof, of any one of embodiments 1-4, wherein the antibody, or antigen binding fragment thereof, is an scFv antibody.

7. The antibody, or antigen binding fragment thereof, of any one of embodiments 1-6, wherein the antibody or antigen binding fragment comprises: a light chain variable ($V_L$) region comprising a light chain CDR1 (LCDR1), a light chain CDR2 (LCDR2), and a light chain CDR3 (LCDR3), wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 has an amino acid sequence of SEQ ID NO: 19.

8. The antibody, or antigen binding fragment thereof, of embodiment 7, wherein the antibody, or antigen binding fragment thereof, comprises a $V_L$ region having an amino acid sequence that has at least 85% homology to that of SEQ ID NO: 5, SEQ ID NO: 7, SEQ ID NO: 9, SEQ ID NO: 11, or SEQ ID NO: 13.

9. The antibody, or antigen binding fragment thereof, of embodiment 7, wherein the antibody, or antigen binding fragment thereof, comprises a $V_L$ region having an amino acid sequence that has at least 90%, 91%, 92%, 93%, 94%, 95%, 96%, 97%, 98%, or 99% homology to that of SEQ ID NO: 5, SEQ ID NO: 7, SEQ ID NO: 9, SEQ ID NO: 11, or SEQ ID NO: 13.

10. The antibody, or antigen binding fragment thereof, of embodiment 7, wherein the antibody, or antigen binding fragment thereof, comprises a $V_L$ region having an amino acid sequence that has at least 90%, 91%, 92%, 93%, 94%, 95%, 96%, 97%, 98%, or 99% identity to that of SEQ ID NO: 5, SEQ ID NO: 7, SEQ ID NO: 9, SEQ ID NO: 11, or SEQ ID NO: 13.

11. The antibody, or antigen binding fragment thereof, of embodiment 7, wherein the antibody, or antigen binding fragment thereof, comprises a $V_L$ region having an amino acid sequence of SEQ ID NO: 5, SEQ ID NO: 7, SEQ ID NO: 9, SEQ ID NO: 11, or SEQ ID NO: 13, or any variant thereof having 1-10 substitutions, deletions, or insertions.

12. The antibody, or antigen binding fragment thereof, of embodiment 7, wherein the antibody, or antigen binding fragment thereof, comprises a $V_L$ region having an amino acid sequence of SEQ ID NO: 5, SEQ ID NO: 7, SEQ ID NO: 9, SEQ ID NO: 11, or SEQ ID NO: 13, or any variant thereof having 1-10 conservative substitutions.

13. The antibody, or antigen binding fragment thereof, of embodiment 7, wherein the antibody, or antigen binding fragment thereof, comprises a $V_L$ region having an amino acid sequence of SEQ ID NO: 5, SEQ ID NO: 7, SEQ ID NO: 9, SEQ ID NO: 11, or SEQ ID NO: 13.

14. The antibody, or antigen binding fragment thereof, of any one of embodiments 7-13, wherein the antibody, or antigen binding fragment thereof, comprises a $V_L$ region comprising a LCDR1, a LCDR2, and a LCDR3, wherein the LCDR1 has an amino acid sequence SEQ ID NO: 17; the LCDR2 has an amino acid sequence of SEQ ID NO: 18; and the LCDR3 has an amino acid sequence of SEQ ID NO: 19.

15. The antibody, or antigen binding fragment thereof, of any one of embodiments 7-13, wherein the antibody, or antigen binding fragment thereof, comprises a $V_L$ region comprising a LCDR1, a LCDR2, and a LCDR3, wherein the antibody, or antigen binding fragment thereof, wherein the LCDR1 having an amino acid sequence SEQ ID NO: 23; the LCDR2 has an amino acid sequence of SEQ ID NO: 24; and the LCDR3 has an amino acid sequence of SEQ ID NO: 19.

16. The antibody, or antigen binding fragment thereof, of any one of embodiments 1-15, wherein the antibody or antigen binding fragment comprises: a heavy chain variable ($V_H$) region comprising a heavy chain CDR1 (HCDR1), a heavy chain CDR2 (HCDR2), and a heavy chain CDR3 (HCDR3), wherein the HCDR1 has an amino acid sequence SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 has an amino acid sequence of SEQ ID NO: 22, SEQ ID NO: 27, SEQ ID NO: 30, or SEQ ID NO: 33.

17. The antibody, or antigen binding fragment thereof, of embodiment 16, wherein the antibody, or antigen binding fragment thereof, comprises a $V_H$ region having an amino acid sequence that has at least 85% homology to that of SEQ ID NO: 4, SEQ ID NO: 6, SEQ ID NO: 8, SEQ ID NO: 10, or SEQ ID NO: 12.

18. The antibody, or antigen binding fragment thereof, of embodiment 16, wherein the antibody, or antigen binding fragment thereof, comprises a $V_H$ region having an amino acid sequence that has at least 90%, 91%, 92%, 93%, 94%, 95%, 96%, 97%, 98%, or 99% homology to that of SEQ ID NO: 4, SEQ ID NO: 6, SEQ ID NO: 8, SEQ ID NO: 10, or SEQ ID NO: 12.

19. The antibody, or antigen binding fragment thereof, of embodiment 16, wherein the antibody, or antigen binding fragment thereof, comprises a $V_H$ region having an amino acid sequence that has at least 90%, 91%, 92%, 93%, 94%, 95%, 96%, 97%, 98%, or 99% identity to that of SEQ ID NO: 4, SEQ ID NO: 6, SEQ ID NO: 8, SEQ ID NO: 10, or SEQ ID NO: 12.

20. The antibody, or antigen binding fragment thereof, of embodiment 16, wherein the antibody, or antigen binding fragment thereof, comprises a $V_H$ region having an amino acid sequence of SEQ ID NO: 4, SEQ ID NO: 6, SEQ ID NO: 8, SEQ ID NO: 10, or SEQ ID NO: 12, or any variant thereof having 1-10 substitutions, deletions, or insertions.

21. The antibody, or antigen binding fragment thereof, of embodiment 16, wherein the antibody, or antigen binding fragment thereof, comprises a $V_H$ region having an amino acid sequence of SEQ ID NO: 4, SEQ ID NO: 6, SEQ ID NO: 8, SEQ ID NO: 10, or SEQ ID NO: 12, or any variant thereof having 1-10 conservative substitutions.

22. The antibody, or antigen binding fragment thereof, of embodiment 16, wherein the antibody, or antigen binding fragment thereof, comprises a $V_H$ region having an amino acid sequence of SEQ ID NO: 4, SEQ ID NO: 6, SEQ ID NO: 8, SEQ ID NO: 10, or SEQ ID NO: 12.

23. The antibody, or antigen binding fragment thereof, of any one of embodiments 16-22, wherein the antibody, or antigen binding fragment thereof, comprises a $V_H$ region comprising a HCDR1, a HCDR2, and a HCDR3, wherein the HCDR1 has an amino acid sequence of SEQ ID NO: 20; the HCDR2 has an amino acid sequence of SEQ ID NO: 21; and the HCDR3 has an amino acid sequence of SEQ ID NO: 22.

24. The antibody, or antigen binding fragment thereof, of any one of embodiments 16-22, wherein the antibody, or antigen binding fragment thereof, comprises a $V_H$ region comprising a HCDR1, a HCDR2, and a HCDR3, wherein the HCDR1 has an amino acid sequence of SEQ ID NO: 25; the HCDR2 has an amino acid sequence of SEQ ID NO: 26; and the HCDR3 has an amino acid sequence of SEQ ID NO: 27.

25. The antibody, or antigen binding fragment thereof, of any one of embodiments 16-22, wherein the antibody, or antigen binding fragment thereof, comprises a $V_H$ region comprising a HCDR1, a HCDR2, and a HCDR3, wherein the HCDR1 has an amino acid sequence of SEQ ID NO: 28; the HCDR2 has an amino acid sequence of SEQ ID NO: 29; and the HCDR3 has an amino acid sequence of SEQ ID NO: 30.

26. The antibody, or antigen binding fragment thereof, of any one of embodiments 16-22, wherein the antibody, or antigen binding fragment thereof, comprises a $V_H$ region comprising a HCDR1, a HCDR2, and a HCDR3, wherein the HCDR1 has an amino acid sequence of SEQ ID NO: 31; the HCDR2 has an amino acid sequence of SEQ ID NO: 32; and the HCDR3 has an amino acid sequence of SEQ ID NO: 33.

27. The antibody, or antigen binding fragment thereof, of any one of embodiments 1-26, wherein the antibody or antigen binding fragment comprises: (i) a $V_L$ region comprising a LCDR1, a LCDR2, and a LCDR3, wherein the LCDR1 has an amino acid sequence SEQ ID NO: 17 or SEQ ID NO: 23; the LCDR2 has an amino acid sequence of SEQ ID NO: 18 or SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence of SEQ ID NO: 20, SEQ ID NO: 25, SEQ ID NO: 28, or SEQ ID NO: 31; the HCDR2 has an amino acid sequence of SEQ ID NO: 21, SEQ ID NO: 26, SEQ ID NO: 29, or SEQ ID NO: 32; and the HCDR3 has an amino acid sequence of SEQ ID NO: 22, SEQ ID NO: 27, SEQ ID NO: 30, or SEQ ID NO: 33.

28. The antibody, or antigen binding fragment thereof, of embodiment 27, wherein the antibody or antigen binding fragment comprises: (i) a $V_L$ region comprising a LCDR1, a LCDR2, and a LCDR3, wherein the LCDR1 has an amino acid sequence SEQ ID NO: 17; the LCDR2 has an amino acid sequence of SEQ ID NO: 18; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 20; the HCDR2 has an amino acid sequence of SEQ ID NO: 21; and the HCDR3 has an amino acid sequence of SEQ ID NO: 22.

29. The antibody, or antigen binding fragment thereof, of embodiment 28, wherein the antibody or antigen binding fragment comprises: (i) a $V_L$ region having an amino acid sequence of SEQ ID NO: 5, or a variant thereof, and (ii) a $V_H$ region having an amino acid sequence of SEQ ID NO: 4, or a variant thereof.

30. The antibody, or antigen binding fragment thereof, of embodiment 27, wherein the antibody or antigen binding fragment comprises: (i) a $V_L$ region comprising a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 25; the HCDR2 has an amino acid sequence of SEQ ID NO: 26; and the HCDR3 has an amino acid sequence of SEQ ID NO: 27.

31. The antibody, or antigen binding fragment thereof, of embodiment 30, wherein the antibody or antigen binding fragment comprises: (i) a $V_L$ region having an amino acid sequence of SEQ ID NO: 7, or a variant thereof, and (ii) a $V_H$ region having an amino acid sequence of SEQ ID NO: 6, or a variant thereof.

32. The antibody, or antigen binding fragment thereof, of embodiment 30, wherein the antibody or antigen binding fragment comprises: (i) a $V_L$ region having an amino acid sequence of SEQ ID NO: 9, or a variant thereof, and (ii) a $V_H$ region having an amino acid sequence of SEQ ID NO: 8, or a variant thereof.

33. The antibody, or antigen binding fragment thereof, of embodiment 27, wherein the antibody or antigen binding fragment comprises: (i) a $V_L$ region comprising a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 28; the HCDR2 has an amino acid sequence of SEQ ID NO: 29; and the HCDR3 has an amino acid sequence of SEQ ID NO: 30.

34. The antibody, or antigen binding fragment thereof, of embodiment 33, wherein the antibody or antigen binding fragment comprises: (i) a $V_L$ region having an amino acid sequence of SEQ ID NO: 11, or a variant thereof; and (ii) a $V_H$ region having an amino acid sequence of SEQ ID NO: 10, or a variant thereof.

35. The antibody, or antigen binding fragment thereof, of embodiment 27, wherein the antibody or antigen binding fragment comprises: (i) a $V_L$ region comprising a LCDR1, a LCDR2, and a LCDR3, wherein the LCDR1 has an amino acid sequence SEQ ID NO: 23; the LCDR2 has an amino acid sequence of SEQ ID NO: 24; and the LCDR3 has an amino acid sequence of SEQ ID NO: 19; and (ii) a $V_H$ region comprising a HCDR1, a HCDR2, and a HCDR3, wherein the HCDR1 has an amino acid sequence SEQ ID NO: 31; the HCDR2 has an amino acid sequence of SEQ ID NO: 32; and the HCDR3 has an amino acid sequence of SEQ ID NO: 33.

36. The antibody, or antigen binding fragment thereof, of embodiment 35, wherein the antibody or antigen binding fragment comprises: (i) a $V_L$ region having an amino acid sequence of SEQ ID NO: 13, or a variant thereof; and (ii) a $V_H$ region having an amino acid sequence of SEQ ID NO: 12, or a variant thereof.

37. The antibody, or antigen binding fragment thereof, of any one of embodiments 27-36, wherein the antibody, or antigen binding fragment thereof, comprises a $V_L$ region and a $V_H$ region that are not linked by a linker.

38. The antibody, or antigen binding fragment thereof, of any one of embodiments 7-24, wherein the antibody, or antigen binding fragment thereof, comprises a $V_L$ region and a $V_H$ region that are linked with a peptide linker.

39. The antibody, or antigen binding fragment thereof, of embodiment 38, wherein the peptide linker comprises a sequence of GQSSRSSGGGGSSGGGGS (SEQ ID NO: 14); $(GGGGS)_n$ (SEQ ID NO: 15) $(GGGGA)_n$ (SEQ ID NO: 16), or any combination thereof, wherein each n is independently 1-5.

40. The antibody, or antigen binding fragment thereof, of embodiment 38, wherein the peptide linker does not comprise a sequence of GQSSRSSGGGGSSGGGGS (SEQ ID NO: 14).

41. The antibody, or antigen binding fragment thereof, of any one of embodiments 1-40, additionally comprising at least one additional peptide that binds to a different target protein.

42. The antibody, or antigen binding fragment thereof, of embodiment 41, wherein the different target protein is CD3 or CD28.

43. The antibody, or antigen binding fragment thereof, of embodiment 40 or embodiment 41, wherein the at least one additional peptide is an antibody, or antigen binding fragment thereof.

44. The antibody, or antigen binding fragment thereof, of any one of embodiments 1-43, wherein the antibody, or antigen binding fragment thereof, binds to residues E56, N153, Y155, M158, and G159 of the Claudin 18.2 protein.

45. The antibody, or antigen binding fragment thereof, of any one of embodiments 1-44, wherein the antibody, or antigen binding fragment thereof, binds to residues V40, E56, N153, Y155, M158, G159, and G160 of the Claudin 18.2 protein.

46. A nucleic acid molecule encoding an antibody, or antigen binding fragment thereof, of any of the preceding embodiments.

47. A vector comprising the nucleic acid molecule of embodiment 46.

48. A cell comprising the nucleic acid molecule of embodiment 46 or the vector of embodiment 47.

49. A pharmaceutical composition comprising the antibody, or antigen binding fragment thereof, of any one of embodiments 1-45; the nucleic acid molecule of embodiment 46; or the vector of embodiment 47.

50. The pharmaceutical composition of embodiment 49, wherein the pharmaceutical composition is an injectable pharmaceutical composition.

51. The pharmaceutical composition of embodiment 49 or embodiment 50, wherein the pharmaceutical composition is sterile or pyrogen free.

52. The pharmaceutical composition of any one of embodiments 49-51, wherein the pharmaceutical composition is free of antibodies, or antigen binding fragments thereof, that do not bind to Claudin 18.2.

53. A method of treating a tumor or a gastric tumor in a subject, the method comprising administering the Claudin 18.2 antibody, or antigen binding fragment thereof, of any one of embodiments 1-45, or the pharmaceutical composition of any one of embodiments 49-52.

54. The method of embodiment 53, wherein the tumor or gastric tumor is a gastric adenocarcinoma, gastroesophageal junction adenocarcinoma, or pancreatic adenocarcinoma, or non-small cell lung cancer.

55. The method of embodiment 53 or embodiment 54, wherein the subject is a human, a mouse, a sheep, a rat, a rabbit, a shark, a llama, or a chicken.

56. A method of detecting the presence or absence of Claudin 18.2 in a sample, the method comprising contacting the sample with the antibody, or antigen binding fragment thereof, of any one of embodiments 1-45 and detecting the binding to a Claudin 18.2 antigen by the antibody, or antigen binding fragment thereof, wherein the detection of the binding indicates the presence Claudin 18.2; or the absence of the detection of the binding to the Claudin 18.2 indicates the absence of the Claudin 18.2.

57. A method of inducing an immune response against Claudin 18.2 protein in a subject, the method comprising administering a virus-like particle comprising the Claudin 18.2 protein to the subject under conditions sufficient to induce an immune response.

58. The method of embodiment 57, wherein the subject is a human, a mouse, a sheep, a rat, a rabbit, a shark, a llama, or a chicken.

59. A method of generating an antibody, or antigen binding fragment thereof, that binds to a Claudin 18.2 protein, the method comprising administering a virus-like particle comprising the Claudin 18.2 protein on its surface to a subject under conditions to induce an immune response against the Claudin 18.2 protein to generate the antibody, or antigen binding fragment thereof, that binds to the Claudin 18.2 protein.

60. The method of embodiment 59, wherein the subject is a human, a mouse, a sheep, a rat, a rabbit, a shark, a llama, or a chicken.

61. The method of embodiment 59 or embodiment 60, further comprising isolating the antibody that binds to the Claudin 18.2 protein.

62. The method of any one of embodiments 59-61, wherein the antibody, or antigen binding fragment thereof, that is generated binds to an extracellular domain of the Claudin 18.2 protein.

63. The method of any one of embodiments 59-62 further comprising generating a virus-like particle comprising the Claudin 18.2 protein, the method comprising transfecting or transducing a cell with Claudin 18.2 protein and a retroviral gag protein under conditions sufficient to produce the virus-like particle comprising the Claudin 18.2 protein.

64. The method of embodiment 63, wherein the cell is a HEK-293T cell.

65. The method of embodiment 63 or embodiment 64, wherein the gag protein is a MLV gag protein.

66. The method of any one of embodiments 63-65, wherein the retroviral gag protein is Murine Leukemia Virus (MLV), gag, HIV gag, or RSV gag protein.

EXAMPLES

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

Example 1

Generation, Characterization and Analysis of Claudin 18.2 Antibodies and Epitopes Thereof DNA and VLPs were used for immunization and phage display to isolate MAbs against native Claudin 18.2. In order to generate conformationally-sensitive MAbs against Claudin 18.2, an expression plasmid (DNA) encoding Claudin 18.2 was used in combination with a murine leukemia virus (MLV)-based virus-like particles (VLPs) containing human Claudin 18.2 ('Lipoparticles') for the immunization of host cells.

Without being bound by any particular theory, retaining the native structure of multispanning membrane proteins during immunization (and later phage panning steps) is vital for eliciting functionally relevant MAbs, which usually recognize conformational structures on the extracellular membrane protein face. Plasmid DNA can be used to induce the presentation of intact multispanning membrane proteins in their native topology and conformation on the surface of immunization host cells (Eden T, Menzel S, Wesolowski J, Bergmann P, Nissen M, Dubberke G, Seyfried F, Albrecht B, Hagg F, & Koch-Nolte F (2018) A cDNA immunization strategy to generate nanobodies against membrane proteins in native conformation. Frontiers in Immunology 8:1-13, which is hereby incorporated by reference in its entirety). VLPs are non-infectious lipid-enveloped retrovirus particles that can present intact multispanning membrane proteins on their surface with native topology and conformation (Hoffman T L, Canziani G, Jia L, Rucker J, & Doms R W (2000) A biosensor assay for studying ligand-membrane receptor interactions: Binding of antibodies and HIV-1 Env to chemokine receptors. Proc. Natl. Acad. Sci. USA 97(21): 11215-11220; 20; Endres M J, et al. (1997) Targeting of HIV- and SIV-infected cells by CD4-chemokine receptor pseudotypes. Science 278:1462-1464; Balliet J & Bates P (1998) Efficient infection mediated by viral receptors incorporated into retroviral particles. J. Virol. 72:671-676, each of which is hereby incorporated by reference in its entirety). VLPs can capture high levels of structurally intact GPCRs, ion channels, and transporters when the VLPs bud from the plasma membrane, and VLPs are potent immunogens due to their particulate structure and multivalent epitope organization (Ludwig C & Wagner R (2007) Virus-like particles-universal molecular toolboxes. Curr Opin Biotechnol 18(6): 537-545; Saitoh R, et al. (2007) Viral envelope protein gp64 transgenic mouse facilitates the generation of monoclonal antibodies against exogenous membrane proteins displayed on baculovirus. J Immunol Methods 322(1-2):104-117, each of which is hereby incorporated by reference in its entirety).

The level of incorporation of Claudin 18.2 into the VLPs was 600 pmol/mg (specific protein amount per mg total protein). For comparison, commercial membrane preparations generally contain 1 to 10 pmol/mg (e.g. from Perkin Elmer or Millipore-Sigma) and intact cells generally contain 0.1 to 1 pmol/mg, so the VLPs concentrated Claudin 18.2 by approximately 10-100 fold (Lai X (2013) Reproducible method to enrich membrane proteins with high purity and high yield for an LC-MS/MS approach in quantitative membrane proteomics. Electrophoresis 34(6):809-817; Bryk A H & Wisniewski J R (2017) Quantitative Analysis of Human Red Blood Cell Proteome. J Proteome Res 16(8): 2752-2761, each of which is hereby incorporated by reference in its entirety).

The conservation of Claudin 18.2 informed the choice to use chickens as the host for immunization with human Claudin 18.2 (hsClaudin 18.2) VLPs. Claudin 18.2 is highly conserved among mammals, with hsClaudin 18.2 sharing >90% overall sequence identity with the mouse ortholog. Importantly, a specific antibody against Claudin 18.2 needs to discriminate between the Claudin 18.2 (cancer specific) and Claudin 18.1 (expressed in normal tissues) isoforms (splice variants). Although the structure of Claudin 18.2 has not been solved, topology prediction programs, (TOPCONS), and modeling on related Claudin structures, (Claudin 3, 9, 15), allowed for the prediction of the position and size of the Claudin 18.2 extracellular loops. Claudin 18.2 has been predicted to have two extracellular loops: loop 1 (position 26 aa-80 aa), and loop 2 (position 138-a-171 aa). All of the amino acid sequence differences between Claudin 18.1 and Claudin 18.2 are located in the predicted extracellular region 1 (position 26 aa 80 aa). A comparative alignment of the 55 amino acids in the predicted extracellular loop 1 region of hsClaudin 18.2 showed no differences with mouse (mm) Claudin 18.2, but 3 amino acid differences with chicken Claudin 18.2.

Generating antibodies against highly conserved proteins is difficult due to immune tolerance, which severely limits both the magnitude of the humoral response and the diversity of epitopes recognized. In contrast, birds have a large evolutionary distance from mammals, so are capable of generating immune responses to human proteins that are highly conserved in mammals. Also, chicken immunoglobulin (IgY) is highly similar to mammalian IgG but with only a single VH and VL framework, making phage library creation and downstream humanization ideal over using murine antibodies (Finlay W J, Bloom L, Varghese S, Autin B, & Cunningham O (2017) Optimized Generation of High-Affinity, High-Specificity Single-Chain Fv Antibodies from Multi-Antigen Immunized Chickens. Methods Mol Biol 1485:319-338; Finlay W J, et al. (2017) Phage Display: A Powerful Technology for the Generation of High-Specificity Affinity Reagents from Alternative Immune Sources. Methods Mol Biol 1485:85-99, each of which is hereby incorporated by reference in its entirety).

Based on this analysis, chickens were selected for immunization with hsClaudin 18.2 DNA and VLPs to generate a robust immune response against hsClaudin 18.2. Antibodies were then identified that selectively bind to Claudin 18.2.

Identification of MAbs that Bind Selectively to Claudin 18.2 Protein and do not Selectively Bind to Claudin 18.2 Protein To confirm the binding of the MAbs against Claudin 18.2 on human cells, the binding of three non-limiting humanized antibodies MAb1 (IM-44-09B03-1HB), MAb2 (IM-44-01E10-1HA), and MAb3 (IM-44-05H06-1HD) against Claudin 18.2 was assessed by high-throughput flow cytometry for HEK-293T cells expressing Claudin 18.2 (FIG. 1). HEK-293T cells were transfected by $CaPO_4$ with hsCLDN18.2 and control plasmids in T-225 flasks (Falcon) at 14,000,000 cells/flask. At 18-24 hours post transfection, cells were stained with anti-CLAUDIN 18.2 MAb1, MAb2, or MAb3 (purified IgG, 2 μg/mL) followed by APC-labelled goat anti-human antibody (1:500). Fluorescence was detected using an Intellicyt high-throughput flow cytometer (HTFC; Intellicyt, Albuquerque, NM). A positive control, zolbetuximab, was also used (FIG. 1: labeled as "Clinical Benchmark"). All three of the humanized antibodies MAb1 (IM-44-09B03-1H1B), MAb2 (IM-44-01E10-1HA), and MAb3 (IM-44-05H06-1HD) demonstrated strong reactivity with Claudin 18.2 (FIG. 1).

Figure 2A:
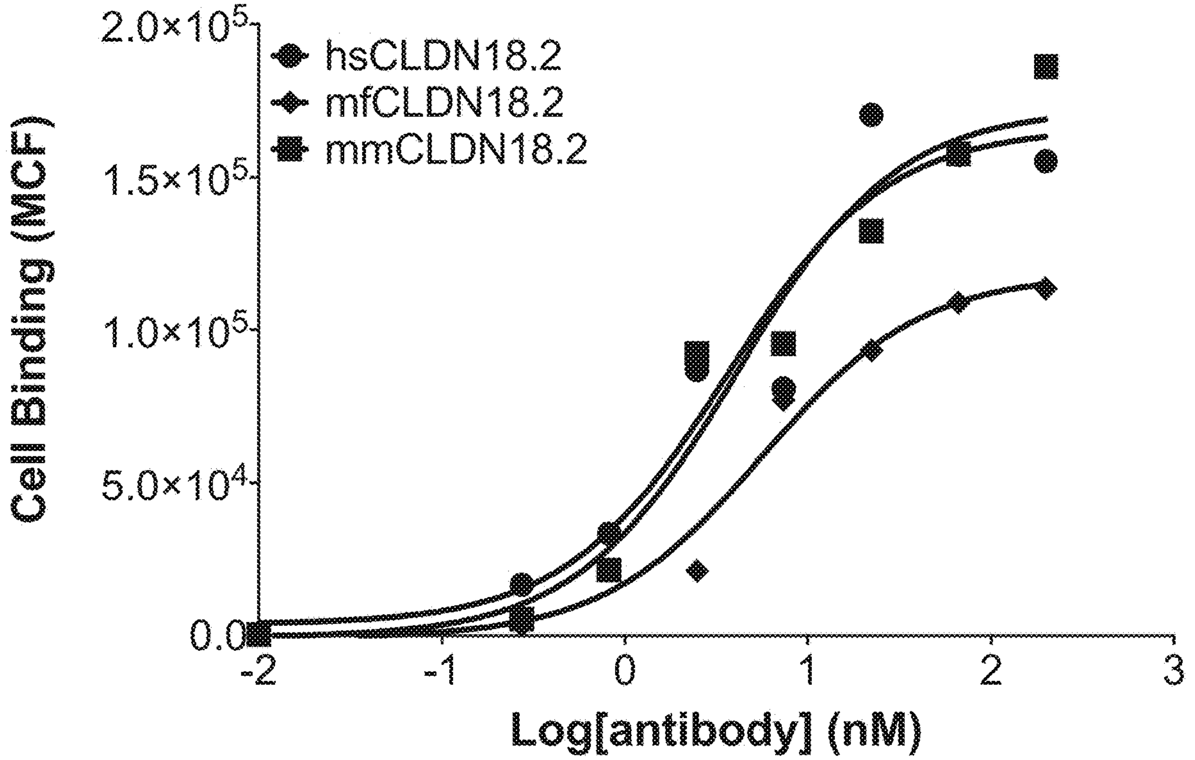
FIG. 2A illustrates the specificity of MAb1 (IM-44-09B03-1H1B) for human, cynomolgus, and mouse forms of Claudin 18.2.
Figure 2B:
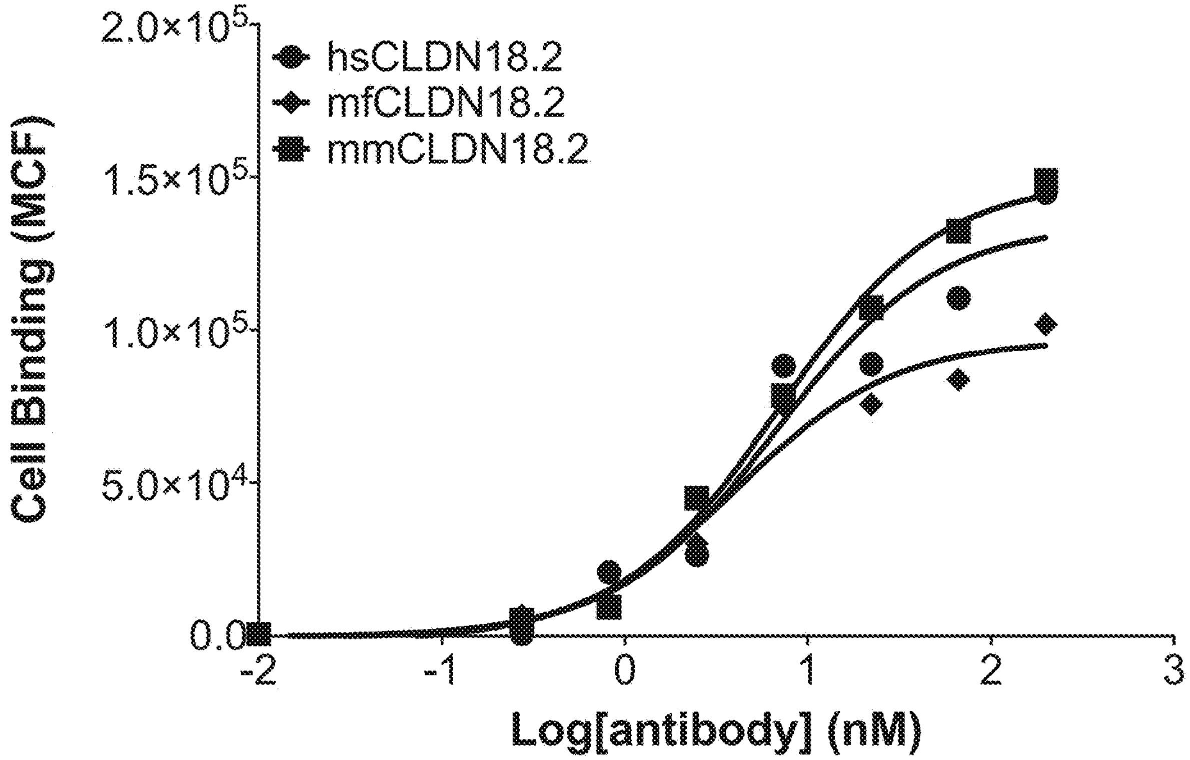
FIG. 2B illustrates the specificity of MAb2 (IM-44-01E10-1HA) for human, cynomolgus, and mouse forms of Claudin 18.2.
Figure 2C:
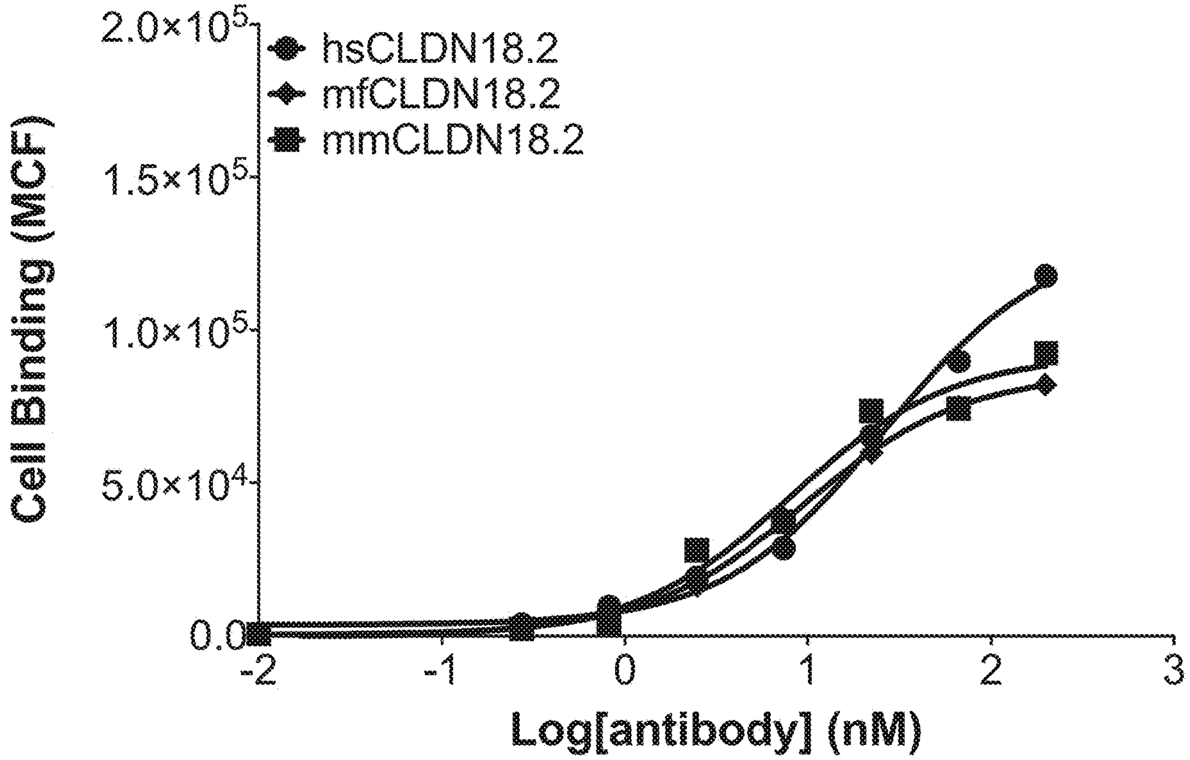
FIG. 2C illustrates the specificity of MAb3 (IM-44-05H06-1HD) for human, cynomolgus, and mouse forms of Claudin 18.2.

The specificity of the three non-limiting humanized antibodies MAb1 (IM-44-09B03-1H1B), MAb2 (IM-44-01E10-1HA), and MAb3 (IM-44-05H06-1HD) was then measured against the human (hm), cynomolgus (mf), and mouse (mm) forms of Claudin 18.2 by high-throughput flow cytometry (FIG. 2A, FIG. 2B, and FIG. 2C). HEK-293T cells were transfected by $CaPO_4$ with human CLDN18.2, cynomolgus CLDN18.2, and mouse CLDN18.2 and control plasmids in T-225 flasks (Falcon) at 14,000,000 cells/flask. At 18-24 hours post transfection, cells were stained with the anti-CLAUDIN 18.2 MAb1 (IM-44-09B03-1H1B), MAb2 (IM-44-01E10-1HA), and MAb3 (IM-44-05H06-1HD) (purified IgG, 2 μg/mL) followed by APC-labelled goat anti-human antibody (1:500). Fluorescence was detected using an Intellicyt high-throughput flow cytometer (HTFC; Intellicyt, Albuquerque, NM)."). All three of the humanized antibodies MAb1 (IM-44-09B03-1H1B), MAb2 (IM-44-01E10-1HA), and MAb3 (IM-44-05H06-1HD) demonstrated strong reactivity with against the huma, cynomolgus, and mouse forms of Claudin 18.2 (FIG. 2A, FIG. 2B, and FIG. 2C).

Figure 3A:
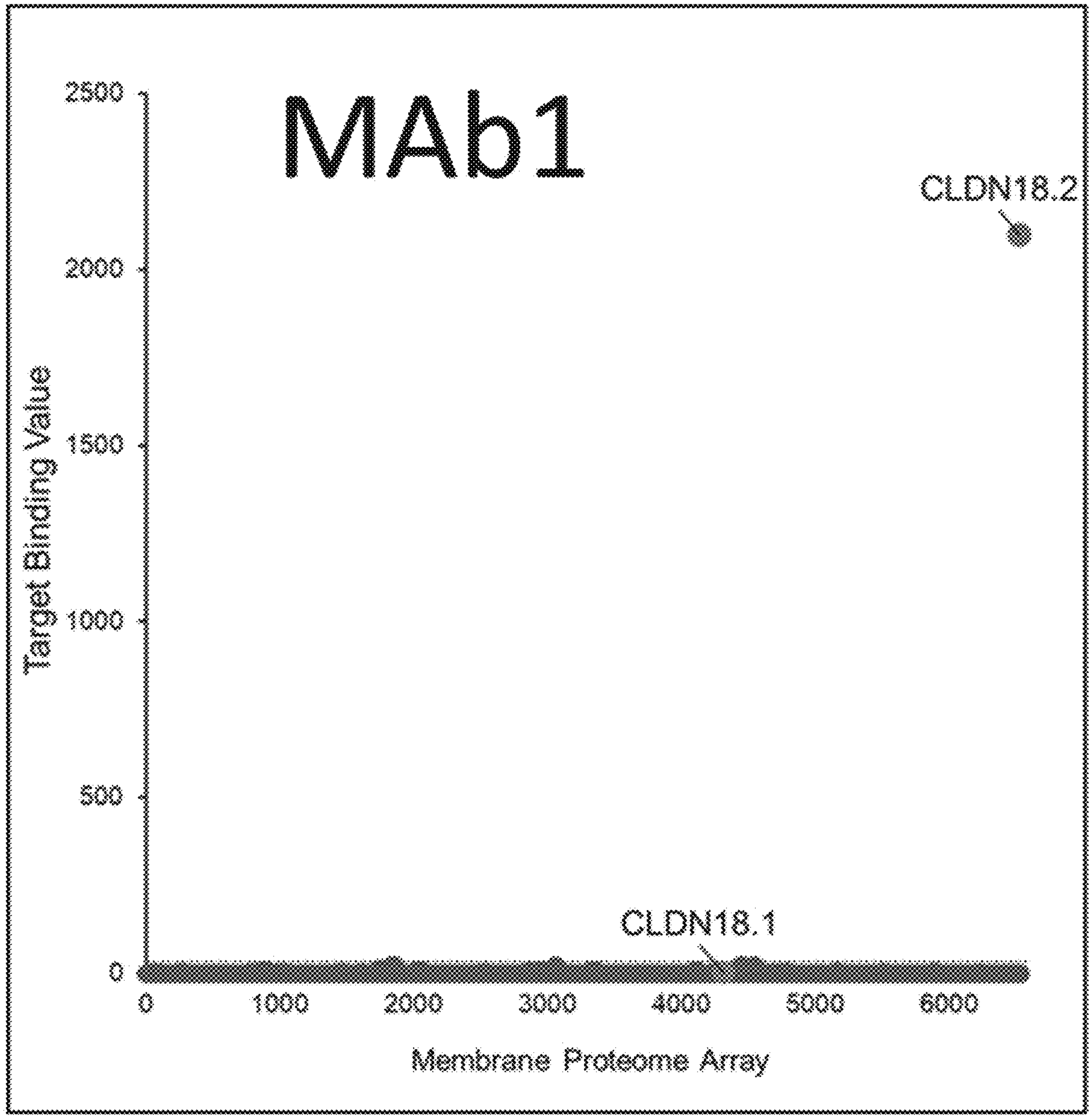
FIG. 3A illustrates the specificity of the humanized antibody MAb1 (IM-44-09B03-1H1B) against Claudin 18.2 over Claudin 18.1. MAb1 (IM-44-09B03-1H1B) did not show cross-reactivity against Claudin 18.1.
Figure 3B:
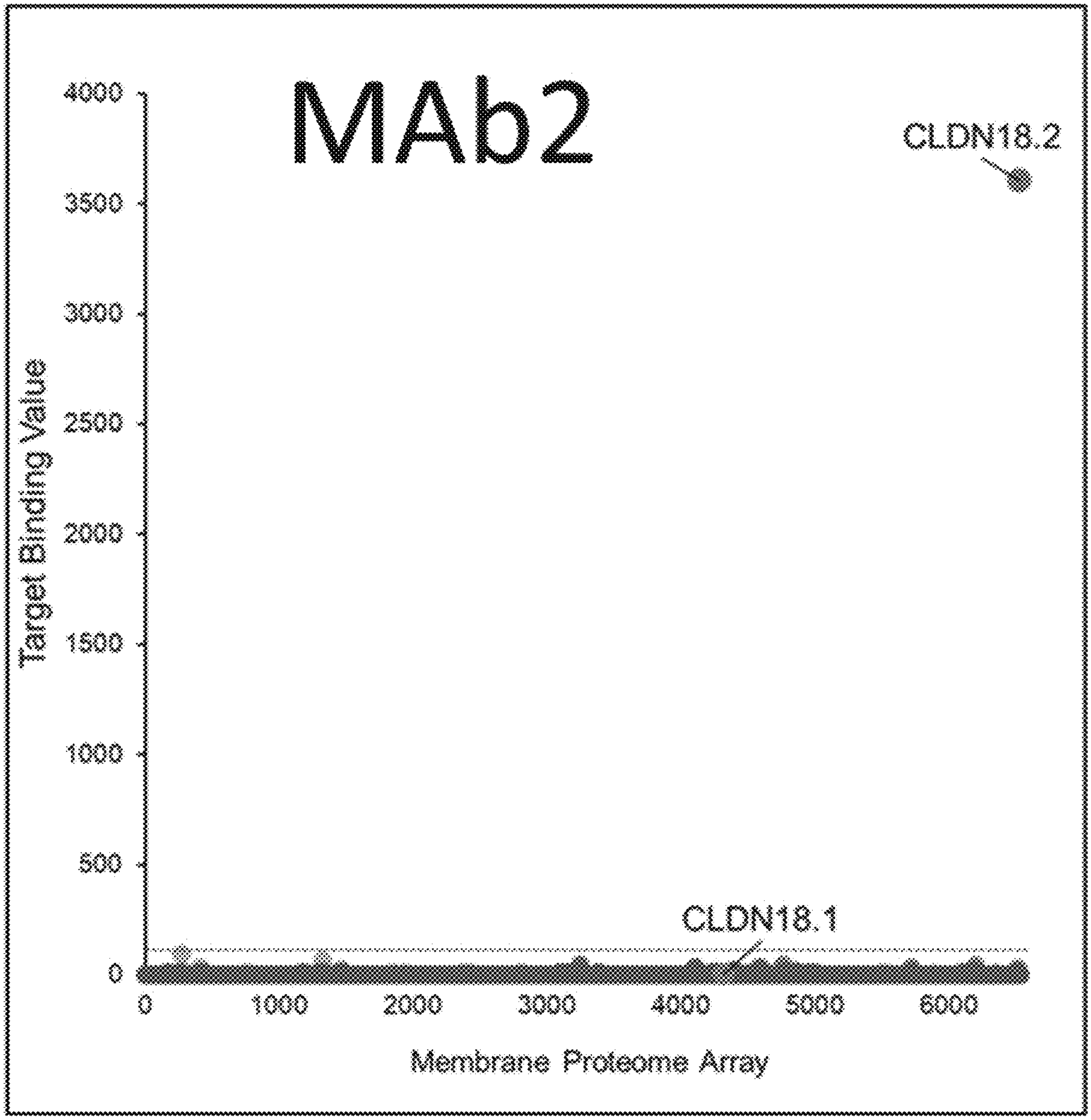
FIG. 3B illustrates the specificity of the humanized antibody MAb2 (IM-44-01E10-1HA) against Claudin 18.2 over Claudin 18.1. MAb2 (IM-44-01E10-1HA) did not show cross-reactivity against Claudin 18.1.
Figure 3C:
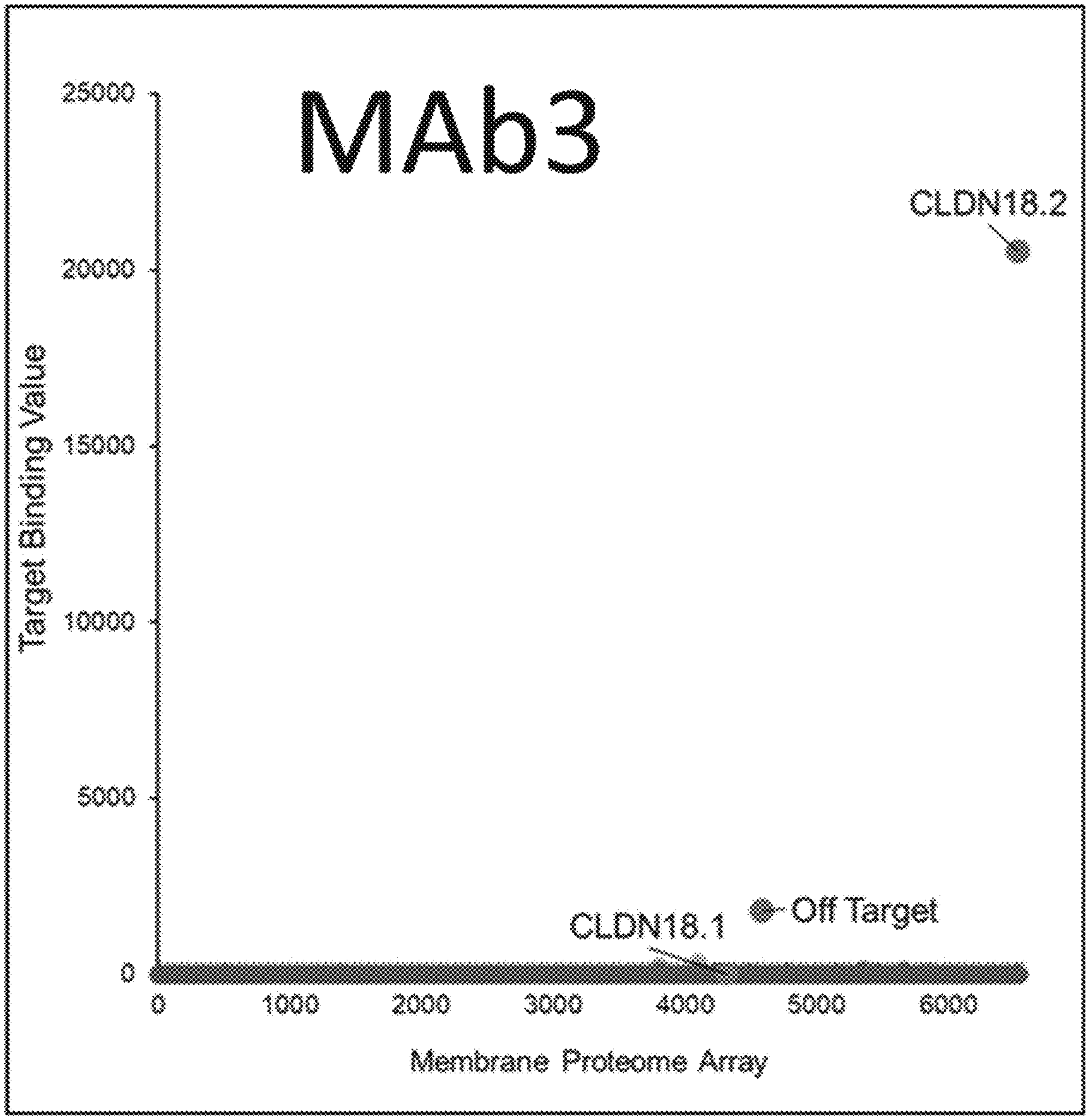
FIG. 3C illustrates the specificity of the humanized antibody MAb3 (IM-44-05H06-1HD) against Claudin 18.2 over Claudin 18.1. MAb3 (IM-44-05H06-1HD) did not show cross-reactivity against Claudin 18.1.

The specificity of the antibodies MAb1 (IM-44-09B03-1H1B), MAb2 (IM-44-01E10-1HA), and MAb3 (IM-44-05H06-1HD) was next tested against Claudin 18.1 and other members of the membrane proteome. The specificity against Claudin 18.2 over Claudin 18.1 and to other members of the membrane proteome was measured by binding to a membrane proteome array (MPA), consisting of 5,300 human membrane proteins expressed in human HEK-293 cells (FIG. 3A, FIG. 3B, and FIG. 3C). Cells were permeabilized with 0.1% saponin, antibody was added to the MPA at either 5 or 20 ug/mL, and binding across the protein library was measured using high-throughput flow cytometry (Intellicyt HTFC) using a fluorescent secondary antibody. None of the antibodies show cross-reactivity against CLDN18.1 or any other member of the membrane proteome, which demonstrates the high specificity of these antibodies against Claudin 18.2.

Figure 4A:
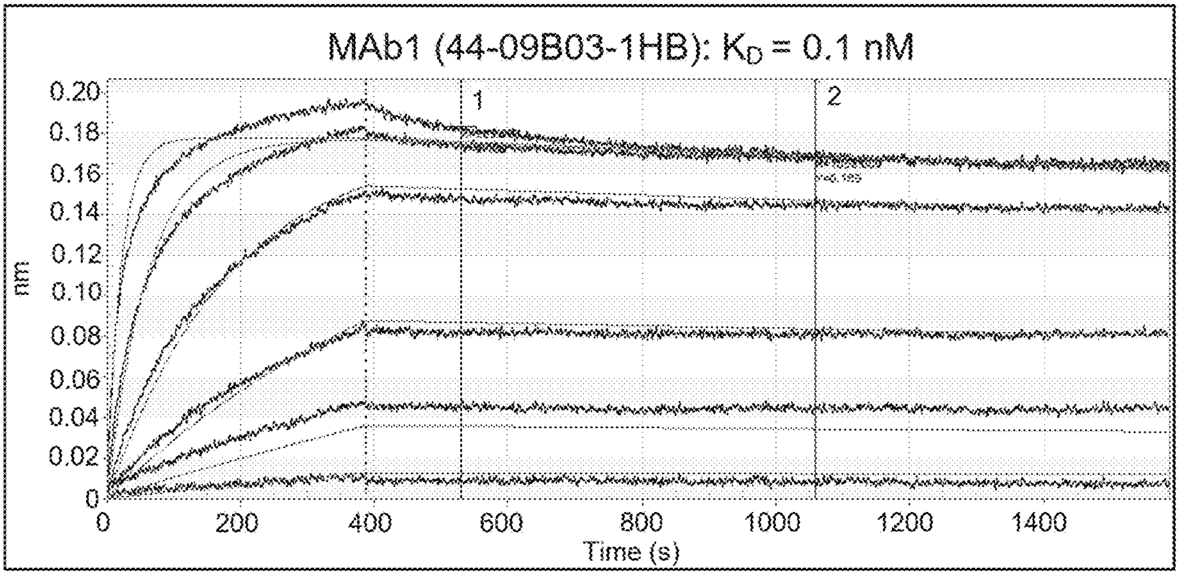
FIG. 4A depicts exemplary biosensor data used for determination of the dissociation constant ($K_D$) of the humanized antibody MAb1 (IM-44-09B03-1H1B) against Claudin 18.2.
Figure 4B:
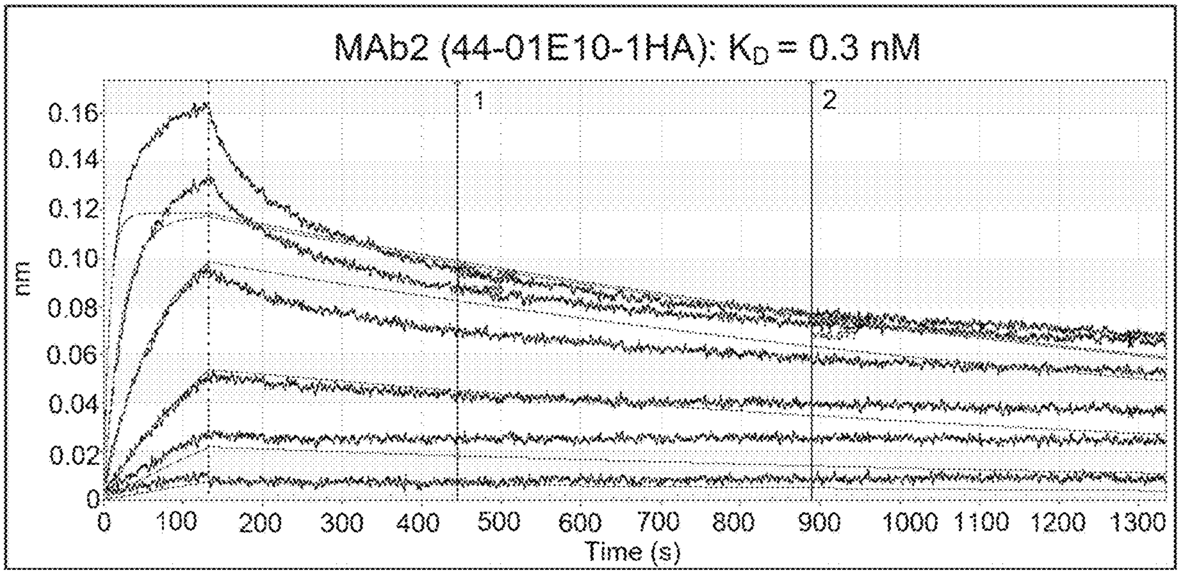
FIG. 4B depicts exemplary biosensor data used for determination of the dissociation constant ($K_D$) of the humanized antibody MAb2 (IM-44-01E10-1HA) against Claudin 18.2.
Figure 4C:
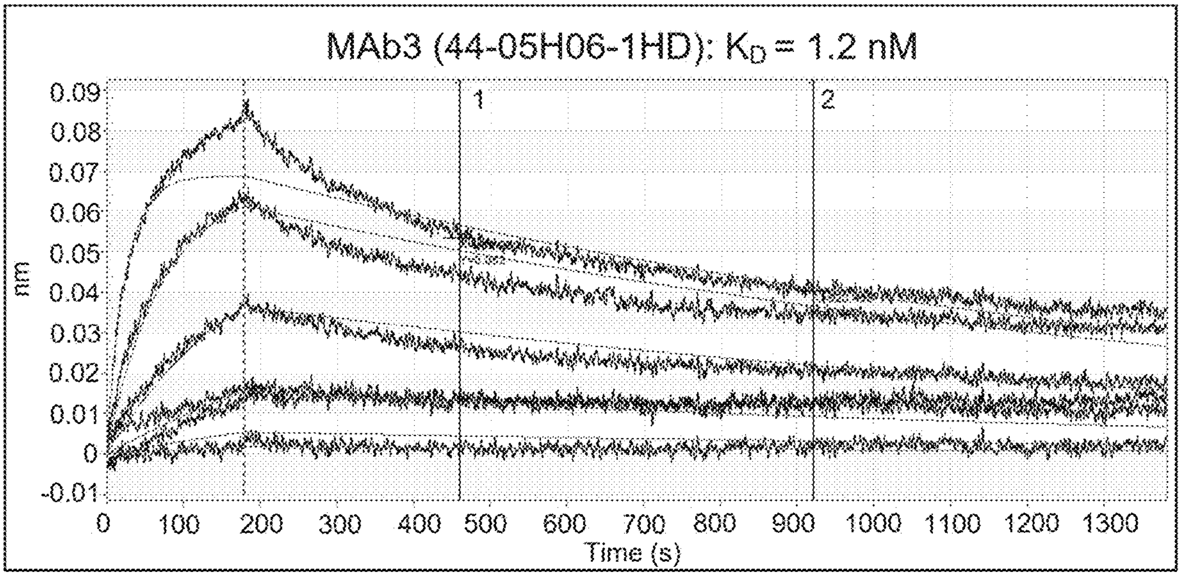
FIG. 4C depicts exemplary biosensor data used for determination of the dissociation constant ($K_D$) of the humanized antibody MAb3 (IM-44-05H06-1HD) against Claudin 18.2.
Figure 4D:
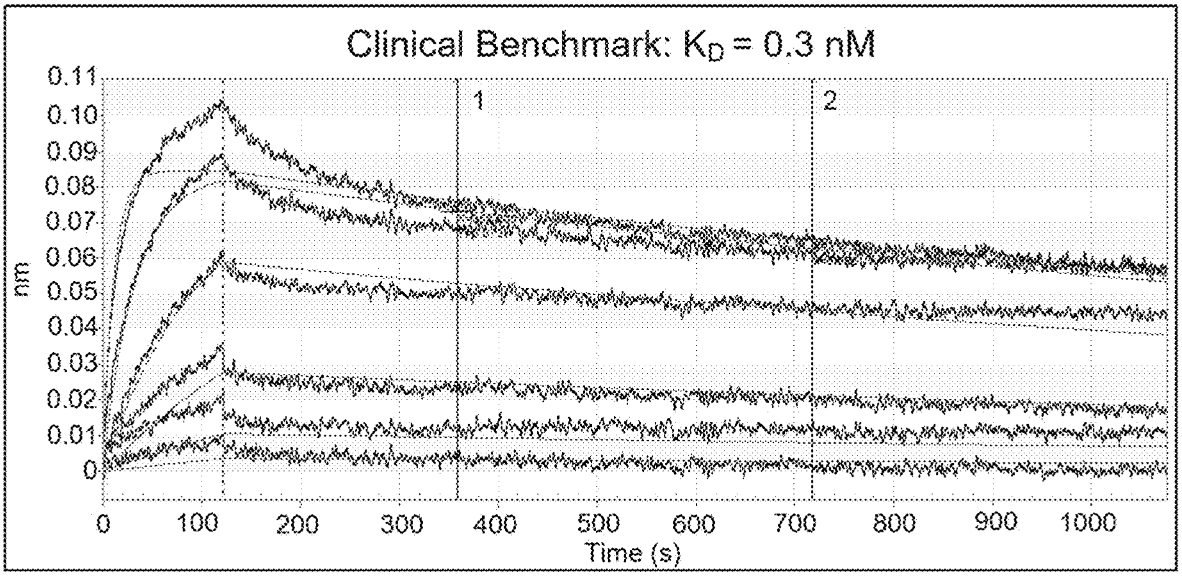
FIG. 4D depicts exemplary biosensor data used for determination of the dissociation constant ($K_D$) of the positive control, which is labeled as "Clinical Benchmark," against Claudin 18.2.

To further characterize the binding activities of the selected MAbs, the kinetics of MAb binding to conformationally native Claudin 18.2 were assessed using bio sensor analysis. For this, biotinylated hsCLDN18.2-VLPs were immobilized onto biosensor tips, and the binding affinity and kinetics of MAb1 (IM-44-09B03-1H1B), MAb2 (IM-44-01E10-1HA), and MAb3 (IM-44-05H06-1HD) were measured using biolayer interferometry. The dissociation constant ($K_D$) for MAb1, MAb2, and MAb3 were measured to be 0.1 nM (FIG. 4A), 0.3 nM (FIG. 4B), and 1.2 nM (FIG. 4C), respectively. A positive control, zolbetuximab, was also used (FIG. 4D: labeled as "Clinical Benchmark"), which demonstrated a $K_D$ of 0.3 nM.

Figure 6A:
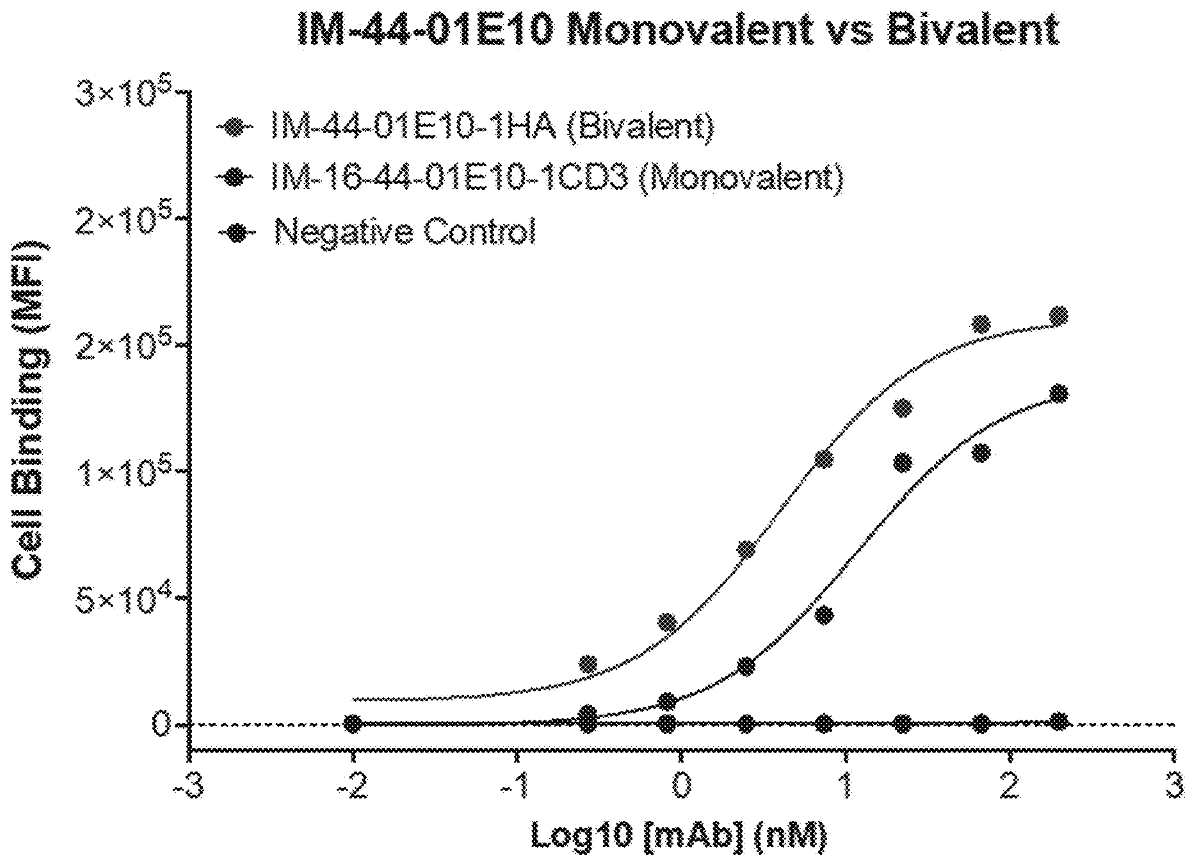
FIG. 6A illustrates monovalent verses bivalent binding of MAb1.
Figure 6B:
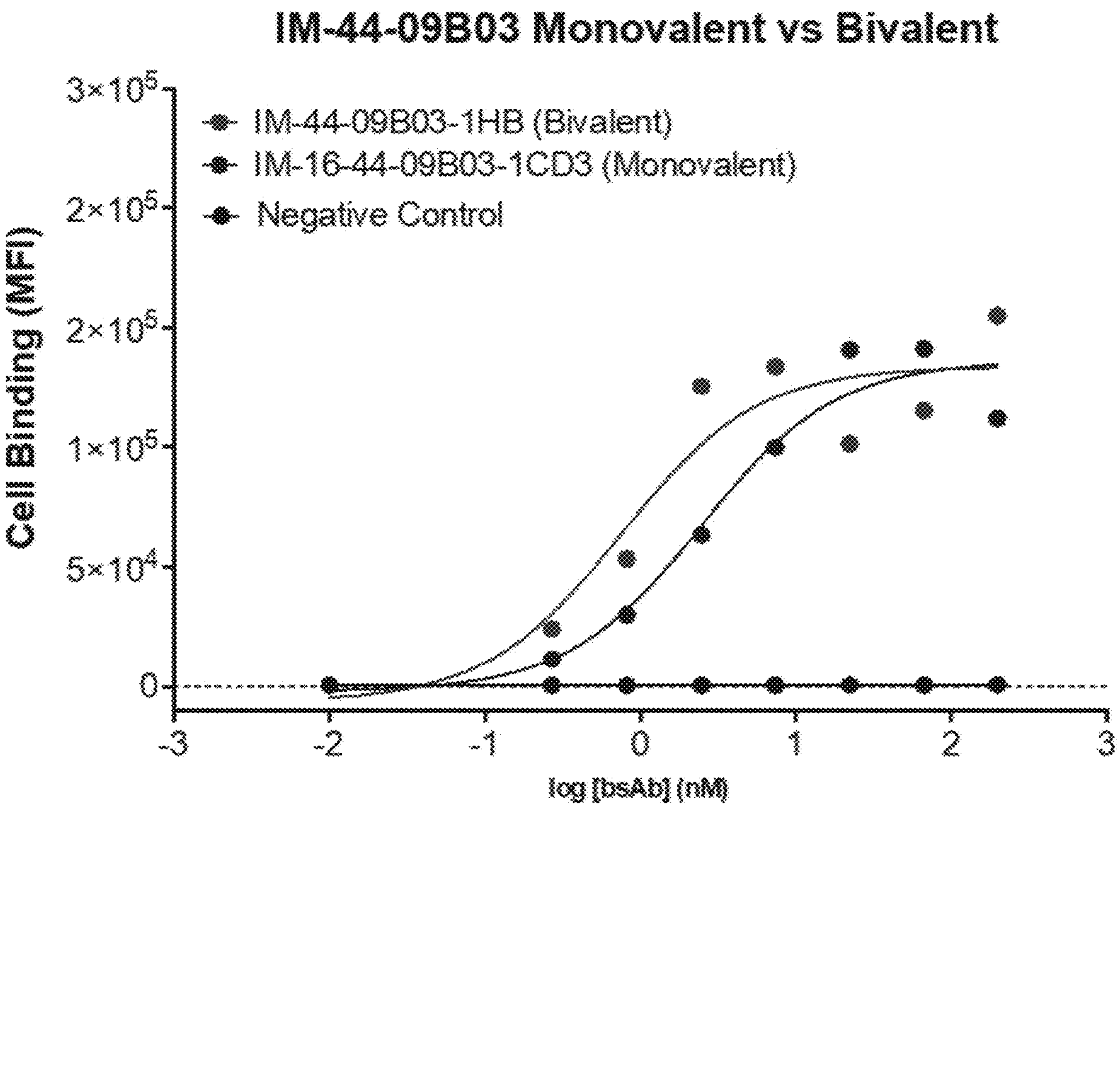
FIG. 6B illustrates monovalent verses bivalent binding of MAb2.
Figure 6C:
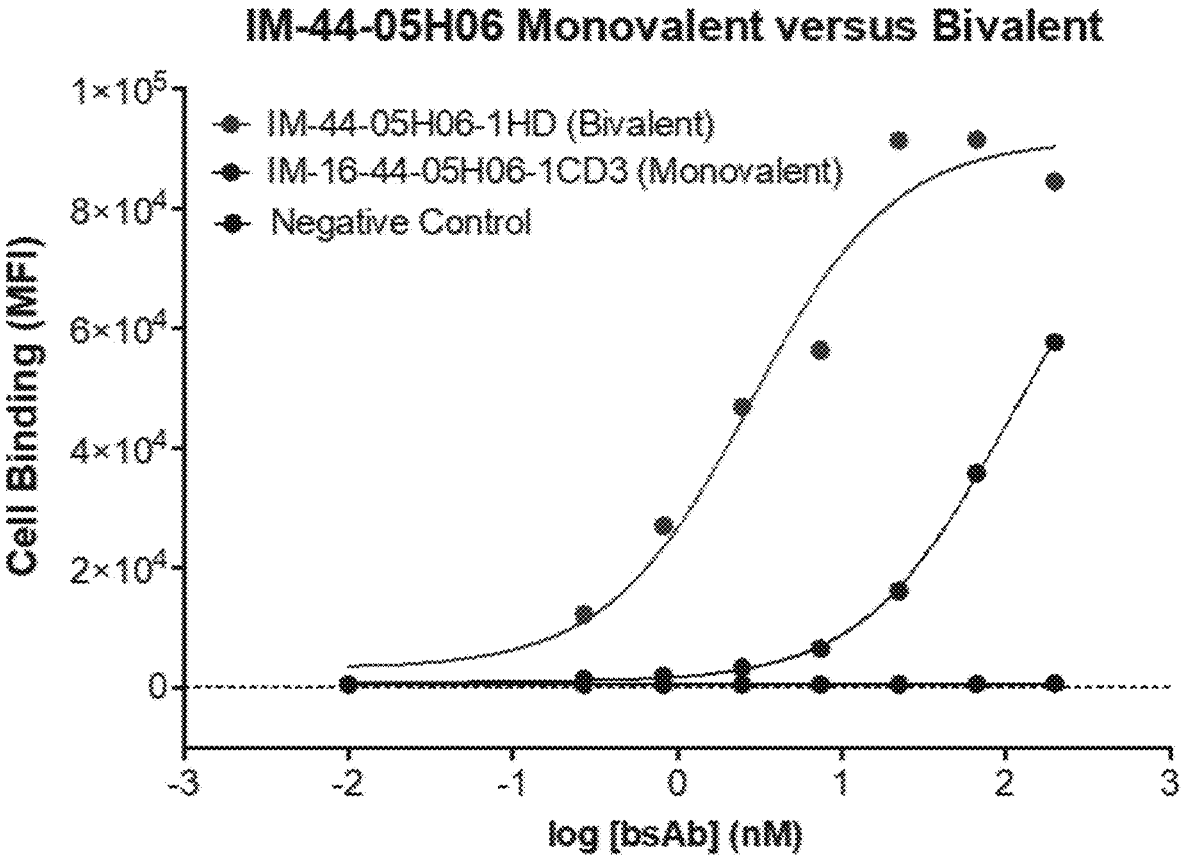
FIG. 6C illustrates monovalent verses bivalent binding of MAb3.

To further characterize the binding activities of the selected MAbs, the binding to conformationally native Claudin 18.2 was assessed for the bivalent antibodies MAb1 (IM-44-09B03-1HIB), MAb2 (IM-44-01E10-1HA), and MAb3 (IM-44-05H06-1HD), against their monovalent forms. MAb1 (IM-44-01E10-1HA) (FIG. 6A) and MAb2 (IM-44-09B03-1H1B) (FIG. 6B) both demonstrated low avidity with monomeric binding comparable to bivalent binding. MAb3 (IM-44-05H06-1HD) (FIG. 6C) demonstrated high avidity with significantly lower monovalent binding compared to bivalent binding.

Mapping of MAb Epitopes

The residues required for binding of each MAb were determined using shotgun mutagenesis compre-hensive alanine scanning (Davidson E & Doranz B J (2014) A High-Throughput Shotgun Mutagenesis Approach to Mapping B-cell Antibody Epitopes. Immunology, which is hereby incorporated by reference in its entirety). All residues of hsCLDN18.2 were individually mutated to alanine, with existing alanine residues changed to serine residues. The entire mutation library was transfected into human HEK-293T cells in a 384-well array format and assessed for immunoreactivity using high-throughput flow cytometry.

Figure 5A:
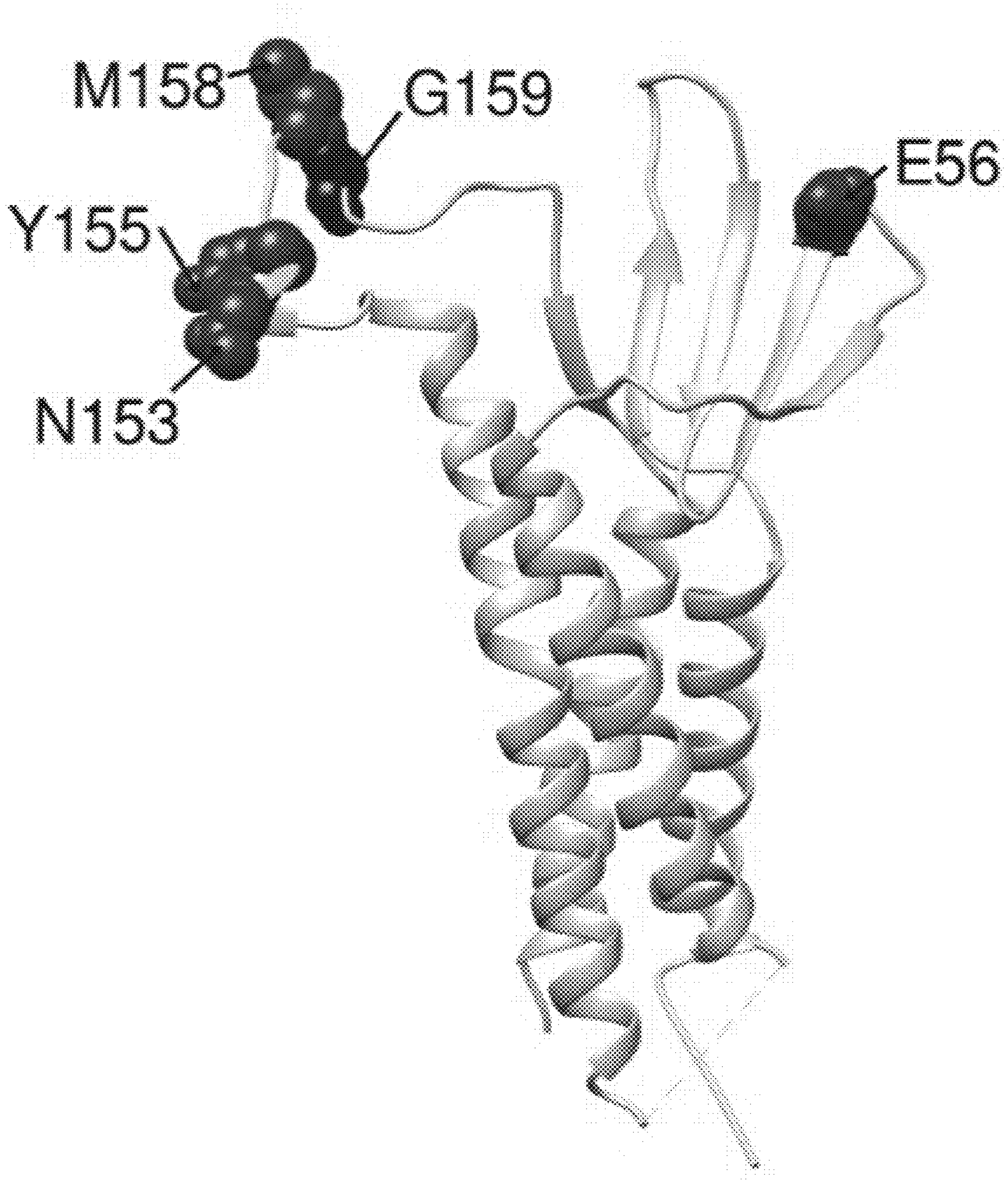
FIG. 5A illustrate the residues of Claudin 18.2 that are critical for the binding of the humanized antibody MAb1 (IM-44-09B03-1H1B), as determined by epitope mapping.
Figure 5B:
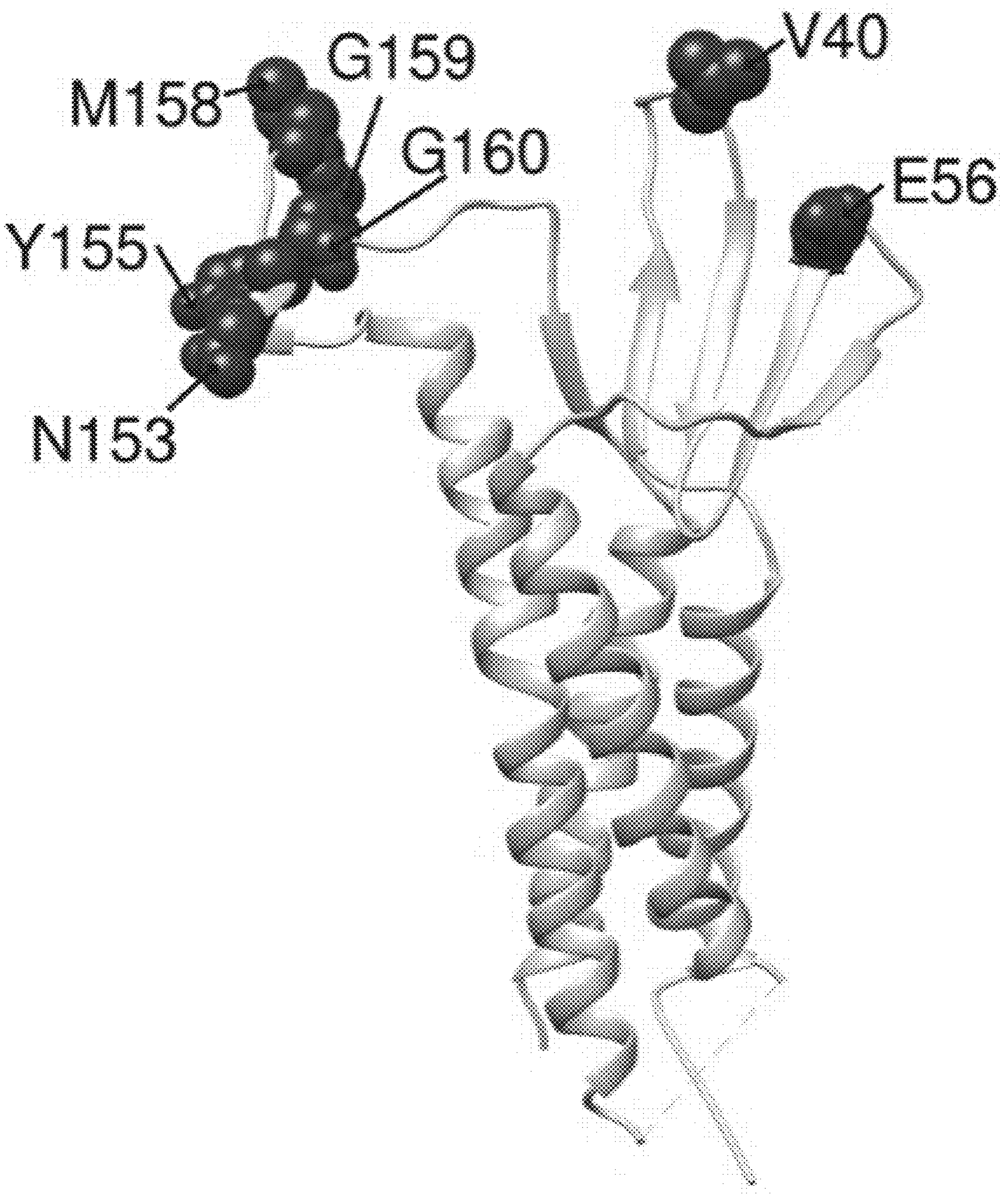
FIG. 5B illustrates the residues of Claudin 18.2 that are critical for the binding of the humanized antibody MAb2 (IM-44-01E10-1HA), as determined by epitope mapping.
Figure 5C:
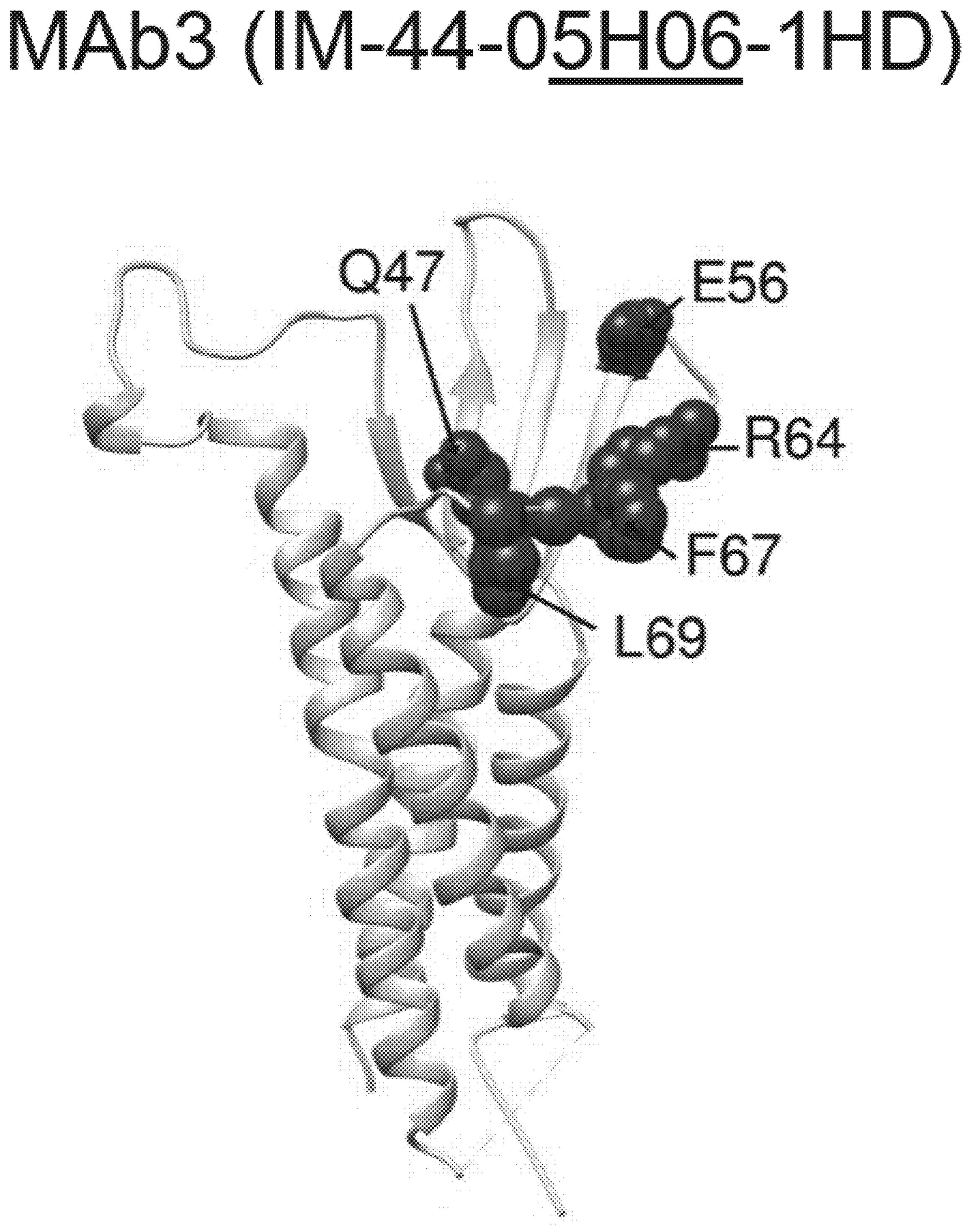
FIG. 5C illustrates the residues of Claudin 18.2 that are critical for the binding of the humanized antibody MAb3 (IM-44-05H06-1HD), as determined by epitope mapping.
Figure 5D:
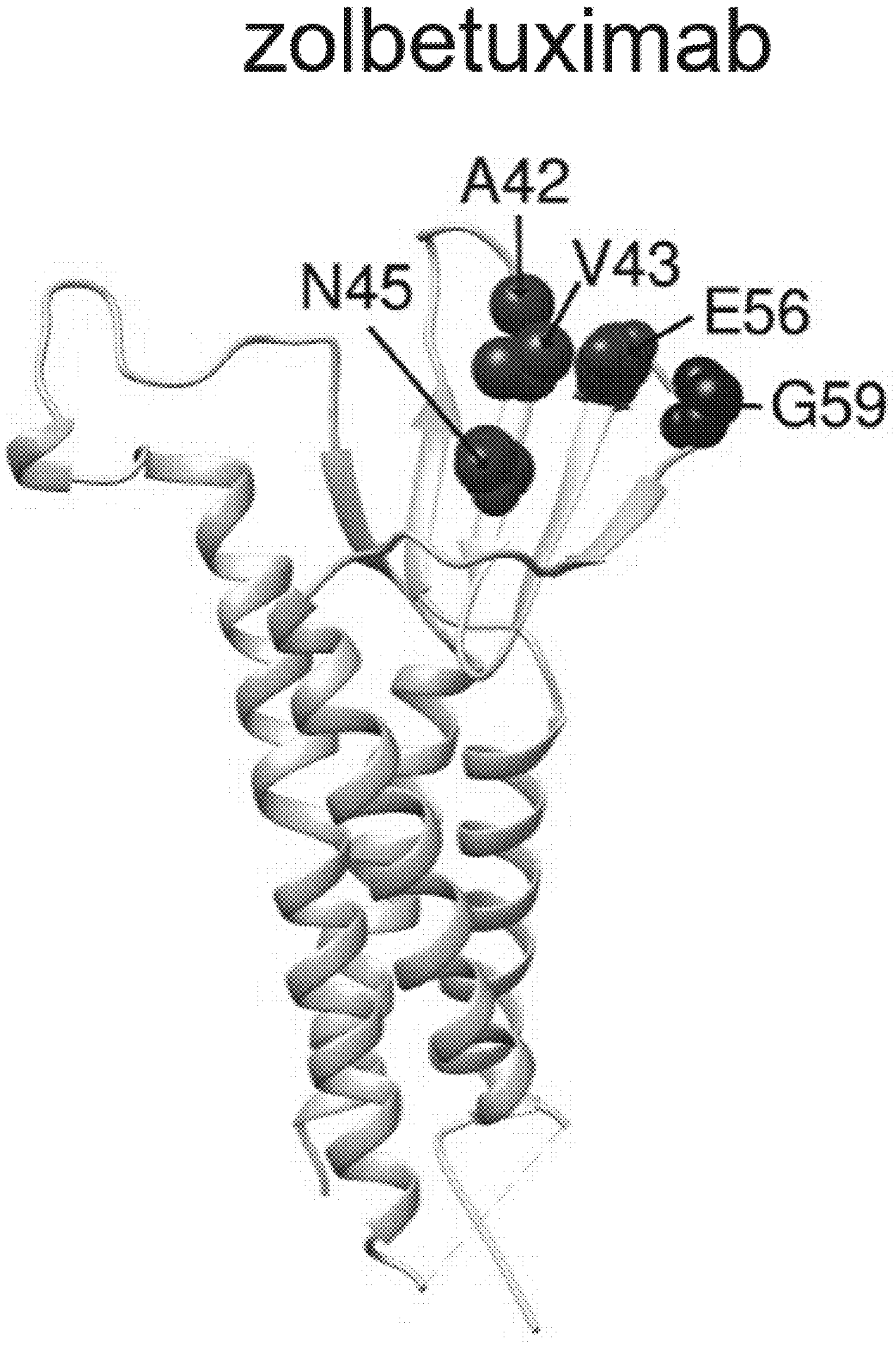
FIG. 5D illustrates the residues of Claudin 18.2 that are critical for the binding of the positive control ("Clinical Benchmark;" zolbetuximab), as determined by epitope mapping.

MAb epitopes were obtained by testing each MAb against the entire mutation library, identifying residues whose mutation to alanine impaired binding relative to wild type Claudin 18.2. Residues critical for each MAb epitope were identified as those where Claudin 18.2 mutations resulted in less than 20% reactivity for the MAb of interest (relative to wild type Claudin 18.2) yet greater than 70% wild type binding by a reference MAb. Residues were further validated as critical by comparing their reactivities across all MAbs tested to verify that the mutation did not globally disrupt the binding of diverse MAbs. The location and exposure of the identified residues was also considered as an indication of their potential for direct interaction with each MAb. Identified residues are 'hot-spots' that generally represent the most energetically important amino acids contributing to the binding of each MAb. As a control, epitope mapping of the commercial MAb zolbetuximab identified the residues N45, A42, V43, E56, and G59 as its critical epitope residues (FIG. 5D). Mapping of MAb1 (IM-44-09B03-1HIB) identified E56, N153, Y155, M158, and G159 as its critical epitope residues (FIG. 5A). Mapping of MAb2 (IM-44-01E10-1HA) identified V40, E56, N153, Y155, M158, G159, and G160 as its critical epitope residues (FIG. 5B). Mapping of MAb3 (IM-44-05H06-1HD) identified Q47, E56, R64, F67, and L69 as its critical epitope residues (FIG. 5C).

General Materials and Methods

Isolation of Claudin 18.2 MAbs

VLPs displaying Claudin 18.2 proteins (commercially referred to as 'Lipoparticles') were produced by co-transfection of HEK-293T cells with plasmids carrying hsCLAUDIN 18.2 genes and the retroviral (MLV) Gag protein, as previously described (Hoffman T L, Canziani G, Jia L, Rucker J, & Doms R W (2000) A biosensor assay for studying ligand-membrane receptor interactions: Binding of antibodies and HIV-1 Env to chemokine receptors. Proc. Natl. Acad. Sci. USA 97(21):11215-11220; Willis S, et al. (2008) Virus-like particles as quantitative probes of membrane protein interactions. Biochemistry 47(27):6988-6990, each of which is hereby incorporated by reference in its entirety). 'Null' VLPs were produced the same way but without transfection of a specific receptor.

A scFv phage display library was constructed from B cells of a hsClaudin 18.2 VLP-immunized chicken that showed serum reactivity with Claudin 18.2 by flow cytometry, as previously described (Finlay W J, Bloom L, Varghese S, Autin B, & Cunningham O (2017) Optimized Generation of High-Affinity, High-Specificity Single-Chain Fv Antibodies from Multi-Antigen Immunized Chickens. Methods Mol Biol 1485:319-338, which is hereby incorporated by reference in its entirety.) For panning, the phage library (2E9) was allowed to bind to wells coated with Claudin 18.2 VLPs (for positive selection) or null VLPs (for de-selection). Bound phage was trypsin-eluted and amplified through three rounds of panning before screening the clones for binding to Claudin 18.2. Individual scFv peripreps were prepared from single colonies by induction with 1 mM IPTG (iso-propyl-β-D-thiogalactopyranoside) at 28° C. overnight followed by extraction of the periplasmic fraction by freeze-thaw, and then screened for hsClaudin 18.2-specific binding by ELISA using VLPs.

For screening phage clones by periprep ELISA, purified hsClaudin 18.2-displaying VLPs were coated on a 96-well white, flat-bottom microtiter plate overnight at 4° C. using 0.25 μg of protein per well in 0.1 M sodium bicarbonate buffer, pH 8.6. The wells were washed with PBS and blocked with 4% PBS−/− with 4% milk (PBSM) for 1 h. scFv in 4% PBSM were added to each well, and the plate was incubated for 1 h at 37° C. with gentle agitation. The scFv solution was discarded, and the plate was washed 3 times with PBS plus 0.01% Tween 20. To detect bound scFv, a 1:5,000 dilution of anti-human Fd conjugated with horseradish peroxidase (HRP; Southern Biotech, Birmingham, AL) in 4% PBSM was added to the wells, and the plate was incubated at room temperature (22° C.) for 30 min with gentle agitation. The plate was washed 3 times with PBS plus 0.01% Tween 20 and developed according to the manufacturer's instructions (Super Signal West Pico; Thermo Scientific, Waltham, MA). Negative controls included a buffer blank (no antigen) and a non-specific antigen.

Candidate scFv were converted to human IgG1-Fc format for production in HEK-293T cells. Briefly, the scFv region was PCR amplified and cloned using infusion cloning (Clontech) in-frame with a leader sequence and the Fc fragment of human IgG1 to create a scFv-Fc gene. scFv-Fc constructs were transfected into HEK-293T cells by calcium phosphate precipitation. Secreted scFv-Fc were purified from the culture media at 48 h to 72 h post-transfection by protein A chromatography, followed by concentration and buffer exchange against PBS. Quantification of the purified scFv-Fc was performed using a bicinchoninic acid (BCA) assay (Thermo Scientific, Waltham, MA).

Biosensor Binding Kinetics

All biosensor studies were performed in PBS buffer supplemented with 1 mg/mL bovine serum albumin (BSA; PBS-B) at 25° C. using a ForteBio Octet Red biosensor system (Pall-ForteBio, Inc., Menlo Park, CA). Streptavidin (SA) biosensor tips were loaded with biotinylated hsClaudin 18.2 VLPs (diluted to 20 μg/mL in PBS-B) for 45 minutes and allowed to stabilize for 10 minutes. Antibody binding and dissociation kinetics were determined for serial dilutions of antibody in PBS-B starting at 20 μg/mL. Antibody association was measured for 5 minutes followed by dissociation for up to 45 minutes in buffer. Non-specific binding was assessed using sensor tips with VLPs containing only endogenous proteins (Null VLPs). Data analysis was performed using the Octet data analysis program (v8.1; ForteBio) using a standard 1:1 binding model.

Flow Cytometry

HEK-293T cells were transfected by $CaPO_4$ with plasmids in 6-well culture plates (Falcon) at 750,000 cells/well. At 18-24 hours post transfection, cells were stained with anti-V5 and anti-CLAUDIN 18.2 MAbs (purified IgG, 2 μg/mL) followed by biotinylated goat anti-mouse or human antibody (1:500) and streptavidin-PerCP (1:500). Fluorescence was detected using an Intellicyt high-throughput flow cytometer (HTFC; Intellicyt, Albuquerque, NM).

Membrane Proteome Array (MPA) Specificity Testing

The MPA is Integral Molecular's cell-based platform of 4,571 different human membrane proteins, each over-expressed in live cells from expression plasmids that are individually transfected in separate wells of a 384-well plate (Huston-Paterson D J, Banik S S, & Doranz B J (2016) Screening the Membrane Proteome. Genetic Engineering & Biotechnology News (September 1):18-19, which is hereby incorporated by reference in its entirety). The entire library is arrayed in duplicate in a matrix format to facilitate testing and analysis. For testing here, the array of plasmids in the MPA was expressed in HEK-293T cells for 24 hours. Prior to testing on the array, primary MAb concentrations were determined using an independent immunofluorescence titration curve against wild type hsClaudin 18.2 to ensure that the signal-to-background was optimal for target detection. Cells were permeabilized with 0.1% saponin, each antibody was added to the MPA at 1 ug/mL, and binding across the protein library was measured using high-throughput flow cytometry (Intellicyt HTFC) using a fluorescent secondary antibody. Each array plate contained both positive (Fc-binding) and negative (empty vector) controls to ensure plate-by-plate data validity. Any identified targets were confirmed in a second flow cytometry experiment using serial dilutions of antibody, and the target identity was re-verified by sequencing.

Shotgun Mutagenesis Epitope Mapping of Anti-CLAUDIN 18.2 MAbs

A hsCLDN18.2 expression construct was subjected to high-throughput alanine scanning mutagenesis to generate a comprehensive mutation library. Primers were designed to mutate each residue to alanine, with alanine codons mutated to serine.

The CLDN18.2 mutation library, arrayed in 384-well microplates, was transfected into HEK-293T cells and allowed to express for 22 h. Cells were stained with purified MAb1 (IM-44-09B03-1H1B), MAb2 (IM-44-01E10-1HA), or MAb3 (IM-44-05H06-1HD). MAbs were detected using an Alexa Fluor 488-conjugated secondary antibody (Jackson ImmunoResearch Laboratories, West Grove, Pa.). Cells were washed twice in PBS without calcium or magnesium (PBS−/−) and resuspended in Cellstripper solution (Cellgro, Manassas, Va.) with 0.1% BSA (Sigma-Aldrich, St. Louis, Mo.). Mean cellular fluorescence was detected using an Intellicyt HTFC. MAb reactivities against each mutant CLDN18.2 clone relative to the reactivity against wild type CLDN18.2 protein were calculated by subtracting the signal from mock-transfected controls and normalizing the signal to the signal from wild type CLDN18.2-transfected controls.

Mutated residues within critical clones were identified to be critical to the MAb epitope if they did not support the reactivity of the test MAb but did support the reactivity of a reference CLDN18.2 MAb and additional CLDN18.2 MAbs. This counter-screen strategy facilitates the exclusion of CLDN18.2 mutants that are locally misfolded or that have an expression defect. Residues constituting the MAb epitope were visualized on the homology-based structural model of CLDN18.2 generated from the crystal structure of CLDN18.2 using Phyre2.

The embodiments and examples provided herein provide a surprising and unexpected result that antibodies that can bind specifically to CLAUDIN 18.2 in its native environment, such as a cell membrane, can be generated and that inhibitory antibodies can also be generated. Because of the complexity of the protein these results could not have been predicted or expected.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications in addition to those described herein will become apparent to those skilled in the art from the foregoing description and the accompanying figures. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

What is claimed is:

1. A recombinant antibody, or antigen binding fragment thereof, that binds to a Claudin 18.2 protein, wherein the Claudin 18.2 protein is in its native conformation, wherein the antibody, or antigen binding fragment thereof, comprises: a heavy chain variable ($V_H$) region comprising a heavy chain CDR1 (HCDR1), a heavy chain CDR2 (HCDR2), and a heavy chain CDR3 (HCDR3), and a light chain variable ($V_L$) region comprising a light chain CDR1 (LCDR1), a light chain CDR2 (LCDR2), and a light chain CDR3 (LCDR3), wherein:

(a) the HCDR1 has the amino acid sequence of SEQ ID NO: 28, the HCDR2 has the amino acid sequence of SEQ ID NO: 29, the HCDR3 has the amino acid sequence of SEQ ID NO: 30, the LCDR1 has the amino acid sequence SEQ ID NO: 23; the LCDR2 has the amino acid sequence of SEQ ID NO: 24; and the LCDR3 has the amino acid sequence of SEQ ID NO: 19;

(b) the HCDR1 has an amino acid sequence of SEQ ID NO: 25, the HCDR2 has the amino acid sequence of SEQ ID NO: 26, the HCDR3 has the amino acid sequence of SEQ ID NO: 27, the LCDR1 has the amino acid sequence SEQ ID NO: 23; the LCDR2 has the amino acid sequence of SEQ ID NO: 24; and the LCDR3 has the amino acid sequence of SEQ ID NO: 19; or (c) the HCDR1 has the amino acid sequence of SEQ ID NO: 20, the HCDR2 has the amino acid sequence of SEQ ID NO: 21, the HCDR3 has the amino acid sequence of SEQ ID NO: 22, the LCDR1 has the amino acid sequence SEQ ID NO: 17; the LCDR2 has the amino acid sequence of SEQ ID NO: 18; and the LCDR3 has the amino acid sequence of SEQ ID NO: 19.

2. The antibody, or antigen binding fragment thereof, of claim 1, wherein the antibody, or antigen binding fragment thereof, is a monoclonal antibody.

3. The antibody, or antigen binding fragment thereof, of claim 1, wherein the antibody, or antigen binding fragment thereof, is an scFv antibody.

4. The antibody, or antigen binding fragment thereof, of claim 1, wherein the antibody, or antigen binding fragment thereof, comprises a $V_L$ region having an amino acid sequence that has at least 95% identity to the amino acid sequence of SEQ ID NO: 5, SEQ ID NO: 7, SEQ ID NO: 9, SEQ ID NO: 11, or SEQ ID NO: 13.

5. The antibody, or antigen binding fragment thereof, of claim 1, wherein the antibody, or antigen binding fragment thereof, comprises a $V_L$ region having the amino acid sequence of SEQ ID NO: 5, SEQ ID NO: 7, SEQ ID NO: 9, SEQ ID NO: 11, or SEQ ID NO: 13, or any variant thereof having 1-10 substitutions, deletions, or insertions.

6. The antibody, or antigen binding fragment thereof, of claim 1, wherein the antibody, or antigen binding fragment thereof, comprises a $V_L$ region having the amino acid sequence of SEQ ID NO: 5, SEQ ID NO: 7, SEQ ID NO: 9, SEQ ID NO: 11, or SEQ ID NO: 13, or any variant thereof having 1-10 conservative substitutions.

7. The antibody, or antigen binding fragment thereof, of claim 1, wherein the antibody, or antigen binding fragment thereof, comprises a $V_L$ region having the amino acid sequence of SEQ ID NO: 5, SEQ ID NO: 7, SEQ ID NO: 9, SEQ ID NO: 11, or SEQ ID NO: 13.

8. The antibody, or antigen binding fragment thereof, of claim 1, wherein the antibody, or antigen binding fragment thereof, comprises a $V_H$ region having an amino acid sequence that has at least 95% identity to the amino acid sequence of SEQ ID NO: 4, SEQ ID NO: 6, SEQ ID NO: 8, SEQ ID NO: 10, or SEQ ID NO: 12.

9. The antibody, or antigen binding fragment thereof, of claim 1, wherein the antibody, or antigen binding fragment thereof, comprises a $V_H$ region having the amino acid sequence of SEQ ID NO: 4, SEQ ID NO: 6, SEQ ID NO: 8, SEQ ID NO: 10, or SEQ ID NO: 12, or any variant thereof having 1-10 substitutions, deletions, or insertions.

10. The antibody, or antigen binding fragment thereof, of claim 1, wherein the antibody, or antigen binding fragment thereof, comprises a $V_H$ region having the amino acid sequence of SEQ ID NO: 4, SEQ ID NO: 6, SEQ ID NO: 8, SEQ ID NO: 10, or SEQ ID NO: 12, or any variant thereof having 1-10 conservative substitutions.

11. The antibody, or antigen binding fragment thereof, of claim 1, wherein the antibody, or antigen binding fragment thereof, comprises a $V_H$ region having the amino acid sequence of SEQ ID NO: 4, SEQ ID NO: 6, SEQ ID NO: 8, SEQ ID NO: 10, or SEQ ID NO: 12.

12. The antibody, or antigen binding fragment thereof, of claim 1, wherein the antibody or antigen binding fragment comprises:

a $V_L$ region having the amino acid sequence of SEQ ID NO: 5, or a variant thereof, and a $V_H$ region having the amino acid sequence of SEQ ID NO: 4, or a variant thereof;

a $V_L$ region having the amino acid sequence of SEQ ID NO: 7, or a variant thereof; and a $V_H$ region having the amino acid sequence of SEQ ID NO: 6, or a variant thereof;

a $V_L$ region having the amino acid sequence of SEQ ID NO: 9, or a variant thereof; and a $V_H$ region having the amino acid sequence of SEQ ID NO: 8, or a variant thereof; or a $V_L$ region having the amino acid sequence of SEQ ID NO: 11, or a variant thereof; and a $V_H$ region having the amino acid sequence of SEQ ID NO: 10, or a variant thereof.

13. The antibody, or antigen binding fragment thereof, of claim 1, additionally comprising at least one additional peptide that binds to a different target protein.

14. The antibody, or antigen binding fragment thereof, of claim 13, wherein the different target protein is CD3 or CD28.

15. A nucleic acid molecule encoding an antibody, or antigen binding fragment thereof, of claim 1.

16. A vector comprising the nucleic acid molecule of claim 15.

17. A cell comprising the nucleic acid molecule of claim 15.

18. A pharmaceutical composition comprising the antibody, or antigen binding fragment thereof, of claim 1.

19. A method of treating a tumor or a gastric tumor in a subject, the method comprising administering to the subject the Claudin 18.2 antibody, or antigen binding fragment thereof, of claim 1.

20. The method of claim 19, wherein the tumor or gastric tumor is a gastric adenocarcinoma, gastroesophageal junction adenocarcinoma, or pancreatic adenocarcinoma, or non-small cell lung cancer.

* * * * *

SEQUENCE LISTING

```
Sequence total quantity: 33
SEQ ID NO: 1          moltype = AA  length = 261
FEATURE               Location/Qualifiers
source                1..261
                      mol_type = protein
                      organism = Homo sapiens
SEQUENCE: 1
MAVTACQGLG FVVSLIGIAG IIAATCMDQW STQDLYNNPV TAVFNYQGLW RSCVRESSGF  60
TECRGYFTLL GLPAMLQAVR ALMIVGIVLG AIGLLVSIFA LKCIRIGSME DSAKANMTLT  120
SGIMFIVSGL CAIAGVSVFA NMLVTNFWMS TANMYTGMGG MVQTVQTRYT FGAALFVGWV  180
AGGLTLIGGV MMCIACRGLA PEETNYKAVS YHASGHSVAY KPGGFKASTG FGSNTKNKKI  240
YDGGARTEDE VQSYPSKHDY V                                            261

SEQ ID NO: 2          moltype = AA  length = 261
FEATURE               Location/Qualifiers
source                1..261
                      mol_type = protein
                      organism = Macaca fascicularis
SEQUENCE: 2
MAVTACQGLG FVVSLIGIAG IIAATCMDQW STQDLYNNPV TAVFNYQGLW RSCVRESSGF  60
TECRGYFTLL GLPAMLQAVR ALMIVGIVLG AIGLLVSIFA LKCIRIGSME DSAKANMTLT  120
SGIMFIVSGL CAIAGVSVFA NMLVTNFWMS TANMYTGMGG MVQTVQTRYT FGAALFVGWV  180
```

-continued

```
AGGLTLIGGV MMCIACRGLA PEETNYKAVS YHASGHSVAY KPGGFKASTG FGSNTKNKKT  240
YDGGAHTEDE LQSYPSKHDY V                                            261

SEQ ID NO: 3            moltype = AA  length = 264
FEATURE                 Location/Qualifiers
source                  1..264
                        mol_type = protein
                        organism = Mus musculus
SEQUENCE: 3
MSVTACQGLG FVVSLIGFAG IIAATCMDQW STQDLYNNPV TAVFNYQGLW RSCVRESSGF  60
TECRGYFTLL GLPAMLQAVR ALMIVGIVLG VIGILVSIFA LKCIRIGSMD DSAKAKMTLT  120
SGILFIISGI CAIIGVSVFA NMLVTNFWMS TANMYSGMGG MGGMVQTVQT RYTFGAALFV  180
GWVAGGLTLI GGVMMCIACR GLTPDDSNFK AVSYHASGQN VAYRPGGFKA STGFGSNTRN  240
KKIYDGGART EDDEQSHPTK YDYV                                         264

SEQ ID NO: 4            moltype = AA  length = 133
FEATURE                 Location/Qualifiers
source                  1..133
                        mol_type = protein
                        organism = synthetic construct
SEQUENCE: 4
EVQLLESGGG LVQPGGSLRL SCAASGFTFS SYGMSWVRQA PGKGLEWVAG IGSSGSDTWY  60
ADSVKGRFTI SRDNSKNTLY LQMNSLRAED TAVYYCAKDA TNGYCWYTGR GSYSCGAHHI  120
DAWGQGTLVT VSS                                                     133

SEQ ID NO: 5            moltype = AA  length = 106
FEATURE                 Location/Qualifiers
source                  1..106
                        mol_type = protein
                        organism = synthetic construct
SEQUENCE: 5
SYELTQPPSV SVSPGQTARI TCSGGSGSYG YYGWYQQKPG QAPVTVIYGT NKRPSGIPER  60
FSGSSSGTTV TLTISGVQAE DEADYYCGGY DSSAGIFGGG TKLTVL                 106

SEQ ID NO: 6            moltype = AA  length = 124
FEATURE                 Location/Qualifiers
source                  1..124
                        mol_type = protein
                        organism = synthetic construct
SEQUENCE: 6
EVQLLESGGG LVQPGGSLRL SCAASGFTFR SYAMMWVRQA PGKGLEWVGE ISSTGGSTYY  60
GSAVKGRATI SRDNSKNTLY LQMNSLRAED TAVYYCAKST YGATWKSADS IDAWGQGTLV  120
TVSS                                                               124

SEQ ID NO: 7            moltype = AA  length = 104
FEATURE                 Location/Qualifiers
source                  1..104
                        mol_type = protein
                        organism = synthetic construct
SEQUENCE: 7
SYELTQPPSV SVSPGQTARI TCSGGYNGHY GWYQQKPGQA PVLVIYSNNQ RPSGIPERFS  60
GSSSGTTVTL TISGVQAEDE ADYYCGGYDS SAGIFGGGTK LTVL                   104

SEQ ID NO: 8            moltype = AA  length = 124
FEATURE                 Location/Qualifiers
source                  1..124
                        mol_type = protein
                        organism = synthetic construct
SEQUENCE: 8
EVQLLESGGG LVQPGGSLRL SCAASGFTFR SYAMMWVRQA PGKGLEWVGE ISSTGGSTYY  60
GSAVKGRATI SRDNSKNTLY LQMNSLRAED TAVYYCAKST YGATWKSADS IDAWGQGTLV  120
TVSS                                                               124

SEQ ID NO: 9            moltype = AA  length = 104
FEATURE                 Location/Qualifiers
source                  1..104
                        mol_type = protein
                        organism = synthetic construct
SEQUENCE: 9
SYELTQPPSV SVAPGKTARI TCSGGYNGHY GWYQQKPGQA PVLVIYSNNQ RPSGIPERFS  60
GSNSGNTATL TISRVEAGDE ADYYCGGYDS SAGIFGGGTK LTVL                   104

SEQ ID NO: 10           moltype = AA  length = 132
FEATURE                 Location/Qualifiers
source                  1..132
                        mol_type = protein
                        organism = synthetic construct
SEQUENCE: 10
EVQLLESGGG LVQPGGSLRL SCAASGFTFS SYGMGWVRQA PGKGLEWVAA ITRDSSTNYG  60
```

-continued

```
AAVKGRATIS RDNSKNTLYL QMNSLRAEDT AVYYCAKDAS NGYCWYTGRG SYSCGAHHID  120
AWGQGTLVTV SS                                                      132

SEQ ID NO: 11          moltype = AA  length = 104
FEATURE                Location/Qualifiers
source                 1..104
                       mol_type = protein
                       organism = synthetic construct
SEQUENCE: 11
SYELTQPPSV SVSPGQTARI TCSGGYNGHY GWYQQKPGQA PVTVIYSNNQ RPSGIPERFS  60
GSSSGTTVTL TISGVQAEDE ADYYCGGYDS SAGIFGGGTK LTVL                   104

SEQ ID NO: 12          moltype = AA  length = 132
FEATURE                Location/Qualifiers
source                 1..132
                       mol_type = protein
                       organism = synthetic construct
SEQUENCE: 12
EVQLLESGGG LVQPGGSLRL SCAASGFTFS DYGMGWVRQA PGKGLEWVAA ITIDGSTYYG  60
TAVKGRATIS RDNSKNTLYL QMNSLRAEDT AVYYCAKDAN NGYCWYTGRG SYSCGAHNID  120
AWGQGTLVTV SS                                                      132

SEQ ID NO: 13          moltype = AA  length = 104
FEATURE                Location/Qualifiers
source                 1..104
                       mol_type = protein
                       organism = synthetic construct
SEQUENCE: 13
SYELTQPPSV SVAPGKTARI TCSGGYNGHY GWYQQKPGQA PVLVIYSNNQ RPSGIPERFS  60
GSNSGNTATL TISRVEAGDE ADYYCGGYDS SAGIFGGGTK LTVL                   104

SEQ ID NO: 14          moltype = AA  length = 18
FEATURE                Location/Qualifiers
source                 1..18
                       mol_type = protein
                       organism = synthetic construct
SEQUENCE: 14
GQSSRSSGGG GSSGGGGS                                                18

SEQ ID NO: 15          moltype = AA  length = 5
FEATURE                Location/Qualifiers
source                 1..5
                       mol_type = protein
                       organism = synthetic construct
REPEAT                 1..5
                       note = Linker sequence may be present n times, where n can
                        equal 1, 2, 3, 4, or 5
SEQUENCE: 15
GGGGS                                                              5

SEQ ID NO: 16          moltype = AA  length = 5
FEATURE                Location/Qualifiers
source                 1..5
                       mol_type = protein
                       organism = synthetic construct
REPEAT                 1..5
                       note = Linker sequence may be present n times, where n can
                        equal 1, 2, 3, 4, or 5
SEQUENCE: 16
GGGGA                                                              5

SEQ ID NO: 17          moltype = AA  length = 11
FEATURE                Location/Qualifiers
source                 1..11
                       mol_type = protein
                       organism = synthetic construct
SEQUENCE: 17
SGGSGSYGYY G                                                       11

SEQ ID NO: 18          moltype = AA  length = 7
FEATURE                Location/Qualifiers
source                 1..7
                       mol_type = protein
                       organism = synthetic construct
SEQUENCE: 18
GTNKRPS                                                            7

SEQ ID NO: 19          moltype = AA  length = 9
FEATURE                Location/Qualifiers
```

```
source                  1..9
                        mol_type = protein
                        organism = synthetic construct
SEQUENCE: 19
GGYDSSAGI                                                   9

SEQ ID NO: 20           moltype = AA  length = 5
FEATURE                 Location/Qualifiers
source                  1..5
                        mol_type = protein
                        organism = synthetic construct
SEQUENCE: 20
SYGMS                                                       5

SEQ ID NO: 21           moltype = AA  length = 17
FEATURE                 Location/Qualifiers
source                  1..17
                        mol_type = protein
                        organism = synthetic construct
SEQUENCE: 21
GIGSSGSDTW YADSVKG                                          17

SEQ ID NO: 22           moltype = AA  length = 24
FEATURE                 Location/Qualifiers
source                  1..24
                        mol_type = protein
                        organism = synthetic construct
SEQUENCE: 22
DATNGYCWYT GRGSYSCGAH HIDA                                  24

SEQ ID NO: 23           moltype = AA  length = 9
FEATURE                 Location/Qualifiers
source                  1..9
                        mol_type = protein
                        organism = synthetic construct
SEQUENCE: 23
SGGYNGHYG                                                   9

SEQ ID NO: 24           moltype = AA  length = 7
FEATURE                 Location/Qualifiers
source                  1..7
                        mol_type = protein
                        organism = synthetic construct
SEQUENCE: 24
SNNQRPS                                                     7

SEQ ID NO: 25           moltype = AA  length = 5
FEATURE                 Location/Qualifiers
source                  1..5
                        mol_type = protein
                        organism = synthetic construct
SEQUENCE: 25
SYAMM                                                       5

SEQ ID NO: 26           moltype = AA  length = 17
FEATURE                 Location/Qualifiers
source                  1..17
                        mol_type = protein
                        organism = synthetic construct
SEQUENCE: 26
EISSTGGSTY YGSAVKG                                          17

SEQ ID NO: 27           moltype = AA  length = 15
FEATURE                 Location/Qualifiers
source                  1..15
                        mol_type = protein
                        organism = synthetic construct
SEQUENCE: 27
STYGATWKSA DSIDA                                            15

SEQ ID NO: 28           moltype = AA  length = 5
FEATURE                 Location/Qualifiers
source                  1..5
                        mol_type = protein
                        organism = synthetic construct
SEQUENCE: 28
SYGMG                                                       5

SEQ ID NO: 29           moltype = AA  length = 16
```

-continued

```
FEATURE                Location/Qualifiers
source                 1..16
                       mol_type = protein
                       organism = synthetic construct
SEQUENCE: 29
AITRDSSTNY GAAVKG                                           16

SEQ ID NO: 30          moltype = AA  length = 24
FEATURE                Location/Qualifiers
source                 1..24
                       mol_type = protein
                       organism = synthetic construct
SEQUENCE: 30
DASNGYCWYT GRGSYSCGAH HIDA                                  24

SEQ ID NO: 31          moltype = AA  length = 5
FEATURE                Location/Qualifiers
source                 1..5
                       mol_type = protein
                       organism = synthetic construct
SEQUENCE: 31
DYGMG                                                       5

SEQ ID NO: 32          moltype = AA  length = 16
FEATURE                Location/Qualifiers
source                 1..16
                       mol_type = protein
                       organism = synthetic construct
SEQUENCE: 32
AITIDGSTYY GTAVKG                                           16

SEQ ID NO: 33          moltype = AA  length = 24
FEATURE                Location/Qualifiers
source                 1..24
                       mol_type = protein
                       organism = unidentified
SEQUENCE: 33
DANNGYCWYT GRGSYSCGAH NIDA                                  24
```